(12) United States Patent
Dressen et al.

(10) Patent No.: US 7,101,855 B2
(45) Date of Patent: Sep. 5, 2006

(54) PYROGLUTAMIC ACID DERIVATIVES AND RELATED COMPOUNDS WHICH INHIBIT LEUKOCYTE ADHESION MEDIATED BY VLA-4

(75) Inventors: Darren B. Dressen, San Mateo, CA (US); Anthony Kreft, Langhorne, PA (US); Dennis Kubrak, Philadelphia, PA (US); Charles William Mann, Philadelphia, PA (US); Michael A. Pleiss, Sunnyvale, CA (US); Gary Paul Stack, Ambler, PA (US); Eugene D. Thorsett, Moss Beach, CA (US)

(73) Assignees: Elan Pharmaceuticals, Inc., Madison, NJ (US); Wyeth, Madison, NJ (US)

( * ) Notice: Subject to any disclaimer, the term of this patent is extended or adjusted under 35 U.S.C. 154(b) by 305 days.

(21) Appl. No.: 10/139,382

(22) Filed: May 7, 2002

(65) Prior Publication Data

US 2003/0027771 A1 Feb. 6, 2003

Related U.S. Application Data

(63) Continuation of application No. 09/489,164, filed on Jan. 21, 2000, now Pat. No. 6,407,066.
(60) Provisional application No. 60/198,244, filed on Jan. 26, 1999.

(51) Int. Cl.
*C07K 5/06* (2006.01)

(52) U.S. Cl. .......................... 514/19; 514/18; 530/331; 562/573

(58) Field of Classification Search ................. 514/18, 514/19; 530/331; 562/573
See application file for complete search history.

(56) References Cited

U.S. PATENT DOCUMENTS

| | | | | |
|---|---|---|---|---|
| 4,018,913 A | * | 4/1977 | Okamoto et al. | 514/20 |
| 4,018,915 A | * | 4/1977 | Okamoto et al. | 514/20 |
| 4,108,986 A | | 4/1977 | Wilk | |
| 4,036,955 A | * | 7/1977 | Okamoto et al. | 514/20 |
| 4,041,156 A | * | 8/1977 | Okamoto et al. | 514/20 |
| 4,046,876 A | * | 9/1977 | Okamoto et al. | 514/20 |
| 4,055,636 A | * | 10/1977 | Okamoto et al. | 514/20 |
| 4,055,651 A | * | 10/1977 | Okamoto et al. | 514/319 |
| 4,069,317 A | | 1/1978 | Okamoto et al. | |
| 4,069,318 A | * | 1/1978 | Okamoto et al. | 514/20 |
| 4,070,457 A | * | 1/1978 | Okamoto et al. | 514/510 |
| 4,071,621 A | * | 1/1978 | Okamoto et al. | 514/20 |
| 4,072,743 A | | 2/1978 | Okamoto et al. | |
| 4,072,744 A | | 2/1978 | Okamoto et al. | |
| 4,072,757 A | | 2/1978 | Okamoto et al. | |
| 4,073,891 A | | 2/1978 | Okamoto et al. | |
| 4,073,892 A | | 2/1978 | Okamoto et al. | |
| 4,073,914 A | * | 2/1978 | Kikumoto et al. | 514/319 |
| 4,073,916 A | | 2/1978 | Okamoto et al. | |
| 4,093,712 A | | 6/1978 | Okamoto et al. | |
| 4,096,255 A | * | 6/1978 | Kikumoto et al. | 514/227.5 |
| 4,097,472 A | | 6/1978 | Okamoto et al. | |
| 4,097,591 A | * | 6/1978 | Okamoto et al. | 514/20 |
| 4,104,392 A | * | 8/1978 | Okamoto et al. | 514/307 |
| 4,125,604 A | | 11/1978 | Okamoto et al. | |

(Continued)

FOREIGN PATENT DOCUMENTS

| | | |
|---|---|---|
| AU | 6147073 | 4/1975 |
| EP | 0 526 348 A | 2/1993 |
| GB | 9711143.9 | 5/1997 |
| GB | 9714314.3 | 7/1997 |
| GB | 9714316.8 | 7/1997 |
| GB | 9714335.8 | 7/1997 |
| GB | 9722674.0 | 10/1997 |
| GB | 9800684.4 | 1/1998 |
| GB | 9800686.9 | 1/1998 |
| GB | 9800680.2 | 3/1998 |
| WO | 92-16547 | * 10/1992 |
| WO | 94/07815 | 4/1994 |
| WO | 94/12181 | 6/1994 |
| WO | 95/15973 | 6/1995 |
| WO | 96/01644 | 1/1996 |
| WO | 96/20725 | 7/1996 |
| WO | 96/20949 | 7/1996 |
| WO | 96/22966 | 8/1996 |
| WO | 97/03094 | 1/1997 |
| WO | 97/48726 | 12/1997 |
| WO | 98/04247 | 2/1998 |
| WO | 98/42656 | 10/1998 |
| WO | 98/53814 | 12/1998 |
| WO | 98/53817 | 12/1998 |
| WO | 98/53818 | 12/1998 |
| WO | 98/54207 | 12/1998 |
| WO | 98/58902 | 12/1998 |
| WO | 99/06432 | 2/1999 |
| WO | 99/06436 | 2/1999 |
| WO | 99/10312 | 3/1999 |
| WO | 99/10313 | 3/1999 |
| WO | 99/67230 | 12/1999 |
| WO | 00/43413 | * 7/2000 |

OTHER PUBLICATIONS

V. Simanis, et al., *Int. J. Pept. Protein Res.* (1982), 19(1), 67–70.

(Continued)

*Primary Examiner*—David Lukton
(74) *Attorney, Agent, or Firm*—Foley & Lardner LLP

(57) ABSTRACT

Disclosed are pyroglutamic acid derivatives and related compounds which bind VLA-4. Certain of these compounds also inhibit leukocyte adhesion and, in particular, leukocyte adhesion mediated by VLA-4. Such compounds are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

17 Claims, No Drawings

U.S. PATENT DOCUMENTS

| | | | |
|---|---|---|---|
| 4,140,681 A | | 2/1979 | Okamoto et al. |
| 4,260,601 A | * | 4/1981 | Reichelt et al. ............... 514/18 |
| 4,977,168 A | | 12/1990 | Bernat et al. |
| 4,992,421 A | * | 2/1991 | De et al. ...................... 514/19 |
| 4,997,168 A | * | 3/1991 | Kato ..................... 267/140.13 |
| 5,338,755 A | * | 8/1994 | Wagnon et al. ............. 514/414 |
| 5,397,801 A | * | 3/1995 | Wagnon et al. ............. 514/418 |
| 5,481,005 A | * | 1/1996 | Wagnon et al. ............. 548/537 |
| 5,578,633 A | * | 11/1996 | Wagnon et al. ............. 514/418 |
| 6,221,888 B1 | | 4/2001 | Durette et al. |
| 6,291,511 B1 | | 9/2001 | Durette et al. |
| 6,552,216 B1 | | 4/2003 | Singh et al. |
| 6,686,350 B1 | | 2/2004 | Zheng et al. |

OTHER PUBLICATIONS

D. Leibfritz, et al. *Tetrahedron* (1982), 38(14), 2165–81.

A. M. El–Naggar, et al., *Acta. Pharm. Jugosl.* (1985), 35(1), 15–22.

Chemical Abstract No. 126040, vol. 74, No. 23 (Jun. 7, 1971).

Chemical Abstract No. 176262, vol. 99, No. 21 (Nov. 21, 1983).

Chemical Abstract No. 210288, vol. 106, No. 25 (Jun. 22, 1987).

Chemical Abstract No. 167952, vol. 108, No. 19 (May 9, 1988).

Chemical Abstract No. 34164, vol. 125, No. 3 (Jul. 15, 1996).

Ewenson, A., et al. "Analogues of substance P containing an α–hydroxy, β–amino acid: synthesis and biological activity." *Eur. J. Med. Chem.* 26: 435–442 (1991).

Kato, Y., et al. "Oxidative degradation of collagen and its model peptide by ultraviolet irradiation," *J. Agric. Food. Chem.* 40(3) 373–379 (1992).

Papaioannou, D., et al. "Facile Preparation of the 1–Hydroxybenzotriazolyl Ester of N–Tritylpyroglutamic Acid and its Application to the Synthesis of TRH, [D–His$^2$] TRH and Analogues Incorporationg *cis*–and *trans*–4–Hydroxy–L–proline." *Acta Chemica Scandinavica.* 49: 103–114 (1995).

English Abstract of DE 23573354, (issued Jun. 1974).*

English Abstract of DE 2655636 (issued Jun. 1977).*

English Abstract of JP 04154732 (issued May 1992).*

English Abstract of JP 08073422 (issued Mar. 1996).*

* cited by examiner

PYROGLUTAMIC ACID DERIVATIVES AND RELATED COMPOUNDS WHICH INHIBIT LEUKOCYTE ADHESION MEDIATED BY VLA-4

This application is a continuation of U.S. application Ser. No. 09/489,164, filed on Jan. 21, 2000, now U.S. Pat. No. 6,407,066, which, in turn, claimed the benefit of U.S. Provisional Application Ser. No. 60/198,244, filed on Jan. 26, 1999.

BACKGROUND OF THE INVENTION

1. Field of the Invention

This invention relates to compounds which inhibit leukocyte adhesion and, in particular, leukocyte adhesion mediated by VLA-4.

2. References

The following publications, patents and patent applications are cited in this application as superscript numbers:

[1] Hemler and Takada, European Patent Application Publication No. 330,506, published Aug. 30, 1989
[2] Elices, et al., *Cell*, 60:577–584 (1990)
[3] Springer, *Nature*, 346:425434 (1990)
[4] Osborn, *Cell*, 62:3–6 (1990)
[5] Vedder, et al., *Surgery*, 106:509 (1989)
[6] Pretolani, et al., *J. Exp. Med.*, 180:795 (1994)
[7] Abraham, et al., *J. Clin. Invest.*, 93:776 (1994)
[8] Mulligan, et al., *J. Immunology*, 150:2407 (1993)
[9] Cybulsky, et al., *Science*, 251:788 (1991)
[10] Li, et al., *Arterioscler. Thromb.*, 13:197 (1993)
[11] Sasseville, et al., *Am. J. Path.*, 144:27 (1994)
[12] Yang, et al., *Proc. Nat. Acad. Science (USA)*, 90:10494 (1993)
[13] Burkly, et al., *Diabetes*, 43:529 (1994)
[14] Baron, et al., *J. Clin. Invest.*, 93:1700 (1994)
[15] Hamann, et al., *J. Immunology*, 152:3238 (1994)
[16] Yednock, et al., *Nature*, 356:63 (1992)
[17] Baron, et al., *J. Exp. Med.*, 177:57 (1993)
[18] van Dinther-Janssen, et al., *J. Immunology*, 147:4207 (1991)
[19] van Dinther-Janssen, et al., *Annals. Rheumatic Dis.*, 52:672 (1993)
[20] Elices, et al., *J. Clin. Invest.*, 93:405 (1994)
[21] Postigo, et al., *J. Clin. Invest.*, 89:1445 (1991)
[22] Paul, et al., *Transpl. Proceed.*, 25:813 (1993)
[23] Okarhara, et al., *Can. Res.*, 54:3233 (1994)
[24] Paavonen, et al., *Int. J. Can.*, 58:298 (1994)
[25] Schadendorf, et al., *J. Path.*, 170:429 (1993)
[26] Bao, et al., *Diff.*, 52:239 (1993)
[27] Lauri, et al., *British J. Cancer*, 68:862 (1993)
[28] Kawaguchi, et al., *Japanese J. Cancer Res.*, 83:1304 (1992)
[29] Kogan, et al., U.S. Pat. No. 5,510,332, issued Apr. 23, 1996
[30] International. Patent Appl. Publication No. WO 96/01644

All of the above publications, patents and patent applications are herein incorporated by reference in their entirety to the same extent as if each individual publication, patent or patent application was specifically and individually indicated to be incorporated by reference in its entirety.

3. State of the Art

VLA-4 (also referred to as $\alpha_4\beta_1$ integrin and CD49d/CD29), first identified by Hemier and Takada[1] is a member of the $\beta1$ integrin family of cell surface receptors, each of which comprises two subunits, an $\alpha$ chain and a $\beta$ chain. VLA-4 contains an $\alpha4$ chain and a $\beta1$ chain. There are at least nine $\beta1$ integrins, all sharing the same $\beta1$ chain and each having a distinct $\alpha$ chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently.[2]

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder et al.[5]). Other inflammatory conditions mediated by an adhesion mechanism include, by way of example, asthma[6-8], Alzheimer's disease, atherosclerosis[9-10], AIDS dementia[11], diabetes[12-14] (including acute juvenile onset diabetes), inflammatory bowel disease[15] (including ulcerative colitis and Crohn's disease), multiple sclerosis[16-17], rheumatoid arthritis[18-21], tissue transplantation[22], tumor metastasis[23-28], meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

In view of the above, assays for determining the VLA-4 level in a biological sample containing VLA-4 would be useful, for example, to diagnosis VLA-4 mediated conditions. Additionally, despite these advances in the understanding of leukocyte adhesion, the art has only recently addressed the use of inhibitors of adhesion in the treatment of inflammatory brain diseases and other inflammatory conditions[29,30]. The present invention addresses these and other needs.

SUMMARY OF TH INVENTION

This invention provides compounds which bind to VLA4. Such compounds can be used, for example, to assay for the presence of VLA4 in a sample and in pharmaceutical compositions to inhibit cellular adhesion mediated by VLA-4, for example, binding of VCAM-1 to VLA-4. The compounds of this invention have a binding affinity to VLA-4 as expressed by an $IC_{50}$ of about 15 μM or less (as measured using the procedures described in Example A below) which compounds are defined by formula I below:

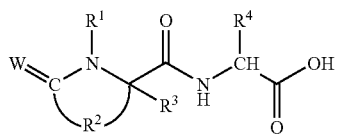

wherein $R^1$ is selected from the group consisting of alkyl, substituted alkyl, aryl, substituted aryl, cycloalkyl, substituted cycloalkyl, heterocyclic, substituted heterocylic, heteroaryl, substituted heteroaryl and —C(O)$OR^1$;

$R^2$ is selected from the group consisting of alkylene having from 2 to 4 carbon atoms in the alkylene chain, substituted alkylene having from 2 to 4 carbon atoms in the alkylene chain, heteroalkylene containing from 1 to 3 carbon atoms and from 1 to 2 heteroatoms selected from nitrogen, oxygen and sulfur and having from 2 to 4 atoms in the heteroalkylene chain, and substituted heteroalkylene containing, in the heteroalkylene chain, from 1 to 3 carbon atoms and from 1 to 2 heteroatoms selected from nitrogen, oxygen and sulfur and having from 2 to 4 atoms in the heteroalkylene chain;

$R^3$ is selected from the group consisting of hydrogen, alkyl, substituted alkyl, cycloalkyl, substituted cycloalkyl, cycloalkenyl, substituted cycloalkenyl, aryl, substituted aryl, heteroaryl, substituted heteroaryl, heterocyclic, substituted heterocyclic; or $R^3$ can be joined to $R^2$ to form a fused cycloalkyl, substituted cycloalkyl, cycloalkenyl, substituted cycloalkenyl, heterocyclic or substituted heterocyclic ring;

$R^4$ is selected from the group consisting of isopropyl, —$CH_2$—X and =CH—X, where X is selected from the group consisting of hydrogen, alkyl, substituted alkyl, cycloalkyl, substituted cycloalkyl, alkoxy, substituted alkoxy, aryl, substituted aryl, aryloxy, substituted aryloxy, aryloxyaryl, substituted aryloxyaryl, heteroaryl, substituted heteroaryl, heterocyclic, substituted heterocyclic, acylamino, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxyheterocyclic, carboxy-substituted heterocyclic, and hydroxyl with the proviso that when $R^4$ is =CH—X then (H) is removed from the formula and X is not hydroxyl;

W is oxygen or sulfur;

and pharmaceutically acceptable salts thereof.

In another embodiment, the compounds of this invention can also be provided as prodrugs which convert (e.g., hydrolyze, metabolize, etc.) in vivo to a compound of formula I above. In a preferred example of such an embodiment, the carboxylic acid in the compound of formula I is modified into a group which, in vivo, will convert to the carboxylic acid (including salts thereof). In a particularly preferred embodiment, such prodrugs are represented by compounds of formula IA:

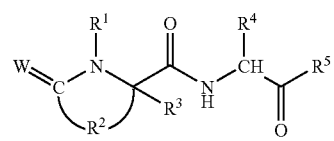

wherein $R^1$ is selected from the group consisting of alkyl, substituted alkyl, aryl, substituted aryl, cycloalkyl, substituted cycloalkyl, heterocyclic, substituted heterocylic, heteroaryl, substituted heteroaryl and —C(O)$OR^1$;

$R^2$ is selected from the group consisting of alkylene having from 2 to 4 carbon atoms in the alkylene chain, substituted alkylene having from 2 to 4 carbon atoms in the alkylene chain, heteroalkylene containing from 1 to 3 carbon atoms and from 1 to 2 heteroatoms selected from nitrogen, oxygen and sulfur and having from 2 to 4 atoms in the heteroalkylene chain, and substituted heteroalkylene containing, in the heteroalkylene chain, from 1 to 3 carbon atoms and from 1 to 2 heteroatoms selected from nitrogen, oxygen and sulfur and having from 2 to 4 atoms in the heteroalkylene chain;

$R^3$ is selected from the group consisting of hydrogen, alkyl, substituted alkyl, cycloalkyl, substituted cycloalkyl, cycloalkenyl, substituted cycloalkenyl, aryl, substituted aryl, heteroaryl, substituted heteroaryl, heterocyclic, substituted heterocyclic; or $R^3$ can be joined to $R^2$ to form a fused cycloalkyl, substituted cycloalkyl, cycloalkenyl, substituted cycloalkenyl, heterocyclic or substituted heterocyclic ring;

$R^4$ is selected from the group consisting of isopropyl, —$CH_2$—X and =CH—X, where X is selected from the group consisting of hydrogen, alkyl, substituted alkyl, cycloalkyl, substituted cycloalkyl, alkoxy, substituted alkoxy, aryl, substituted aryl, aryloxy, substituted aryloxy, aryloxyaryl, substituted aryloxyaryl, heteroaryl, substituted heteroaryl, heterocyclic, substituted heterocyclic, acylamino, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxyheterocyclic, carboxy-substituted heterocyclic, and hydroxyl with the proviso that when $R^4$ is =CH—X then (H) is removed from the formula and X is not hydroxyl;

$R^5$ is selected from the group consisting of amino, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, —NHOY where Y is hydrogen, alkyl, substituted alkyl, aryl, or substituted aryl, and —NH($CH_2$)$_p$COOY' where Y' is hydrogen, alkyl, substituted alkyl, aryl, or substituted aryl, and p is an integer of from 1 to 8;

W is oxygen or sulfur;

and pharmaceutically acceptable salts thereof;

with the provisos that:

(a) when $R^1$ is benzyl, $R^2$ is —$CH_2CH_2$—, $R^3$ is hydrogen, $R^4$ is benzyl, then $R^5$ is not ethyl;

(b) when $R^1$ is 3,4-dichlorobenzyl, $R^2$ is —$CH_2CH_2$—, $R^3$ is hydrogen, $R^4$ is 4-(phenylcarbonylamino)benzyl, then $R^5$ is not methyl;

(c) when $R^1$ is benzyl, $R^2$ is —$CH_2CH_2$—, $R^3$ is hydrogen, $R^4$ is 4-hydroxybenzyl, then $R^5$ is not isopropyl or tert-butyl;

(d) when R¹ is 4-flurobenzyl, R² is —CH₂CH₂—, R³ is hydrogen, R⁵ is tert-butyl, then R⁴ is not 4-hydroxybenzyl or 4-(4-nitrophenoxy-carbonyloxy)benzyl;

(e) when R¹ is 4-cyanobenzyl, R² is —CH₂CH₂—, R³ is hydrogen, R⁴ is 4-hydroxybenzyl, then R⁵ is not tert-butyl; and (f) when R¹ is benzyloxycarbonyl, R² is —NHCH₂—, R³ is hydrogen, R⁵ is tert-butyl, then R⁴ is not 4-hydroxybenzyl or 4-(N,N-dimethylcarbamyloxy)benzyl.

In a preferred embodiment, R¹ is a group having the formula:

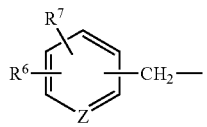

wherein

R⁶ and R⁷ are independently selected from the group consisting of hydrogen, alkyl, alkoxy, amino, cyano, halo and nitro; and Z is CH or N.

Preferably, Z is CH.

Preferably, one of R⁶ and R⁷ is hydrogen and the other is selected from the group consisting of hydrogen, methyl, methoxy, amino, chloro, fluoro, cyano or nitro; or both R⁶ and R⁷ are chloro.

In a particularly preferred embodiment, R¹ is selected from the group consisting of benzyl, 4-aminobenzyl, 3-chlorobenzyl, 4-chlorobenzyl, 3,4-dichlorobenzyl, 4-cyanobenzyl, 4-fluorobenzyl, 4-methylbenzyl, 4-methoxybenzyl, 4-nitrobenzyl, benzyloxycarbonyl, (pyrdin-3-yl)methyl and the like.

Preferably, R² is selected from the group consisting of alkylene having 2 or 3 carbon atoms in the alkylene chain, substituted alkylene having 2 or 3 carbon atoms in the alkylene chain, heteroalkylene containing 1 or 2 carbon atoms and 1 heteroatom selected from nitrogen, oxygen and sulfur and having 2 or 3 atoms in the heteroalkylene chain, and substituted heteroalkylene containing, in the heteroalkylene chain, 1 or 2 carbon atoms and 1 heteroatom selected from nitrogen, oxygen and sulfur and having 2 or 3 atoms in the heteroalkylene chain.

In a particularly preferred embodiment, R² is selected from the group consisting of —CH₂CH₂—, —CH₂—S—CH₂—, —CH₂—O—CH₂— and —NHCH₂—. Accordingly, R² when joined with the other atoms of the nitrogen-containing ring structure preferably forms a 2-pyrrolidinone, 3-oxothiomorpholine, 3-oxomorpholine or 2-imidazolidinone ring. In another preferred embodiment, R³ is joined to R² to form a 5-oxo-4-azatricyclo[4.2.1.0 (3,7)]nonane ring.

Preferably, in the compounds of formula I and IA above, R³ is hydrogen or it is joined with R² to form a 5-oxo-4-azatricyclo[4.2.1.0 (3,7)]nonane ring. More preferably, R³ is hydrogen.

R⁴ is preferably selected from all possible isomers arising by substitution with the following groups:
4-methylbenzyl,
4-hydroxybenzyl,
4-methoxybenzyl,
4-t-butoxybenzyl,
4-benzyloxybenzyl,
4-[φ-CH(CH₃)O—]benzyl,
4-[φ-CH(COOH)O—]benzyl,
4-[BocNHCH₂C(O)NH—]benzyl,
4-chlorobenzyl,
4-[NH₂CH₂C(O)NH—]benzyl,
4-carboxybenzyl,
4-[CbzNHCH₂CH₂NH—]benzyl,
3-hydroxy-4-(φ-OC(O)NH—)benzyl,
4-[HOOCCH₂CH₂C(O)NH—]benzyl,
benzyl,
4-[2'-carboxylphenoxy—]benzyl,
4-[φ-C(O)NH—]benzyl,
3-carboxybenzyl,
4-iodobenzyl,
4-hydroxy-3,5-diiodobenzyl,
4-hydroxy-3-iodobenzyl,
4-[2'-carboxyphenyl—]benzyl,
φ-CH₂CH₂—,
4-nitrobenzyl,
2-carboxybenzyl,
4-[dibenzylamino]-benzyl,
4-[(1'-cyclopropylpiperidin-4'-yl)C(O)NH—]benzyl,
4-[—NHC(O)CH₂NHBoc]benzyl,
4-carboxybenzyl,
4-hydroxy-3-nitrobenzyl,
4-[—NHC(O)CH(CH₃)NHBoc]benzyl,
4-[—NHC(O)CH(CH₂φ)NHBoc]benzyl,
isobutyl,
methyl,
4-[CH₃C(O)NH—]benzyl,
—CH₂-(3-indolyl),
n-butyl,
t-butyl-OC(O)CH₂—,
t-butyl-OC(O)CH₂CH₂—,
H₂NC(O)CH₂—,
H₂NC(O)CH₂CH₂—,
BocNH—(CH₂)₄—,
t-butyl-OC(O)—(CH₂)₂—,
HOOCCH₂—,
HOOC(CH₂)₂—,
H₂N(CH₂)₄—,
isopropyl,
(1-naphthyl)-CH₂—,
(2-naphthyl)-CH₂—,
(2-thiophenyl)-CH₂—,
(φ-CH₂—OC(O)NH—(CH₂)₄—,
cyclohexyl-CH₂—,
benzyloxy-CH₂—,
HOCH₂—,
5-(3-N-benzyl)imidazolyl-CH₂—,
2-pyridyl-CH₂—,
3-pyridyl-CH₂—,
4-pyridyl-CH₂—,
5-(3-N-methyl) imidazolyl-CH₂—,
N-benzylpiperid-4-yl-CH₂—,
N-Boc-piperidin-4-yl-CH₂—, N-(phenyl-carbonyl)piperidin-4-yl-$CH_2$—,
$H_3CSCH_2CH_2$—,
1-N-benzylimidazol-4-yl-$CH_2$—,
iso-propyl-C(O)NH—$(CH_2)_4$—,
iso-butyl-C(O)NH—$(CH_2)_4$—,
phenyl-C(O)NH—$(CH_2)_4$—,
benzyl-C(O)NH—$(CH_2)_4$—,
allyl-C(O)NH—$(CH_2)_4$—,
4-(3-N-methylimidazolyl)-$CH_2$—,
4-imidazolyl,
4-[$(CH_3)_2NCH_2CH_2CH_2$—O—]benzyl,
4-[$(benzyl)_2N$—]-benzyl,
4-aminobenzyl,
allyloxy-C(O)NH$(CH_2)_4$—,
allyloxy-C(O)NH$(CH_2)_3$—,
allyloxy-C(O)NH$(CH_2)_2$—,
$NH_2C(O)CH_2$—,
φ-CH=,
2-pyridyl-C(O)NH-$(CH_2)_4$—,
4-methylpyrid-3-yl-C(O)NH-$(CH_2)_4$—,
3-methylthien-2-yl-C(O)NH-$(CH_2)_4$—,
2-pyrrolyl-C(O)NH—$(CH_2)_4$—,
2-furanyl-C(O)NH—$(CH_2)_4$—,
4-methylphenyl-$SO_2$—N($CH_3$)$CH_2$C(O)NH$(CH_2)_4$—,
4-[cyclopentylacetylenyl]-benzyl,
4-[—NHC(O)—(N-Boc)-pyrrolidin-2-yl)]-benzyl-,
1-N-methylimidazol-4-yl-$CH_2$—,
1-N-methylimidazol-5-yl-$CH_2$—,
imidazol-5-yl-$CH_2$—,
6-methylpyrid-3-yl-C(O)NH—$(CH_2)_4$—,
4-[2'-carboxymethylphenyl]-benzyl,
4-[—NHC(O)NH$CH_2CH_2CH_2$-φ]-benzyl,
4-[—NHC(O)NH$CH_2CH_2$-φ]-benzyl,
—$CH_2$C(O)NH$(CH_2)_4$φ,
4-[φ$(CH_2)_4$O—]-benzyl,
4-[—C≡C-φ-4'φ]-benzyl,
4-[—C≡C—$CH_2$—O—S(O)$_2$-4'-$CH_3$-φ]-benzyl,
4-[—C≡C—$CH_2$NHC(O)$NH_2$]-benzyl,
4-[—C≡C—$CH_2$—O—4'-COOC$H_2CH_3$-φ]-benzyl,
4-[—C≡C—CH($NH_2$)-cyclohexyl]-benzyl,
—$(CH_2)_4$NHC(O)$CH_2$-3-indolyl,
—$(CH_2)_4$NHC(O)$CH_2CH_2$-3-indolyl,
—$(CH_2)_4$NHC(O)-3-(5-methoxyindolyl),
—$(CH_2)_4$NHC(O)-3-(1-methylindolyl),
—$(CH_2)_4$NHC(O)-4-(-$SO_2$($CH_3$)-φ),
—$(CH_2)_4$NHC(O)-4-(C(O)$CH_3$)-phenyl,
—$(CH_2)_4$NHC(O)-4-fluorophenyl,
—$(CH_2)_4$NHC(O)$CH_2$O-4-fluorophenyl,
4-[—C≡C-(2-pyridyl)]benzyl,
4-[—C≡C—$CH_2$—O-phenyl]benzyl,
4-[—C≡C—$CH_2OCH_3$]benzyl,
4-[—C≡C-(3-hydroxyphenyl)]benzyl,
4-[—C≡C—$CH_2$—O-4'-(-C(O)O$C_2H_5$)phenyl]benzyl,
4-[—C≡C—$CH_2$CH(C(O)O$CH_3$)]benzyl,
4-[-C≡C—$CH_2$NH-(4,5-dihydro-4-oxo-5-phenyl-oxazol-2-yl),
3-aminobenzyl,
4-[-C≡C—$CH_2$CH(NHC(O)$CH_3$)C(O)OH]-benzyl,
—$CH_2$C(O)NHCH($CH_3$)φ,
—$CH_2$C(O)NH$CH_2$-(4-dimethylamino)-φ,
—$CH_2$C(O)NH$CH_2$-4-nitrophenyl,
—$CH_2CH_2$C(O)N($CH_3$)$CH_2$-φ,
—$CH_2CH_2$C(O)NH$CH_2CH_2$-(N-methyl)-2-pyrrolyl,
—$CH_2CH_2$C(O)NH$CH_2CH_2CH_3$,
—$CH_2CH_2$C(O)NH$CH_2CH_2$-3-indolyl,
—$CH_2$C(O)N($CH_3$)$CH_2$phenyl,
—$CH_2$C(O)NH$(CH_2)_2$-(N-methyl)-2-pyrrolyl,
—$CH_2$C(O)NH$CH_2CH_2CH_3$,
—$CH_2$C(O)NH$CH_2CH_2$-3-indolyl,
—$(CH_2)_2$C(O)NHCH($CH_3$)φ,
—$(CH_2)_2$C(O)NH$CH_2$-4-dimethylaminophenyl,
—$(CH_2)_2$C(O)NH$CH_2$-4-nitrophenyl,
—$CH_2$C(O)NH-4-[—NHC(O)$CH_3$-phenyl],
—$CH_2$C(O)NH-4-pyridyl,
—$CH_2$C(O)NH-4-[dimethylaminophenyl],
—$CH_2$C(O)NH-3-methoxyphenyl,
—$CH_2CH_2$C(O)NH-4-chlorophenyl,
—$CH_2CH_2$C(O)NH-2-pyridyl,
—$CH_2CH_2$C(O)NH-4-methoxyphenyl,
—$CH_2CH_2$C(O)NH-3-pyridyl,
4-[$(CH_3)_2NCH_2CH_2O$—]benzyl,
—$(CH_2)_3$NHC(NH)NH—$SO_2$-4-methylphenyl,
4-[$(CH_3)_2NCH_2CH_2O$—]benzyl,
—$(CH_2)_4$NHC(O)NH$CH_2CH_3$,
—$(CH_2)_4$NHC(O)NH-phenyl,
—$(CH_2)_4$NHC(O)NH-4-methoxyphenyl,
4-[4'-pyridyl-C(O)NH—]benzyl,
4-[3'-pyridyl-C(O)NH—]benzyl,
4-[—NHC(O)NH-3'-methylphenyl]benzyl,
4-[—NHC(O)$CH_2$NHC(O)NH-3'-methylphenyl]benzyl,
4-[—NHC(O)-(2', 3'-dihydroindol-2-yl)]benzyl,
4-[—NHC(Q)-(2', 3'-dihydro-N-Boc-indol-2-yl)]benzyl,
p-[—OCH$_2CH_2$-1'-(4'-pyrimidinyl)-piperazinyl]benzyl,
4-[—OCH$_2CH_2$-(1'-piperidinyl)benzyl,
4-[—OCH$_2CH_2$-(1'-pyrrolidinyl)]benzyl,
4-[—OCH$_2CH_2CH_2$-(1'-piperidinyl)]benzyl-,
—$CH_2$-3-(1,2,4-triazolyl),
4-[—OCH$_2CH_2CH_2$-4-(3'-chlorophenyl)-piperazin-1-yl] benzyl,
4-[—OCH$_2CH_2$N(φ)$CH_2CH_3$]benzyl,
4-[—OCH$_2$-3 '-(N-Boc)-piperidinyl]benzyl,
4-[di-n-pentylamino]benzyl,
4-[n-pentylamino]benzyl,
4-[di-iso-propylamino-$CH_2CH_2$O—]benzyl,
4-[—OCH$_2CH_2$—(N-morpholinyl)]benzyl,
4-[—O-(3'-(N-Boc)-piperidinyl]benzyl,
4-[—OCH$_2$CH(NHBoc)$CH_2$cyclohexyl]benzyl,
p-[OCH$_2CH_2$—(N-piperidinyl]benzyl,
4-[—OCH$_2CH_2CH_2$-(4-m-chlorophenyl)-piperazin-1-yl] benzyl,
4-[—OCH$_2CH_2$—(N-homopiperidinyl)benzyl,
4-[—NHC(O)-3'-(N-Boc)-piperidinyl]benzyl,
4-[—OCH$_2CH_2$N(benzyl)$_2$]benzyl,
—$CH_2$-2-thiazolyl, 3-hydroxybenzyl,
4-[—OCH₂CH₂CH₂N(CH₃)₂]benzyl,
4-[—NHC(S)NHCH₂CH₂—(N-morpholino)]benzyl,
4-[—OCH₂CH₂N(C₂H₅)₂]benzyl,
4-[—OCH₂CH₂CH₂N(C₂H₅)₂]benzyl,
4-[CH₃(CH₂)₄NH—]benzyl,
4-[N-n-butyl,N-n-pentylamino—]benzyl,
4-[—NHC(O)-4'-piperidinyl]benzyl,
4-[—NHC(O)CH(NHBoc)(CH₂)₄NHCbz]benzyl,
4-[—NHC(O)-(1',2',3',4'-tetrahydro-N-Boc-isoquinolin-1'-yl]benzyl,
p-[—OCH₂CH₂CH₂-1'-(4'-methyl)-piperazinyl]benzyl,
—(CH₂)₄NH-Boc,
3-[—OCH₂CH₂CH₂N(CH₃)₂]benzyl,
4-[—OCH₂CH₂CH₂N(CH₃)₂]benzyl,
3-[—OCH₂CH₂-(1'-pyrrolidinyl)]benzyl,
4-[—OCH₂CH₂CH₂N(CH₃)benzyl]benzyl,
4-[—NHC(S)NHCH₂CH₂CH₂—(N-morpholino)]benzyl,
4-[—OCH₂CH₂—(N-morpholino)]benzyl,
4-[—NHCH₂-(4'-chlorophenyl))benzyl,
4-[—NHC(O)NH-(4'-cyanophenyl)]benzyl,
4-[—OCH₂COOH]benzyl,
4-[—OCH₂COO-t-butyl]benzyl,
4-[—NHC(O)-5'-fluoroindol-2-yl]benzyl,
4-[—NHC(S)NH(CH₂)₂-1-piperidinyl]benzyl,
4-[-N(SO₂CH₃)(CH₂)₃—N(CH₃)₂]benzyl,
4-[—NHC(O)CH₂CH(C(O)OCH₂ϕ)—NHCbz]benzyl,
4-[—NHS(O)₂CF₃]benzyl,
3-[—O-(N-methylpiperidin4'-yl]benzyl,
4-[-C(=NH)NH₂]benzyl,
4-[—NHSO₂-CH₂Cl]benzyl,
4-[—NHC(O)-(1',2',3',4'-tetrahydroisoquinolin-2'-yl]benzyl,
4-[—NHC(S)NH(CH₂)₃—N-morpholino]benzyl,
4-[—NHC(O)CH(CH₂CH₂CH₂CH₂NH₂)NHBoc]benzyl,
4-[-C(O)NH₂]benzyl,
4-[—NHC(O)NH-3'-methoxyphenyl]benzyl,
4-[—OCH₂CH₂-indol-3'-yl]benzyl,
4-[—OC₂C(O)NH-benzyl]benzyl,
4-[—OCH₂C(O)O-benzyl]benzyl,
4-[—OCH₂C(O)OH]benzyl,
4-[—OCH₂-2'-(4',5'-dihydro)imidazolyl]benzyl,
—CH₂C(O)NHCH₂-(4-dimethylamino)phenyl,
—CH₂C(O)NHCH₂-(4-dimethylamino)phenyl,
4-[—NHC(O)-L-2'-pyrrolidinyl—N—SO₂-4'-methylphenyl]benzyl,
4-[—NHC(O)NHCH₂CH₂CH₃]benzyl,
4-aminobenzyl]benzyl,
4-[—OCH₂CH₂-1-(4-hydroxy-4-(3-methoxypyrrol-2-yl)-piperazinyl]benzyl,
4-[—O—(N-methylpiperidin-4'-yl)]benzyl,
3-methoxybenzyl,
4-[—NHC(O)-piperidin-3'-yl]benzyl,
4-[—NHC(O)-pyridin-2'-yl]benzyl,
4-[—NHCH₂-(4'-chlorophenyl)]benzyl,
4-[—NHC(O)—(N-(4'-CH3-ϕ-SO₂)-L-pyrrolidin-2'-yl)]benzyl,
4-[—NHC(O)NHCH₂CH₂-ϕ]benzyl,
4-[—OCH₂C(O)NH₂]benzyl,
4-[—OCH₂C(O)NH-t-butyl]benzyl,
4-[—OCH₂CH₂-1-(4-hydroxy-4-phenyl)-piperidinyl]benzyl,
4-[—NHSO₂—CH=CH₂]benzyl,
4-[—NHSO₂—CH₂CH₂Cl]benzyl,
—CH₂C(O)NHCH₂CH₂N(CH₃)₂,
4-[(1'-Cbz-piperidin-4'-yl)C(O)NH—]benzyl,
4-[(1'-Boc-piperidin-4'-yl)C(O)NH—]benzyl,
4-[(2'-bromophenyl)C(O)NH—]benzyl,
4-[—NHC(O)-pyridin-4'-yl]benzyl,
4-[(4'-(CH₃)₂NC(O)O—)phenyl)-C(O)NH—]benzyl,
4-[—NHC(O)-1'-methylpiperidin-4'-yl—]benzyl,
4-(dimethylamino)benzyl,
4-[—NHC(O)-(1'-N-Boc)-piperidin-2'-yl]benzyl,
3-[—NHC(O)-pyridin-4'-yl]benzyl,
4-[(tert-butyl-O(O)CCH₂—O-benzyl)-NH—]benzyl,
[BocNHCH₂C(O)NH—]butyl,
4-benzylbenzyl,
2-hydroxyethyl,
4-[(Et)₂NCH₂CH₂CH₂NHC(S)NH—]benzyl,
4-[(1'-Boc-4'-hydroxypyrrolidin-2'-yl)C(O)NH—]benzyl,
4-[ϕCH₂CH₂CH₂NHC(S)NH—]benzyl,
4-[(perhydroindolin-2'-yl)C(O)NH—]benzyl,
2-[4-hydroxy-4-(3-methoxythien-2-yl)piperidin-1-yl]ethyl,
4-[(1'-Boc-perhydroindolin-2'-yl)-C(O)NH—]benzyl,
4-[N-3-methylbutyl-N-trifluoromethanesulfonyl)amino]benzyl,
4-[N-vinylsulfonyl)amino]benzyl,
4-[2-(2-azabicyclo[3.2.2]octan-2-yl)ethyl-O—]benzyl,
4-[4'-hydroxypyrrolidin-2'-yl)C(O)NH—]benzyl,
4-(ϕNHC(S)NH)benzyl,
4-(EtNHC(S)NH)benzyl,
4-(ϕCH₂NHC(S)NH)benzyl,
3-[(1'-Boc-piperidin-2'-yl)C(O)NH—]benzyl,
3-[piperidin-2'-yl-C(O)NH—]benzyl,
4-[(3'-Boc-thiazolidin-4'-yl)C(O)NH—]benzyl,
4-(pyridin-3'-yl-NHC(S)NH)benzyl,
4-(CH₃-NHC(S)NH)benzyl,
4-(H₂NCH₂CH₂CH₂C(O)NH)benzyl,
4-(BocHNCH₂CH₂CH₂C(O)NH)benzyl,
4-(pyridin-4'-yl-CH₂NH)benzyl,
4-[(N,N-di(4-N,N-dimethylamino)benzyl)amino]benzyl,
4-[(1-Cbz-piperidin-4-yl)C(O)NH—]butyl,
4-[ϕCH₂OCH₂(BocHN)CHC(O)NH]benzyl,
4-[(piperidin-4'-yl)C(O)NH—]benzyl,
4-[(pyrrolidin-2'-yl)C(O)NH—]benzyl,
4-(pyridin-3'-yl-C(O)NH)butyl,
4-(pyridin-4'-yl-C(O)NH)butyl,
4-(pyridin-3'-yl-C(O)NH)benzyl,
4-[CH₃NHCH₂CH₂CH₂C(O)NH—]benzyl,
4-[CH₃N(Boc)CH₂CH₂CH₂C(O)NH—]benzyl,
4-(aminomethyl)benzyl,
4-[ϕCH₂OCH₂(H₂N)CHC(O)NH]benzyl, 4-[(1',4'-di(Boc)piperazin-2'-yl)-C(O)NH—]benzyl,
4-[(piperazin-2'-yl)-C(O)NH—]benzyl,
4-[(N-toluenesulfonylpyrrolidin-2'-yl)C(O)NH—]butyl,
4-[—NHC(O)-4'-piperidinyl]butyl,
4-[—NHC(O)-1'-N-Boc-piperidin-2'-yl]benzyl,
4-[—NHC(O)-piperidin-2'-yl]benzyl,
4-[(1'-N-Boc-2',3'-dihydroindolin-2'-yl)-C(O)NH]benzyl,
4-(pyridin-3'-yl-CH$_2$NH)benzyl,
4-[(piperidin-1'-yl)C(O)CH$_2$—O—]benzyl,
4-[(CH$_3$)$_2$CH)$_2$NC(O)CH$_2$—O—]benzyl,
4-[HO(O)C(Cbz-NH)CHCH$_2$CH$_2$—C(O)NH—]benzyl,
4-[φCH$_2$O(O)C(Cbz-NH)CHCH$_2$CH$_2$—C(O)NH—]benzyl,
4-[—NHC(O)-2'-methoxyphenyl]benzyl,
4-[(pyrazin-2'-yl)C(O)NH—]benzyl,
4-[HO(O)C(NH$_2$)CHCH$_2$CH$_2$—C(O)NH—]benzyl,
4-(2'-formyl-1',2',3',4'-tetrahydroisoquinolin-3'-yl-CH$_2$NH—)benzyl,
N-Cbz-NHCH$_2$—,
4-[(4'-methylpiperazin-1'-yl)C(O)O—]benzyl,
4-[CH$_3$(N-Boc)NCH$_2$C(O)NH—]benzyl,
4-[—NHC(O)-(1',2',3',4'-tetrahydro-N-Boc-isoquinolin-3'-yl]-benzyl,
4-[CH$_3$NHCH$_2$C(O)NH—]benzyl,
(CH$_3$)$_2$NC(O)CH$_2$—,
4-(N-methylacetamido)benzyl,
4-(1',2',3',4'-tetrahydroisoquinolin-3'-yl-CH$_2$NH—)benzyl,
4-[(CH$_3$)$_2$NHCH$_2$C(O)NH—]benzyl,
(1-toluenesulfonylimidizol-4-yl)methyl,
4-[(1'-Boc-piperidin-4'-yl)C(O)NH—]benzyl,
4-trifluoromethylbenzyl,
4-[(2'-bromophenyl)C(O)NH—]benzyl,
4-[(CH$_3$)$_2$NC(O)NH—]benzyl,
4-[CH$_3$OC(O)NH—]benzyl,
4-[(CH$_3$)$_2$NC(O)O—]benzyl,
4-[(CH$_3$)$_2$NC(O)N(CH$_3$)—]benzyl,
4-[CH$_3$OC(O)N(CH$_3$)—]benzyl,
4-(N-methyltrifluoroacetamido)benzyl,
4-[(1'-methoxycarbonylpiperidin-4'-yl)C(O)NH—]benzyl,
4-[(4'-phenylpiperidin-4'-yl)C(O)NH—]benzyl,
4-[(4'-phenyl-1'-Boc-piperidin-4'-yl)-C(O)NH—]benzyl,
4-[(piperidin-4'-yl)C(O)O—]benzyl, 4-[(1'-methylpiperidin-4'-yl)-O—]benzyl,
4-[(1'-methylpiperidin-4'-yl)C(O)O—]benzyl,
4-[(4'-methylpiperazin-1'-yl)C(O)NH—]benzyl,
3-[(CH$_3$)$_2$NC(O)O—]benzyl,
4-[(4'-phenyl-1'-Boc-piperidin-4'-yl)-C(O)O—]benzyl,
4-(N-toluenesulfonylamino)benzyl,
4-[(CH$_3$)$_3$CC(O)NH—]benzyl,
4-[(morpholin-4'-yl)C(O)NH—]benzyl,
4-[(CH$_3$CH$_2$)$_2$NC(O)NH—]benzyl,
4-[-C(O)NH-(4'-piperidinyl)]benzyl,
4-[(2'-trifluoromethylphenyl)C(O)NH—]benzyl,
4-[(2'-methylphenyl)C(O)NH—]benzyl,
4-[(CH$_3$)$_2$NS(O)$_2$O—]benzyl,
4-[(pyrrolidin-2'-yl)C(O)NH—]benzyl,
4-[—NHC(O)-piperidin-1'-yl]benzyl,
4-[(thiomorpholin-4'-yl)C(O)NH—]benzyl,
4-[(thiomorpholin-4'-yl sulfone)-C(O)NH—]benzyl,
4-[(morpholin-4'-yl)C(O)O—]benzyl,
3-nitro-4-(CH$_3$OC(O)CH$_2$O—)benzyl,
(2-benzoxazolinon-6-yl)methyl-,
(2H-1,4-benzoxazin-3(4H)-one-7-yl)methyl-,
4-[(CH$_3$)$_2$NS(O)$_2$NH—]benzyl,
4-[(CH$_3$)$_2$NS(O)$_2$N(CH$_3$)—]benzyl,
4-[(thiomorpholin-4'-yl)C(O)O—]benzyl,
4-[(thiomorpholin-4'-yl sulfone)-C(O)O—]benzyl,
4-[(piperidin-1'-yl)C(O)O—]benzyl,
4-[(pyrrolidin-1'-yl)C(O)O—]benzyl,
4-[(4'-methylpiperazin-1'-yl)C(O)O—]benzyl,
4-[(2'-methylpyrrolidin-1'-yl)-,
(pyridin-4-yl)methyl-,
4-[(piperazin-4'-yl)-C(O)O—]benzyl,
4-[(1'-Boc-piperazin-4'-yl)-C(O)O—]benzyl,
4-[(4'-acetylpiperazin-1'-yl)C(O)O—]benzyl,
p-[(4'-methanesulfonylpiperazin-1'-yl)-benzyl,
3-nitro-4-[(morpholin-4'-yl)-C(O)O—]benzyl,
4-{[(CH$_3$)$_2$NC(S)]$_2$N—}benzyl,
N-Boc-2-aminoethyl-,
4-[(1,1-dioxothiomorpholin4-yl)-C(O)O—]benzyl,
4-[(CH$_3$)$_2$NS(O)$_2$—]benzyl,
4-(imidazolid-2'-one-1'-yl)benzyl,
4-[(piperidin-1'-yl)C(O)O—]benzyl,
1-N-benzyl-imidazol4-yl-CH$_2$—,
3,4-dioxyethylenebenzyl,
3,4-dioxymethylenebenzyl,
4-[-N(SO$_2$)(CH$_3$)CH$_2$CH$_2$CH$_2$N(CH$_3$)$_2$]benzyl,
4-(3'-formylimidazolid-2'-one-1'-yl)benzyl,
4-[NHC(O)CH(CH$_2$CH$_2$CH$_2$CH$_2$NH$_2$)NHBoc]benzyl,
[2'-[4"-hydroxy4"-(3'"-methoxythien-2'"-yl)piperidin-2"-yl]ethoxy]benzyl and
p-[(CH$_3$)$_2$NCH$_2$CH$_2$N(CH$_3$)C(O)O—]benzyl.

In a preferred embodiment, $R^4$ is preferably selected from all possible isomers arising by substitution with the following groups:
benzyl,
4-aminobenzyl,
4-hydroxybenzyl,
4-nitrobenzyl,
3-chloro-4-hydroxybenzyl,
4-(phenylC(O)NH—)benzyl,
4-(pyridin-4-ylC(O)NH—)benzyl,
4-[(CH$_3$)$_2$NC(O)O—]benzyl,
4-[(1'-Cbz-piperidin-4'-yl)C(O)NH—]benzyl,
4-[(piperidin-4'-yl)C(O)NH—]benzyl,
4-[—O—(N-methylpiperidin-4'-yl)]benzyl,
4-[(4'-methylpiperazin-1'-yl)C(O)O—]benzyl,
4-[(4'-(pyridin-2-yl)piperazin-1'-yl)C(O)O—]benzyl,
4-[(thiomorpholin-4'-yl)C(O)O—]benzyl,
3-chloro-4-[(CH$_3$)$_2$NC(O)O—]benzyl, and
5-(3-N-benzyl)imidazolyl-CH$_2$—.

In the compounds of formula IA, $R^5$ is preferably 2,4-dioxo-tetrahydrofuran-3-yl (3,4-enol), methoxy, ethoxy, iso-propoxy, n-butoxy, t-butoxy, cyclopentoxy, neo-pentoxy, 2-α-iso-propyl-4-β-methylcyclohexoxy, 2-β-isopropyl-4-β-methylcyclohexoxy, —NH$_2$, benzyloxy, —NHCH$_2$COOH, —NHCH$_2$CH$_2$COOH, —NH-adamantyl, —NHCH$_2$CH$_2$COOCH$_2$CH$_3$, —NHSO$_2$-p-CH$_3$-φ, —NHOR$^8$ where R$^8$ is hydrogen, methyl, iso-propyl or benzyl, O—(N-succinimidyl), —O-cholest-5-en-3-β-yl, —OCH$_2$—OC(O)C(CH$_3$)$_3$, —O(CH$_2$)$_z$NHC(O)R$^9$ where z is 1 or 2 and R$^9$ is selected from the group consisting of pyrid-3-yl, N-methylpyridyl, and N-methyl-1,4-dihydropyrid-3-yl, -NR"C(O)—R' where R' is aryl, heteroaryl or heterocyclic and R" is hydrogen or —CH$_2$C(O)OCH$_2$CH$_3$.

In the compounds of formula I and IA above, W is preferably oxygen.

Preferred compounds within the scope of formula I and IA above include by way of example:

N-(benzyl)-L-pyroglutamyl-L-phenylalanine
N-(benzyloxycarbonyl)-L-pyroglutamyl-L-phenylalanine
N-(benzyl)-L-pyroglutamyl-L-4-(phenylcarbonylamino)phenylalanine
N-(3,4-dichlorobenzyl)-L-pyroglutamyl-L-4-(phenylcarbonylamino)phenylalanine
N-(3-chlorobenzyl)-L-pyroglutamyl-L-4-(phenylcarbonylamino)phenylalanine
N-(3-chlorobenzyl)-L-pyroglutamyl-L-4-(phenylcarbonylamino)phenylalanine methyl ester
N-(4-chlorobenzyl)-L-pyroglutamyl-L-4-(phenylcarbonylamino)phenylalanine
N-(4-chlorobenzyl)-L-pyroglutamyl-L-4-(phenylcarbonylamino)phenylalanine methyl ester
N-(4-methylbenzyl)-L-pyroglutamyl-L-4-(phenylcarbonylamino)phenylalanine
N-(4-methylbenzyl)-L-pyroglutamyl-L-4-(phenylcarbonylamino)phenylalanine methyl ester
N-(4-methoxybenzyl)-L-pyroglutamyl-L-4-(phenylcarbonylamino)phenylalanine
N-(4-methoxybenzyl)-L-pyroglutamyl-L-4-(phenylcarbonylamino)phenylalanine methyl ester
N-(3-chlorobenzyl)-L-pyroglutamyl-L-(N'-benzyl)histidine
N-(4-methylbenzyl)-L-pyroglutamyl-L-(N'-benzyl)histidine methyl ester
N-(4-methylbenzyl)-L-pyroglutamyl-L-(N'-benzyl)histidine
N-(benzyl)-D-pyroglutamyl-L-phenylalanine
N-(4-benzyl-3-oxothiomorpholin-5-carbonyl)-L-phenylalanine
N-(4-benzyl-3-oxothiomorpholin-5-carbonyl)-L-phenylalanine ethyl ester
N-(4-benzyl-3-oxomorpholin-5-carbonyl)-L-phenylalanine
N-(4-benzyl-3-oxothiomorpholin-5-carbonyl)-L-4-nitrophenylalanine methyl ester
N-(benzyl)-L-pyroglutamyl-L-4-(pyridin4-ylcarbonylamino)phenylalanine methyl ester
N-(benzyl)-L-pyroglutamyl-L-4-(1'-benzyloxycarbonylpiperidin-4'-ylcarbonylamino)phenylalanine methyl ester
N-(benzyl)-L-pyroglutamyl-L-4(pyridin-4-ylcarbonylamino)phenylalanine
N-(benzyl)-L-pyroglutamyl-L-4-(1'-benzyloxycarbonylpiperidin4'-ylcarbonylamino)phenylalanine
N-(benzyl)-L-pyroglutamyl-L-tyrosine ethyl ester
N-(benzyl)-L-pyroglutamyl-L-4-(piperidin-4'-ylcarbonylamino)phenylalanine
N-(benzyl)-L-pyroglutamyl-L-4-nitrophenylalanine ethyl ester
N-(benzyl)-L-pyroglutamyl-L-tyrosine
N-(benzyl)-L-pyroglutamyl-L-4-(1'-methylpiperidin-4'-yloxy)phenylalanine ethyl ester
N-(benzyl)-L-pyroglutamyl-L-4-nitrophenylalanine
N-(benzyl)-L-pyroglutamyl-L-4-[(4'-methylpiperazin-1'-yl)carbonyloxy]phenylalanine ethyl ester
N-(benzyl)-L-pyroglutamyl-L-4-(1'-methylpiperidin4'-yloxy)phenylalanine
N-(benzyl)-L-pyroglutamyl-L-4-[(4'-methylpiperazin-1'-yl)carbonyloxy]phenylalanine
N-(benzyl)-L-pyroglutamyl-L-4-(N,N-dimethylcarbamyloxy)phenylalanine ethyl ester
N-(benzyl)-L-pyroglutamyl-L-4-aminophenylalanine ethyl ester
N-(benzyl)-L-pyroglutamyl-L-4-(N,N-dimethylcarbamyloxy)phenylalanine
N-(benzyl)-L-pyroglutamyl-L-4-(N,N-dimethylcarbamyloxy)phenylalanine tert-butyl ester
N-(benzyl)-L-pyroglutamyl-L-4-[(4'-methylpiperazin-1'-yl)carbonyloxy]phenylalanine tert-butyl ester
N-(benzyl)-L-pyroglutamyl-L-4-[(thiomorpholin-4'-yl)carbonyloxy]phenylalanine tert-butyl ester
N-(4-fluorobenzyl)-L-pyroglutamyl-L-4-[(thiomorpholin-4'-yl)carbonyloxy]phenylalanine tert-butyl ester
N-(benzyl)-L-pyroglutamyl-L-4-(N,N-dimethylcarbamyloxy)phenylalanine isopropyl ester
N-(4-fluorobenzyl)-L-pyroglutamyl-L-4-(N,N-dimethylcarbamyloxy)phenylalanine tert-butyl ester
N-(benzyl)-L-pyroglutamyl-L-3-chloro-4-hydroxyphenylalanine
N-(4-cyanobenzyl)-L-pyroglutamyl-L-4-(N,N-dimethylcarbamyloxy)phenylalanine tert-butyl ester
N-(benzyl)-L-pyroglutamyl-L-3-chloro-4-(N,N-dimethylcarbamyloxy)phenylalanine methyl ester
N-(4-fluorobenzyl)-L-pyroglutamyl-L-4-[(thiomorpholin-4'-yl)carbonyloxy]phenylalanine
N-(4-cyanobenzyl)-L-pyroglutamyl-L-4-(N,N-dimethylcarbamyloxy)phenylalanine
N-(1-benzyloxycarbonyl-2-imidazolidone-5-carbonyl)-L-4-(N,N-dimethylcarbamyloxy)phenylalanine
N-(4-nitrobenzyl)-L-pyroglutamyl-L-4-(N,N-dimethylcarbamyloxy)phenylalanine tert-butyl ester
N-(benzyl)-L-pyroglutamyl-L-3-chloro-4-(N,N-dimethylcarbamyloxy)phenylalanine
N-(4-fluorobenzyl)-L-pyroglutamyl-L-4-[(4'-(pyridin-2-yl)piperazin-1'-yl)carbonyloxy]phenylalanine
N-(4-fluorobenzyl)-L-pyroglutamyl-L-4-[(4'-(pyridin-2-yl)piperazin-1'-yl)carbonyloxy]phenylalanine tert-butyl ester
N-(4-aminobenzyl)-L-pyroglutamyl-L-4-(N,N-dimethylcarbamyloxy)phenylalanine tert-butyl ester
N-(pyridin-3-ylmethyl)-L-pyroglutamyl-L-tyrosine tert-butyl ester
N-(pyridin-3-ylmethyl)-L-pyroglutamyl-L-4-(N,N-dimethylcarbamyloxy)phenylalanine N-(pyridin-3-ylmethyl)-L-pyroglutamyl-L-4-(N,N-dimethylcarbamyloxy)phenylalanine tert-butyl ester
N-(pyridin-3-ylmethyl)-L-pyroglutamyl-L-4-[(4'-(pyridin-2-yl)piperazin-1'-yl)carbonyloxy]phenylalanine tert-butyl ester
N-(pyridin-3-ylmethyl)-L-pyroglutamyl-L-4-[(4'-(pyridin-2-yl)piperazin-1'-yl)carbonyloxy]phenylalanine
N-(4-benzyl-5-oxo-4-azatricyclo[4.2.1.0 (3,7)]nonane-3-carbonyl)-L-tyrosine tert-butyl ester
N-(4-benzyl-5-oxo-4-azatricyclo[4.2.1.0 (3,7)]nonane-3-carbonyl)-L-4-(N,N-dimethylcarbamyloxy)phenylalanine tert-butyl ester
N-(4-benzyl-5-oxo-4-azatricyclo[4.2.1.0 (3,7)]nonane-3-carbonyl)-L-4-(N,N-dimethylcarbamyloxy)phenylalanine
N-(4-fluorobenzyl)-L-pyroglutamyl-L-4-(N,N-dimethylcarbamyloxy)phenylalanine and pharmaceutically acceptable salts thereof as well as any of the ester compounds recited above wherein one ester is replaced with another ester selected from the group consisting of methyl ester, ethyl ester, n-propyl ester, isopropyl ester, n-butyl ester, isobutyl ester, sec-butyl ester and tert-butyl ester.

This invention also provides methods for binding VLA-4 in a biological sample which method comprises contacting the biological sample with a compound of formula I or IA above under conditions wherein said compound binds to VLA-4.

Certain of the compounds of formula I and IA above are also useful in reducing VLA-4 mediated inflammation in vivo.

This invention also provides pharmaceutical compositions comprising a pharmaceutically acceptable carrier and a therapeutically effective amount of one or more of the compounds of formula I or IA above. Alternatively, racemic mixtures can be used.

The pharmaceutical compositions may be used to treat VLA-4 mediated disease conditions. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Accordingly, this invention also provides methods for the treatment of an inflammatory disease in a patient mediated by VLA-4 which methods comprise administering to the patient the pharmaceutical compositions described above.

Preferred compounds of formula I and IA above include those set forth in Tables IA, IB, IC and ID below:

TABLE IA

| $R^a$ | $R^b$ | $R^c$ |
|---|---|---|
| φ-CH$_2$— | φ-CH$_2$— | —OH |
| φ-CH$_2$—OC(O)— | φ-CH$_2$— | —OH |
| φ-CH$_2$— | 4-[φ-C(O)NH-]-benzyl- | —OH |
| 3,4-dichlorobenzyl- | 4-[φ-C(O)NH-]-benzyl- | —OH |
| 4-chlorobenzyl- | 4-[φ-C(O)NH-]-benzyl- | —OH |
| 3-chlorobenzyl- | 4-[φ-C(O)NH-]-benzyl- | —OCH$_3$ |
| 3-chlorobenzyl- | 4-[φ-C(O)NH-]-benzyl- | —OH |
| 4-chlorobenzyl- | 4-[φ-C(O)NH-]-benzyl- | —OCH$_3$ |
| 4-CH$_3$-benzyl- | 4-[φ-C(O)NH-]-benzyl- | —OCH$_3$ |
| 4-CH$_3$-benzyl- | 4-[φ-C(O)NH-]-benzyl- | —OH |
| 4-CH$_3$O-benzyl- | 4-[φ-C(O)NH-]-benzyl- | —OCH$_3$ |
| 4-CH$_3$O-benzyl- | 4-[φ-C(O)NH-]-benzyl- | —OH |
| 3-chlorobenzyl- | (1-benzylimidazol-4-yl)methyl- | —OH |
| 4-CH$_3$-benzyl- | (1-benzylimidazol-4-yl)methyl- | —OCH$_3$ |
| 4-CH$_3$-benzyl- | (1-benzylimidazol-4-yl)methyl- | —OH |
| φ-CH$_2$— | φ-CH$_2$— | —OH |
| φ-CH$_2$— | 4-[pyridin-4-yl-C(O)NH-]-benzyl- | —OCH$_3$ |
| φ-CH$_2$— | 4-[(1-(benzyloxy-C(O)-)piperidin-4-yl-)C(O)NH-]-benzyl- | —OCH$_3$ |
| φ-CH$_2$— | 4-[(pyridin-4-yl-)C(O)NH-]-benzyl- | —OH |
| φ-CH$_2$— | 4-[(1-(benzyloxy-C(O)-)piperidin-4-yl-)C(O)NH-]-benzyl- | —OH |
| φ-CH$_2$— | 4-hydroxybenzyl- | —OCH$_2$CH$_3$ |
| φ-CH$_2$— | 4-[(piperidin-4-yl-)C(O)NH-]benzyl- | —OH |
| φ-CH$_2$— | 4-NO$_2$-benzyl- | —OCH$_2$CH$_3$ |
| φ-CH$_2$— | 4-hydroxybenzyl- | —OH |
| φ-CH$_2$— | 4-[(1-methylpiperidin-4-yl-)O-]benzyl- | —OCH$_2$CH$_3$ |
| φ-CH$_2$— | 4-NO$_2$-benzyl- | —OH |
| φ-CH$_2$— | 4-[(4-methylpiperazin-1-yl-)C(O)O-]benzyl- | —OCH$_2$CH$_3$ |
| φ-CH$_2$— | 4-[(1-methylpiperidin-4-yl-)O-)benzyl- | —OH |
| φ-CH$_2$— | 4-[(4-methylpiperazin-1-yl-)C(O)O-]benzyl- | —OH |
| φ-CH$_2$— | 4-[(CH$_3$)$_2$NC(O)O-]benzyl- | —OCH$_2$CH$_3$ |
| φ-CH$_2$— | 4-NH$_2$-benzyl- | —OCH$_2$CH$_3$ |
| φ-CH$_2$— | 4-[(CH$_3$)$_2$NC(O)O-]benzyl- | —OH |
| φ-CH$_2$— | 4-[(CH$_3$)$_2$NC(O)O-]benzyl- | —OC(CH$_3$)$_3$ |

TABLE IA-continued

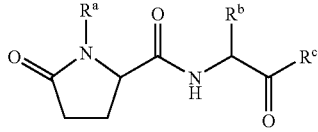

| Rᵃ | Rᵇ | Rᶜ |
|---|---|---|
| φ-CH₂— | 4-[(4-methylpiperazin-1-yl-)C(O)O-]benzyl- | —OC(CH₃)₃ |
| φ-CH₂— | 4-[thiomorpholin-4-yl-C(O)O-]benzyl- | —OC(CH₃)₃ |
| 4-fluoro-benzyl- | 4-[thiomorpholin-4-yl-C(O)O-]benzyl- | —OC(CH₃)₃ |
| φ-CH₂— | 4-[(CH₂)₃NC(O)O-]benzyl- | —OCH(CH₃)₂ |
| 4-fluoro-benzyl- | 4-[(CH₂)₃NC(O)O-]benzyl- | —OC(CH₃)₃ |
| φ-CH₂— | 3-chloro-4-hydroxybenzyl- | —OCH₃ |
| 4-cyano-benzyl- | 4-[(CH₂)₃NC(O)O-]benzyl- | —OC(CH₃)₃ |
| φ-CH₂— | 3-chloro-4-[(CH₂)₃NC(O)O-]benzyl- | —OCH₃ |
| 4-fluoro-benzyl- | 4-[(CH₂)₃NC(O)O-]benzyl- | —OH |
| 4-fluoro-benzyl- | 4-[thiomorpholin-4-yl-C(O)O-]benzyl- | —OH |
| 4-cyano-benzyl- | 4-[(CH₂)₃NC(O)O-]benzyl- | —OH |
| 4-NO₂-benzyl- | 4-[(CH₂)₃NC(O)O-]benzyl- | —OC(CH₃)₃ |
| φ-CH₂— | 3-chloro-4-[(CH₂)₃NC(O)O-]benzyl- | —OH |
| 4-fluoro-benzyl- | 4-[4-(pyridin-2-yl)piperazin-1-yl-C(O)O-]benzyl- | —OH |
| 4-fluoro-benzyl- | 4-[4-(pyridin-2-yl)piperazin-1-yl-C(O)O-]benzyl- | —OC(CH₃)₃ |
| 4-NH₂benzyl- | 4-[(CH₂)₃NC(O)O-]benzyl- | —OC(CH₃)₃ |
| pyridin-3-CH₂— | 4-[(CH₂)₃NC(O)O-]benzyl- | —OH |
| pyridin-3-CH₂— | 4-[4-(pyridin-2-yl)piperazin-1-yl-C(O)O-]benzyl- | —OC(CH₃)₃ |
| pyridin-3-CH₂— | 4-[4-(pyridin-2-yl)piperazin-1-yl-C(O)O-]benzyl- | —OH |

TABLE 1B

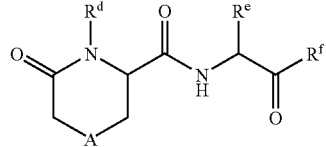

| Rᵈ | Rᵉ | Rᶠ | A |
|---|---|---|---|
| φ-CH₂— | φ-CH₂— | —OH | S |
| φ-CH₂— | φ-CH₂— | —OCH₂CH₃ | S |
| φ-CH₂— | φ-CH₂— | —OH | O |
| φ-CH₂— | 4-NO₂-benzyl- | —OCH₃ | S |

TABLE IC

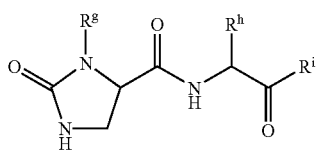

| Rᵍ | Rʰ | Rⁱ |
|---|---|---|
| φ-CH₂—OC(O)— | 4-[(CH₂)₃NC(O)O-]benzyl- | —OH |

TABLE ID

| Rʲ | Rᵏ | Rˡ |
|---|---|---|
| φ-CH₂— | 4-hydroxybenzyl- | —OC(CH₃)₃ |
| φ-CH₂— | 4-[(CH₂)₃NC(O)O-]benzyl- | —OC(CH₃)₃ |
| φ-CH₂— | 4-[(CH₂)₃NC(O)O-]benzyl- | —OH |

DETAILED DESCRIPTION OF THE INVENTION

As above, this invention relates to compounds which inhibit leukocyte adhesion and, in particular, leukocyte adhesion mediated by VLA-4. However, prior to describing this invention in further detail, the following terms will first be defined.

Definitions

As used herein, "alkyl" refers to alkyl groups preferably having from 1 to 10 carbon atoms and more preferably 1 to 6 carbon atoms. This term is exemplified by groups such as methyl, t-butyl, n-heptyl, octyl and the like.

"Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkylene" refers to a divalent hydrocarbon radical of the formula —(CH$_2$)$_n$— where n is an integer ranging from 1 to 10. By way of illustration, the term alkylene includes methylene (—CH$_2$—), ethylene (—CH$_2$CH$_2$—), propylene (—CH$_2$CH$_2$CH$_2$—) and the like.

"Substituted alkylene" refers to an alkylene group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl. Additionally, two or more substituents on the substituted alkylene group may also be joined together to form a fused and/or bridged cycloalkyl, substituted cycloalkyl, heterocyclic or substituted heterocyclic group, or a fused aryl or heteroaryl group.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Alkoxycarbonyl" refers to the group "alkyl-O—C(O)—".

"Substituted alkoxycarbonyl" refers to the group "substituted alkyl-O—C(O)—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1–2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkynyl" refers to alkynyl group preferably having from 2 to 10 carbon atoms and more preferably 3 to 6 carbon atoms and having at least 1 and preferably from 1–2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted-heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2$NRR where R is hydrogen or alkyl.

"Amidino" refers to the group $H_2NC(=NH)$—and the term "alkylamidino" refers to compounds having 1 to 3 alkyl groups (e.g., alkyl-HNC(=NH)— and the like).

"Thioamidino" refers to the group RSC(=NH)—where R is hydrogen or alkyl.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)$NH_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom, a heterocyclic or substituted heterocyclic ring, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)$NH_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom, a heterocyclic or substituted heterocyclic ring, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

Substituted aryl refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$-NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with -SO$_2$NRR where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"4-Benzyl-5-oxo-4-azatricyclo[4.2.1.0 (3,7)]nonane-3-carboxylic acid" refers to a compound of the formula:

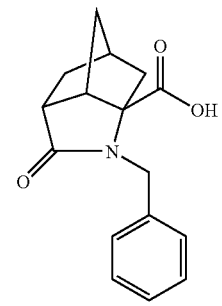

"Cycloalkyl" refers to cyclic alkyl groups of from 3 to 8 carbon atoms having a single cyclic ring including, by way of example, cyclopropyl, cyclobutyl, cyclopentyl, cyclooctyl and the like. Excluded from this definition are multi-ring or fused-ring alkyl groups such as adamantanyl, and the like.

"Cycloalkenyl" refers to cyclic alkenyl groups of from 3 to 8 carbon atoms having single or multiple unsaturation but which are not aromatic.

"Substituted cycloalkyl" and "substituted cycloalkenyl" refer to a cycloalkyl and cycloalkenyl groups, preferably of from 3 to 8 carbon atoms, having from 1 to 5 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS-(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$-NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkoxy" refers to —O-cycloalkyl groups.

"Substituted cycloalkoxy" refers to —O-substituted cycloalkyl groups.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroalkylene" refers to an alkylene group in which from 1 to 5, preferable from 1 to 3, of the carbon atoms in the alkylene chain have been replaced with a hetereoatom selected from nitrogen, oxygen or sulfur. By way of illustration, the term heteroalkylene includes —CH$_2$—O—CH$_2$—, —CH$_2$—S—CH$_2$—, —NHCH$_2$— and the like.

"Substituted heteroalkylene" refers to a heteroalkylene group having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Heteroaryl" refers to an aromatic carbocyclic group of from 2 to 10 carbon atoms and 1 to 4 heteroatoms selected from oxygen, nitrogen and sulfur within the ring. Such heteroaryl groups can have a single ring (e.g., pyridyl or furyl) or multiple condensed rings (e.g., indiolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S-(O)$_2$-substituted heteroaryl, —S(°)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS-(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from nitrogen, sulfur or oxygen within the ring wherein, in fused ring systems, one or more of the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS-(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine; naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"L-Pyroglutamic acid" refers to (S)-(−)-2-pyrrolidone-5-carboxylic acid.

"Thiol" refers to the group —SH.

"Thioalkyl" refers to the groups —S-alkyl

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In a preferred method of synthesis, the compounds of formula I and IA are prepared by first alkylating a cyclic compound of formula II:

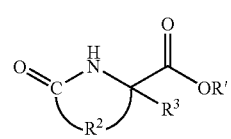

II wherein R' is alkyl, such as methyl, ethyl and the like, and R² and R³ are as defined herein, with a suitable alkylating agent to provide an N-alkylated compound of formula III:

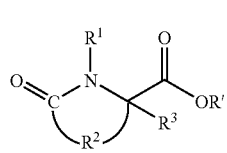

III wherein R' and R¹–R³ are as defined herein.

This reaction is typically conducted by contacting the cyclic compound of formula II with at least one equivalent of a strong base, such as potassium tert-butoxide, in the presence of at least one equivalent of the alkylating agent. Generally, the reaction is conducted in an inert diluent, such as THF and the like, at a temperature ranging from about 0° C. to about 40° C. for about 1 to about 24 hours. Upon completion of the reaction, the resulting N-alkylated compound III is recovered by conventional methods including neutralization, extraction, precipitation, chromatography, filtration, and the like.

The cyclic compounds of formula II employed in the above reaction are either known compounds or compounds that can be prepared from known compounds by conventional synthetic procedures. Examples of suitable compounds for use in this reaction include, but are not limited to, L-pyroglutamic acid esters, D-pyroglutamic acid esters, D,L-pyroglutamic acid esters, 3-oxomorpholine-5-carboxylic acid esters, 3-oxothiomorpholine-5-carboxylic acid esters, 5-oxo-4-azatricyclo[4.2.1.0 (3,7]nonane-3-carboxylic acid esters and the like.

Any suitable alkylating agent may be employed in this reaction. Preferred alkylating agents included benzyl halides, such as benzyl bromide and benzyl chlorides. Particularly preferred alkylating agents include benzyl bromide, 3-chlorobenzyl bromide, 4-chlorobenzyl bromide, 3,4-dichlorobenzyl bromide, 4-methylbenzyl bromide, 4-methoxybenzyl bromide, 4-fluorobenzyl bromide, 4-cyanobenzyl bromide, 4-nitrobenzyl bromide and the like.

After completion of the alkylation reaction, subsequent hydrolysis of the ester group using conventional reagents and conditions, i.e., treatment with an alkali metal hydroxide in an inert diluent such as methanol/water, then affords the corresponding carboxylic acid of formula IV:

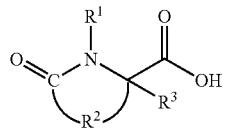

IV wherein $R^1$–$R^3$ are as defined herein.

Alternatively, intermediate IV can be prepared by reductive alkylation of an amino dicarboxylic acid derivative of formula IVa:

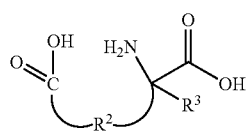

IVa where $R^2$ and $R^3$ are as defined herein, with an aldehyde of the formula: $R^1$—CHO, where $R^1$ is as defined herein, using conventional reductive alkylation conditions and reagents, followed by cyclization of the resulting N-alkylated intermediate. The reductive alkylation reaction is typically conducted by contacting the amino compound IVa with at least one equivalent, preferably about 1.1 to about 1.5 equivalents, of an aldehyde and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 hours. The resulting N-alkylated intermediate is then cyclized by acidification and heating to afford intermediate IV. This reaction typically affords products of high optical purity when an optically active amino dicarboxylic acid, such as L-glutamic acid, is employed.

The compounds of formula I are then prepared by coupling the intermediate of formula IV with an amino acid derivative of formula V:

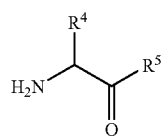

V wherein $R^4$ and $R^5$ are as defined herein.

This coupling reaction is typically conducted using well-known coupling reagents such as carbodiimides, BOP reagent (benzotriazol-1-yloxy-tris(dimethylamino) phosphonium hexafluorophosphonate) and the like. Suitable carbodiimides include, by way of example, dicyclohexylcarbodiimide (DCC), 1-(3-dimethylaminopropyl)-3-ethylcarbodiimide (EDC) and the like. If desired, polymer supported forms of carbodiimide coupling reagents may also be used including, for example, those described in *Tetrahedron Letters*, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting intermediate IV with about 1 to about 2 equivalents of the coupling reagent and at least one equivalent, preferably about 1 to about 1.2 equivalents, of amino acid derivative V in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the compound of formula IA is recovered by conventional methods including neutralization, extraction, precipitation, chromatography, filtration, and the like.

Alternatively, the intermediate IV can be converted into an acid halide and the acid halide coupled with amino acid derivative V to provide compounds of formula IA. The acid halide of IV can be prepared by contacting IV with an inorganic acid halide, such as thionyl chloride, phosphorous trichloride, phosphorous tribromide or phosphorous pentachloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 hours. A catalyst, such as N,N-dimethylformamide, may also be used in this reaction.

The acid halide of intermediate IV is then contacted with at least one equivalent, preferably about 1.1 to about 1.5 equivalents, of amino acid derivative V in an inert diluent, such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under-Schotten-Baumann-type conditions using aqueous alkali, such as sodium hydroxide and the like. Upon completion of the reaction, the compound of formula IA is recovered by conventional methods including neutralization, extraction, precipitation, chromatography, filtration, and the like.

The amino acid derivatives of formula V employed in the above reactions are either known compounds or compounds that can be prepared from known compounds by conventional synthetic procedures. For example, amino acid derivatives of formula V can be prepared by C-alkylating commercially available diethyl 2-acetamidomalonate (Aldrich, Milwaukee, Wis., USA) with an alkyl or substituted alkyl halide. This reaction is typically conducted by treating the diethyl 2-acetamidomalonate with at least one equivalent of sodium ethoxide and at least one equivalent of an alkyl or substituted alkyl halide in refluxing ethanol for about 6 to about 12 hours. The resulting C-alkylated malonate is then deacetylated, hydrolyzed and decarboxylated by heating in aqueous hydrochloric acid at reflux for about 6 to about 12 hours to provide the amino acid, typically as the hydrochloride salt.

Examples of amino acid derivatives of formula V suitable for use in the above reactions include, but are not limited to, L-alanine methyl ester, L-isoleucine methyl ester, L-leucine methyl ester, L-valine methyl ester, β-tert-butyl-L-aspartic acid methyl ester, L-asparagine tert-butyl ester, ε-Boc-L-lysine methyl ester, ε-Cbz-L-lysine methyl ester, γ-tert-butyl-L-glutamic acid methyl ester, L-glutamine tert-butyl ester, L-(N-methyl)histidine methyl ester, L-(N-benzyl) histidine methyl ester, L-methionine methyl ester, L-(O-benzyl)serine methyl ester, L-tryptophan methyl ester, L-phenylalanine methyl ester, L-phenylalanine isopropyl ester, L-phenylalanine benzyl ester, L-phenylalaninamide, N-methyl-L-phenylalanine benzyl ester, 3-carboxy-D,L-phenylalanine methyl ester, 4-carboxy-D,L-phenylalanine methyl ester, L-4-chlorophenylalanine methyl ester, L-4-(3-dimethylaminopropyloxy)phenylalanine methyl ester, L-4-iodophenylalanine methyl ester, L-3,4-methylenedioxyphenylalanine methyl ester, L-3,4-ethylenedioxyphenylalanine methyl ester, L-4-nitrophenylalanine methyl ester, L-tyrosine methyl ester, D,L-homophenylalanine methyl ester, L-(O-methyl)tyrosine methyl ester, L-(O-tert-butyl)tyrosine methyl ester, L-(O-benzyl)tyrosine methyl ester, L-3,5-diiodotyrosine methyl ester, L-3-iodotyrosine methyl ester, β-(1-naphthyl)-L-alanine methyl ester, β-(2-naphthyl)-L-alanine methyl ester, β-(2-thienyl)-L-alanine methyl ester, β-cyclohexyl-L-alanine methyl ester, β-(2-pyridyl)-L-alanine methyl ester, β-(3-pyridyl)-L-alanine methyl ester, β-(4-pyridyl)-L-alanine methyl ester, β-(2-thiazolyl)-D,L-alanine methyl ester, β-(1,2,4-triazol-3-yl)-D,L-alanine methyl ester, and the like. If desired, of course, other esters or amides of the above-described compounds may also be employed.

For ease of synthesis, the compounds of formula I are typically prepared as an ester, i.e., where $R^5$ is an alkoxy or substituted alkoxy group and the like. If desired, the ester group can be hydrolysed using conventional conditions and reagents to provide the corresponding carboxylic acid. Typically, this reaction is conducted by treating the ester with at least one equivalent of an alkali metal hydroxide, such as lithium, sodium or potassium hydroxide, in an inert diluent, such as methanol or mixtures of methanol and water, at a temperature ranging about 0° C. to about 24° C. for about 1 to about 12 hours. Alternatively, benzyl esters may be removed by hydrogenolysis using a palladium catalyst, such as palladium on carbon, or tert-butyl esters can be hydrolyzed by exposure to strong acids, such as formic acid or trifluoroacetic acid. The resulting carboxylic acids may be coupled, if desired, to amines such as β-alanine ethyl ester, hydroxyamines such as hydroxylamine and N-hydroxysuccinimide, alkoxyamines and substituted alkoxyamines such as O-methylhydroxylamine and O-benzylhydroxylamine, and the like, using conventional coupling reagents and conditions as described above.

As will be apparent to those skilled in the art, other functional groups present on any of the substituents of the compounds of formula I can be readily modified or derivatized either before or after the above-described coupling reactions using well-known synthetic procedures. For example, a nitro group present on a substituent of a compound of formula I or an intermediate thereof may be readily reduced by hydrogenation in the presence of a palladium catalyst, such as palladium on carbon, to provide the corresponding amino group. This reaction is typically conducted at a temperature of from about 20° C. to about 50° C. for about 6 to about 24 hours in an inert diluent, such as methanol. Compounds having a nitro group on the $R^4$ substituent can be prepared, for example, by using a 4-nitrophenylalanine derivative and the like in the above-described coupling reactions.

Similarly, a pyridyl group can be hydrogenated in the presence of a platinum catalyst, such as platinum oxide, in an acidic diluent to provide the corresponding piperidinyl analogue. Generally, this reaction is conducted by treating the pyridine compound with hydrogen at a pressure ranging from about 20 psi to about 60 psi, preferably about 40 psi, in the presence of the catalyst at a temperature of about 20° C. to about 50° C. for about 2 to about 24 hours in an acidic diluent, such as a mixture of methanol and aqueous hydrochloric acid. Compounds having a pyridyl group can be readily prepared by using, for example, β-(2-pyridyl)-, β-(3-pyridyl)- or β-(4-pyridyl)-L-alanine derivatives in the above-described coupling reactions.

Additionally, when the $R^4$ substituent of a compound of formula I or an intermediate thereof contains a primary or secondary amino group, such amino groups can be further derivatized either before or after the above coupling reactions to provide, by way of example, amides, sulfonamides, ureas, thioureas, carbamates, secondary or tertiary amines and the like. Compounds having a primary amino group on the $R^4$ substituent may be prepared, for example, by reduction of the corresponding nitro compound as described above. Alternatively, such compounds can be prepared by using an amino acid derivative of formula VI derived from lysine, 4-aminophenylalanine and the like in the above-described coupling reactions.

By way of illustration, a compound of formula I or an intermediate thereof having a substituent containing a primary or secondary amino group, such as where $R^4$ is a (4-aminophenyl)methyl group, can be readily N-acylated using conventional acylating reagents and conditions to provide the corresponding amide. This acylation reaction is typically conducted by treating the amino compound with at least one equivalent, preferably about 1.1 to about 1.2 equivalents, of a carboxylic acid in the presence of a coupling reagent such as a carbodiimide, BOP reagent (benzotriazol-1-yloxy-tris(dimethylamino)phosphonium hexafluorophosphonate) and the like, in an inert diluent, such as dichloromethane,- chloroform, acetonitrile, tetrahydrofuran, N,N-dimethylformamide and the like, at a temperature ranging from about 0° C. to about 37° C. for about 4 to about 24 hours. Preferably, a promoter, such as N-hydroxysuccinimide, 1-hydroxy-benzotriazole and the like, is used to facilitate the acylation reaction. Examples of carboxylic acids suitable for use in this reaction include, but are not limited to, N-tert-butyloxycarbonylglycine, N-tert-butyloxycarbonyl-L-phenylalanine, N-tert-butyloxycarbonyl-L-aspartic acid benzyl ester, benzoic acid, N-tert-butyloxycarbonylisonipecotic acid, N-methylisonipecotic acid, N-tert-butyloxycarbonylnipecotic acid, N-tert-butyloxycarbonyl-L-tetrahydroisoquinoline-3-carboxylic acid, N-(toluene-4-sulfonyl)-L-proline and the like.

Alternatively, a compound of formula I or an intermediate thereof containing a primary or secondary amino group can be N-acylated using an acyl halide or a carboxylic acid anhydride to form the corresponding amide. This reaction is typically conducted by contacting the amino compound with at least one equivalent, preferably about 1.1 to about 1.2 equivalents, of the acyl halide or carboxylic acid anhydride in an inert diluent, such as dichloromethane, at a temperature ranging from about of about –70° C. to about 40° C. for about 1 to about 24 hours. If desired, an acylation catalyst such as 4-(N,N-dimethylamino)pyridine may be used to promote the acylation reaction. The acylation reaction is preferably conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like.

Examples of acyl halides and carboxylic acid anhydrides suitable for use in this reaction include, but are not limited to, 2-methylpropionyl chloride, trimethylacetyl chloride, phenylacetyl chloride, benzoyl chloride, 2-bromobenzoyl chloride, 2-methylbenzoyl chloride, 2-trifluoromethylbenzoyl chloride, isonicotinoyl chloride, nicotinoyl chloride, picolinoyl chloride, acetic anhydride, succinic anhydride, and the like. Carbamyl chlorides, such as N,N-dimethylcarbamyl chloride, N,N-diethylcarbamyl chloride and the like, can also be used in this reaction to provide ureas. Similarly, dicarbonates, such as di-tert-butyl dicarbonate, may be employed to provide carbamates.

In a similar manner, a compound of formula I or an intermediate thereof containing a primary or secondary amino group may be N-sulfonated to form a sulfonamide using a sulfonyl halide or a sulfonic acid anhydride. Sulfonyl halides and sulfonic acid anhydrides suitable for use in this reaction include, but are not limited to, methanesulfonyl chloride, chloromethanesulfonyl chloride, p-toluenesulfonyl chloride, trifluoromethanesulfonic anhydride, and the like. Similarly, sulfamoyl chlorides, such as dimethylsulfamoyl chloride, can be used to provide sulfamides (e.g., >N—SO$_2$—N <).

Additionally, a primary and secondary amino group present on a substituent of a compound of formula I or an intermediate thereof can be reacted with an isocyanate or a thioisocyanate to give a urea or thiourea, respectively. This reaction is typically conducted by contacting the amino compound with at least one equivalent, preferably about 1.1 to about 1.2 equivalents, of the isocyanate or thioisocyanate in an inert diluent, such as toluene and the like, at a temperature ranging from about 24° C. to about 37° C. for about 12 to about 24 hours. The isocyanates and thioisocyanates used in this reaction are commercially available or can be prepared from commercially available compounds using well-known synthetic procedures. For example, isocyanates and thioisocyanates are readily prepared by reacting the appropriate amine with phosgene or thiophosgene. Examples of isocyanates and thioisocyanates suitable for use in this reaction include, but are not limited to, ethyl isocyanate, n-propyl isocyanate, 4-cyanophenyl isocyanate, 3-methoxyphenyl isocyanate, 2-phenylethyl isocyanate, methyl thioisocyanate, ethyl thioisocyanate, 2-phenylethyl thioisocyanate, 3-phenylpropyl thioisocyanate, 3-(N,N-diethylamino)propyl thioisocyanate, phenyl thioisocyanate, benzyl thioisocyanate, 3-pyridyl thioisocyanate, fluorescein isothiocyanate (isomer I) and the like.

Furthermore, when a compound of formula I or an intermediate thereof contains a primary or secondary amino group, the amino group can be reductively alkylated using aldehydes or ketones to form a secondary or tertiary amino group. This reaction is typically conducted by contacting the amino compound with at least one equivalent, preferably about 1.1 to about 1.5 equivalents, of an aldehyde or ketone and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 hours. Aldehydes and ketones suitable for use in this reaction include, by way of example, benzaldehyde, 4-chlorobenzaldehyde, valeraldehyde and the like.

In a similar manner, when a compound of formula I or an intermediate thereof has a substituent containing a hydroxyl group, the hydroxyl group can be further modified or derivatized either before or after the above coupling reactions to provide, by way of example, ethers, carbamates and the like. Compounds having a hydroxyl group on the $R^4$ substituent, for example, can be prepared using an amino acid derivative of formula V derived from tyrosine and the like in the above-described reactions.

By way of example, a compound of formula I or an intermediate thereof having a substituent containing a hydroxyl group, such as where $R^4$ is a (4-hydroxyphenyl) methyl group, can be readily O-alkylated to form ethers. This O-alkylation reaction is typically conducted by contacting the hydroxy compound with a suitable alkali or alkaline earth metal base, such as potassium carbonate, in an inert diluent, such as acetone, 2-butanone and the like, to form the alkali or alkaline earth metal salt of the hydroxyl group. This salt is generally not isolated, but is reacted in situ with at least one equivalent of an alkyl or substituted alkyl halide or sulfonate, such as an alkyl chloride, bromide, iodide, mesylate or tosylate, to afford the ether. Generally, this reaction is conducted at a temperature ranging from about 60° C. to about 150° C. for about 24 to about 72 hours. Preferably, a catalytic amount of sodium or potassium iodide is added to the reaction mixture when an alkyl chloride or bromide is employed in the reaction.

Examples of alkyl or substituted alkyl halides and sulfonates suitable for use in this reaction include, but are not limited to, tert-butyl bromoacetate, N-tert-butyl chloroacetamide, 1-bromoethylbenzene, ethyl α-bromophenylacetate, 2-(N-ethyl-N-phenylamino)ethyl chloride, 2-(N,N-ethylamino)ethyl chloride, 2-(N,N-diisopropylamino)ethyl chloride, 2-(N,N-dibenzylamino) ethyl chloride, 3-(N,N-ethylamino)propyl chloride, 3-(N-benzyl-N-methylamino)propyl chloride, N-(2-chloroethyl) morpholine, 2-(hexamethyleneimino)ethyl chloride, 3-(N-methylpiperazine)propyl chloride, 1-(3-chlorophenyl)-4-(3-chloropropyl)piperazine, 2-(4-hydroxy-4-phenylpiperidine) ethyl chloride, N-tert-butyloxycarbonyl-3-piperidinemethyl tosylate, and the like.

Alternatively, a hydroxyl group present on a substituent of a compound of formula I or an intermediate thereof can be O-alkylating using the Mitsunobu reaction. In this reaction, an alcohol, such as 3-(N,N-dimethylamino)-1-propanol and the like, is reacted with about 1.0 to about 1.3 equivalents of triphenylphosphine and about 1.0 to about 1.3 equivalents of diethyl azodicarboxylate in an inert diluent, such as tetrahydrofuran, at a temperature ranging from about −10° C. to about 5° C. for about 0.25 to about 1 hour. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 hours to provide the O-alkylated product.

In a similar manner, a compound of formula I or an intermediate thereof containing an aryl hydroxy group can be reacted with an aryl iodide to provide a diaryl ether. Generally, this reaction is conducted by forming the alkali metal salt of the hydroxyl group using a suitable base, such as sodium hydride, in an inert diluent such as xylenes at a temperature of about −25° C. to about 10° C. The salt is then treated with about 1.1 to about 1.5 equivalents of cuprous bromide dimethyl sulfide complex at a temperature ranging from about 10° C. to about 30° C. for about 0.5 to about 2.0 hours, followed by about 1.1 to about 1.5 equivalents of an aryl iodide, such as sodium 2-iodobenzoate and the like. The reaction is then heated to about 70° C. to about 150° C. for about 2 to about 24 hours to provide the diaryl ether.

Additionally, a hydroxy-containing compound can also be readily derivatized to form a carbamate. In one method for preparing such carbamates, a hydroxy compound of formula I or an intermediate thereof is contacted with about 1.0 to about 1.2 equivalents of 4-nitrophenyl chloroformate in an inert diluent, such as dichloromethane, at a temperature ranging from about −25° C. to about 0° C. for about 0.5 to about 2.0 hours. Treatment of the resulting carbonate with an excess, preferably about 2 to about 5 equivalents, of a trialkylamine, such as triethylamine, for about 0.5 to 2 hours, followed by about 1.0 to about 1.5 equivalents of a primary or secondary amine provides the carbamate. Examples of amines suitable for using in this reaction include, but are not limited to, piperazine, 1-methylpiperazine, 1-acetylpiperazine, morpholine, thiomorpholine, pyrrolidine, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging from about 25° C. to about 70° C. for about 2 to about 72 hours. Typically, this reaction is conducted in the presence of a suitable base to scavenge the acid generated during the reaction. Suitable bases include, by way of example, tertiary amines, such as triethylamine, diisopropylethylamine, N-methylmorpholine and the like. Additionally, at least one equivalent (based on the hydroxy compound) of 4-(N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of formula I or an intermediate thereof contains a primary or secondary hydroxyl group, such hydroxyl groups can be readily converted into a leaving group and displaced to form, for example, amines, sulfides and fluorides. For example, derivatives of 4-hydroxy-L-proline can be converted into the corresponding 4-amino, 4-thio or 4-fluoro-L-proline derivatives via nucleophilic displacement of the derivatized hydroxyl group. Generally, when a chiral compound is employed in these reactions, the stereochemistry at the carbon atom attached to the derivatized hydroxyl group is typically inverted.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of from about 0° C. to about 70° C. for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging from about 0° C. to about 37° C. for about 1 to about 12 hours to provide the corresponding azido compound. The azido group can then be reduced by, for example, hydrogenation using a palladium on carbon catalyst to provide the amino ($-NH_2$) compound.

Similarly, a tosylate group can be readily displaced by a thiol to form a sulfide. This reaction is typically conducted by contacting the tosylate with at least one equivalent of a thiol, such as thiophenol, in the presence of a suitable base, such as 1,8-diazabicyclo[5.4.0]undec-7-ene (DBU), in an inert diluent, such as N,N-dimethylformamide, at a temperature of from about 0° C. to about 37° C. for about 1 to about 12 hours to provide the sulfide. Additionally, treatment of a tosylate with morpholinosulfur trifluoride in an inert diluent, such as dichloromethane, at a temperature ranging from about 0° C. to about 37° C. for about 12 to about 24 hours affords the corresponding fluoro compound.

Furthermore, a compound of formula I or an intermediate thereof having a substituent containing an iodoaryl group, for example, when $R^4$ is a (4-iodophenyl)methyl group, can be readily converted either before or after the above coupling reactions into a biaryl compound. Typically, this reaction is conducted by treating the iodoaryl compound with about 1.1 to about 2 equivalents of an arylzinc iodide, such as 2-(methoxycarbonyl)phenylzinc iodide, in the presence of a palladium catalyst, such as palladium tetra (triphenylphosphine), in an inert diluent, such as tetrahydrofuran, at a temperature ranging from about 24° C. to about 30° C. until reaction completion. This reaction is further described, for example, in Rieke, J. Org. Chem. 1991, 56, 1445.

In some cases, the compounds of formula I or intermediates thereof may contain substituents having one or more sulfur atoms. Such sulfur atoms will be present, for example, when the cyclic compound of formula II employed in the above reactions is derived from 3-oxothiomorpholine-5-carboxylic acid and the like. When present, such sulfur atoms can be oxidized either before or after the above coupling reactions to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. The oxidation reaction is typically conducted by contacting the sulfide compound with about 0.95 to about 1.1 equivalents of the oxidizing reagent in an inert diluent, such as dichloromethane, at a temperature-ranging from about –50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, "*Advanced Organic Chemistry*", 4th Ed., pp. 1201–1202, Wiley Publisher, 1992.

Lastly, the compounds of formula I where W is sulfur can prepared by using an thiocarbonyl derivative in place of compound II in the above described synthetic procedures. Such thiocarbonyl derivatives can be prepared using, for example, Lawesson's reagent under conventional reaction conditions.

Other procedures and reaction conditions for preparing the compounds of this invention are described in the examples set forth below.

Pharmaceutical Formulations

When employed as pharmaceuticals, the compounds of formula I and IA are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I and IA above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
|---|---|
| Active Ingredient | 250.0 mg |
| Isotonic saline | 1000 ml |

Formulation Example 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

The compounds of this invention can be employed to bind VLA-4 ($\alpha_4\beta_1$ integrin) in biological samples and, accordingly have utility in, for example, assaying such samples for VLA-4. In such assays, the compounds can be bound to a solid support and the VLA-4 sample added thereto. The amount of VLA-4 in the sample can be determined by conventional methods such as use of a sandwich ELISA assay. Alternatively, labeled VLA-4 can be used in a competitive assay to measure for the presence of VLA-4 in the sample. Other suitable assays are well known in the art.

In addition, certain of the compounds of this invention inhibit, in vivo, adhesion of leukocytes to endothelial cells mediated by VLA-4 and, accordingly, can be used in the treatment of diseases mediated by VLA-4. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

The biological activity of the compounds identified above may be assayed in a variety of systems. For example, a compound can be immobilized on a solid surface and adhesion of cells expressing VLA-4 can be measured. Using such formats, large numbers of compounds can be screened. Cells suitable for this assay include any leukocytes known to express VLA-4 such as T cells, B cells, monocytes, eosinophils, and basophils. A number of leukocyte cell lines can also be used, examples include Jurkat and U937.

The test compounds can also be tested for the ability to competitively inhibit binding between VLA-4 and VCAM-1, or between VLA-4 and a labeled compound known to bind VLA-4 such as a compound of this invention or antibodies to VLA-4. In these assays, the VCAM-1 can be immobilized on a solid surface. VCAM-1 may also be expressed as a recombinant fusion protein having an Ig tail (e.g., IgG) so that binding to VLA-4 may be detected in an immunoassay. Alternatively, VCAM-1 expressing cells, such as activated endothelial cells or VCAM-1 transfected fibroblasts can be used. For assays to measure the ability to block adhesion to brain endothelial cells, the assays described in International Patent Application Publication No. WO 91/05038 are particularly preferred. This application is incorporated herein by reference in its entirety.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3$H, $^{125}$I, $^{35}$S, $^{14}$C, or $^{32}$P labelled compounds or the like. Non-radioactive labels include ligands which bind to labelled antibodies, fluorophores, chemiluminescent agents, enzymes and antibodies which can serve as specific binding pair members for a labelled ligand. The choice of label depends on sensitivity required, ease of conjugation with the compound, stability requirements, and available instrumentation.

Appropriate in vivo models for demonstrating efficacy in treating inflammatory responses include EAE (experimental autoimmune encephalomyelitis) in mice, rats, guinea pigs or primates, as well as other inflammatory models dependent upon $\alpha 4$ integrins.

Compounds having the desired biological activity may be modified as necessary to provide desired properties such as improved pharmacological properties (e.g., in vivo stability, bio-availability), or the ability to be detected in diagnostic applications. For instance, inclusion of one or more D-amino acids in the sulfonamides of this invention typically increases in vivo stability. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83–93).

For diagnostic purposes, a wide variety of labels may be linked to the compounds, which may provide, directly or indirectly, a detectable signal. Thus, the compounds of the subject invention may be modified in a variety of ways for a variety of end purposes while still retaining biological activity. In addition, various reactive sites may be introduced at the terminus for linking to particles, solid substrates, macromolecules, or the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

In vitro uses include diagnostic applications such as monitoring inflammatory responses by detecting the presence of leukocytes expressing VLA-4. The compounds of this invention can also be used for isolating or labeling such cells. In addition, as mentioned above, the compounds of the invention can be used to assay for potential inhibitors of VLA-4/VCAM-1 interactions.

For in vivo diagnostic imaging to identify, e.g., sites of inflammation, radioisotopes are typically used in accordance with well known techniques. The radioisotopes may be bound to the peptide either directly or indirectly using intermediate functional groups. For instance, chelating agents such as diethylenetriaminepentacetic acid (DTPA) and ethylenediaminetetraacetic acid (EDTA) and similar molecules have been used to bind proteins to metallic ion radioisotopes.

The complexes can also be labeled with a paramagnetic isotope for purposes of in vivo diagnosis, as in magnetic resonance imaging (MRI) or electron spin resonance (ESR), both of which are well known. In general, any conventional method for visualizing diagnostic imaging can be used. Usually gamma- and positron-emitting radioisotopes are used for camera imaging and paramagnetic isotopes are used for MRI. Thus, the compounds can be used to monitor the course of amelioration of an inflammatory response in an individual. By measuring the increase or decrease in lymphocytes expressing VLA-4 it is possible to determine whether a particular therapeutic regimen aimed at ameliorating the disease is effective.

The pharmaceutical compositions of the present invention can be used to block or inhibit cellular adhesion associated with a number of diseases and disorders. For instance, a number of inflammatory disorders are associated with integrins or leukocytes. Treatable disorders include, e.g., transplantation rejection (e.g., allograft rejection), Alzheimer's disease, atherosclerosis, AIDS dementia, diabetes (including acute juvenile onset diabetes), retinitis, cancer metastases, rheumatoid arthritis, acute leukocyte-mediated lung injury (e.g., adult respiratory distress syndrome), asthma, nephritis, and acute and chronic inflammation, including atopic dermatitis, psoriasis, myocardial ischemia, and inflammatory bowel disease, (including Crohn's disease and ulcerative colitis). In preferred embodiments the pharmaceutical compositions are used to treat inflammatory brain disorders, such as multiple sclerosis (MS), viral meningitis and encephalitis.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, *Immunology* (3d ed., Raven Press, 1993).

Another indication for the compounds of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8$^+$ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420–425 (1996); Georczynski et al., *Immunology* 87, 573-580 (1996); Georcyznski et al., *Transplant. Immunol.*, 3, 55–61 (1995); Yang et al., *Transplantation* 60, 71–76 (1995); Anderson et al., *APMIS* 102, 23–27 (1994).

A related use for compounds of this invention which bind to VLA-4 is in modulating the immune response involved in "graft versus host" disease (GVHD). See e.g., Schlegel et al., *J. Immunol.* 155, 3856–3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of the compounds of this invention is inhibiting tumor metastasis. Several tumor cells have been reported to express VLA-4 and compounds which bind VLA-4 block adhesion of such cells to endothelial cells. Steinback et al., *Urol. Res.* 23, 175–83 (1995); Orosz et al., *Int. J. Cancer* 60, 867–71 (1995); Freedman et al., *Leuk. Lymphoma* 13, 47–52 (1994); Okahara et al., *Cancer Res.* 54, 3233–6 (1994).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals[16].

Pharmaceutical compositions of the invention are suitable for use in a variety of drug delivery systems. Suitable formulations for use in the present invention are found in *Remington's Pharmaceutical Sciences,* Mace Publishing Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 μg to about 500 μg per kilogram body weight, preferably about 100 μg to about 300 μg per kilogram body weight. Suitable dosage ranges for intranasal administration are generally about 0.1 pg to 1 mg per kilogram body weight. Effective doses can be extrapolated from dose-response curves derived from in vitro or animal model test systems.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | | |
|---|---|---|
| aq or aq. | = | aqueous |
| AcOH | = | acetic acid |
| bd | = | broad doublet |
| bm | = | broad multiplet |
| bs | = | broad singlet |
| Bn | = | benzyl |
| Boc | = | N-tert-butoxylcarbonyl |
| Boc$_2$O | = | di-tert-butyl dicarbonate |
| BOP | = | benzotriazol-1-yloxy-tris(dimethylamino)phosphonium hexafluorophosphate |
| Cbz | = | carbobenzyloxy |
| CHCl$_3$ | = | chloroform |
| CH$_2$Cl$_2$ | = | dichloromethane |
| (COCl)$_2$ | = | oxalyl chloride |
| d | = | doublet |
| dd | = | doublet of doublets |
| dt | = | doublet of triplets |
| DBU | = | 1,8-diazabicyclo[5.4.0]undec-7-ene |
| DCC | = | 1,3-dicyclohexylcarbodiimide |
| DMAP | = | 4-N,N-dimethylaminopyridine |
| DME | = | ethylene glycol dimethyl ether |
| DMF | = | N,N-dimethylformamide |
| DMSO | = | dimethylsulfoxide |
| EDC | = | 1-(3-dimethylaminopropyl)-3-ethylcarbodiimide hydrochloride |
| Et$_3$N | = | triethylamine |
| Et$_2$O | = | diethyl ether |
| EtOAc | = | ethyl acetate |
| EtOH | = | ethanol |
| eq or eq. | = | equivalent |
| Fmoc | = | N-(9-fluorenylmethoxycarbonyl) |
| FmocONSu | = | N-(9-fluorenylmethoxycarbonyl)-succinimide |
| g | = | grams |
| h | = | hour |
| H$_2$O | = | water |
| HBr | = | hydrobromic acid |
| HCl | = | hydrochloric acid |
| HOBT | = | 1-hydroxybenzotriazole hydrate |
| hr | = | hour |
| K$_2$CO$_3$ | = | potassium carbonate |
| L | = | liter |
| m | = | multiplet |
| MeOH | = | methanol |
| mg | = | milligram |
| MgSO$_4$ | = | magnesium sulfate |
| mL | = | milliliter |
| mm | = | millimeter |
| mM | = | millimolar |
| mmol | = | millimol |
| mp | = | melting point |
| N | = | normal |

| | | |
|---|---|---|
| NaCl | = | sodium chloride |
| Na$_2$CO$_3$ | = | sodium carbonate |
| NaHCO$_3$ | = | sodium bicarbonate |
| NaOEt | = | sodium ethoxide |
| NaOH | = | sodium hydroxide |
| NH$_4$Cl | = | ammonium chloride |
| NMM | = | N-methylmorpholine |
| Phe | = | L-phenylalanine |
| Pro | = | L-proline |
| psi | = | pounds per square inch |
| PtO$_2$ | = | platinum oxide |
| q | = | quartet |
| quint. | = | quintet |
| rt | = | room temperature |
| s | = | singlet |
| sat | = | saturated |
| t | = | triplet |
| t-BuOH | = | tert-butanol |
| TFA | = | trifluoroacetic acid |
| THF | = | tetrahydrofuran |
| TLC or tlc | = | thin layer chromatography |
| Ts | = | tosyl |
| TsCl | = | tosyl chloride |
| TsOH | = | tosylate |
| μL | = | microliter |

The following Methods may be used to prepare the compounds of this invention.

Method A

Methyl Ester Preparation Procedure

Amino acid methyl esters can be prepared using the method of Brenner and Huber *Helv. Chim. Acta* 1953, 36, 1109.

Method B

BOP Coupling Procedure

The desired dipeptide ester was prepared by the reaction of a carboxylic acid (1 equivalent) with the appropriate amino acid ester or amino acid ester hydrochloride (1 equivalent), benzotriazol-1-yloxy-tris(dimethylamino) phosphonium hexafluorophosphate [BOP] (2.0 equivalent), triethylamine (1.1 equivalent), and DMF. The reaction mixture was stirred at room temperature overnight. The crude product is purified flash chromatography to afford the dipeptide ester.

Method C

Hydrogenation Procedure I

Hydrogenation was performed using 10% palladium on carbon (10% by weight) in methanol at 30 psi overnight. The mixture was filtered through a pad of Celite and the filtrate concentrated to yield the desired compound.

Method D

Hydrolysis Procedure I

To a chilled (0° C.) THF/H$_2$O solution (2:1, 5–10 mL) of the appropriate ester was added LiOH (or NaOH) (0.95 equivalents). The temperature was maintained at 0° C. and the reaction was complete in 1–3 hours. The reaction mixture was extracted with ethyl acetate and the aqueous phase was lyophilized resulting in the desired carboxylate salt.

Method E

Ester Hydrolysis Procedure II

To a chilled (0° C.) THF/H$_2$O solution (2:1, 5–10 mL) of the appropriate ester was added LiOH (1.1 equivalents). The temperature was maintained at 0° C. and the reaction was complete in 1–3 hours. The reaction mixture was concentrated and the residue was taken up into H$_2$O and the pH adjusted to 2–3 with aqueous HCl. The product was extracted with ethyl acetate and the combined organic phase was washed with brine, dried over MgSO$_4$, filtered and concentrated to yield the desired acid.

Method F

Ester Hydrolysis Procedure III

The appropriate ester was dissolved in dioxane/H$_2$O (1:1) and 0.9 equivalents of 0.5 N NaOH was added. The reaction was stirred for 3–16 hours and then concentrated. The resulting residue was dissolved in H$_2$O and extracted with ethyl acetate. The aqueous phase was lyophilized to yield the desired carboxylate sodium salt.

Method G

BOC Removal Procedure

Anhydrous hydrochloride (HCl) gas was bubbled through a methanolic solution of the appropriate Boc-amino acid ester at 0° C. for 15 minutes and the reaction mixture was stirred for three hours. The solution was concentrated to a syrup and dissolved in Et$_2$O and reconcentrated. This procedure was repeated and the resulting solid was placed under high vacuum overnight.

Method H tert-Butyl Ester Hydrolysis Procedure I

The tert-butyl ester was dissolved in CH$_2$Cl$_2$ and treated with TFA. The reaction was complete in 1–3 hr at which time the reaction mixture was concentrated and the residue dissolved in H$_2$O and lyophilized to yield the desired acid.

Method I

EDC Coupling Procedure I

To a CH$_2$Cl$_2$ solution (5–20 mL) of a carboxylic acid (1 equivalent), the appropriate amino acid ester hydrochloride (1 equivalent), N-methylmorpholine (1.1–2.2 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was poured into H$_2$O and the organic phase was washed with sat. NaHCO$_3$, brine, dried (MgSO$_4$ or Na$_2$SO$_4$), filtered and concentrated. The crude product was purified by column chromatography.

Method J

EDC Coupling Procedure II

To a DMF solution (5–20 mL) of a carboxylic acid (1 equivalent), the appropriated amino acid ester hydrochloride (1 equivalent), Et$_3$N (1.1 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was partitioned between EtOAc and H$_2$O and the organic phase washed with 0.2 N citric acid, H$_2$O, sat. NaHCO$_3$, brine, dried (MgSO$_4$ or Na$_2$SO$_4$), filtered and concentrated. The crude product was purified by column chromatography or preparative TLC.

Method K tert-Butyl Ester Hydrolysis Procedure II

The tert-butyl ester was dissolved in $CH_2Cl_2$ (5 mL) and treated with TFA (5 mL). The reaction was complete in 1–3 hours at which time the reaction mixture was concentrated and the residue dissolved in $H_2O$ and concentrated. The residue was redissolved in $H_2O$ and lyophilized to yield the desired product.

Method L

Carbamate Formation Procedure I

Into a reaction vial were combined 15.2 mmol, 1.0 eq. of the starting hydroxy compound (typically a tyrosine derivative) and 1.86 g (15.2 mmol, 1.0 eq) DMAP. Methylene chloride (50 mL), triethylamine (2.12 mL, 1.54 g, 15.2 mmol, 1.0 eq), and dimethylcarbamyl chloride (1.68 mL, 1.96 g, 18.2 mmol, 1.2 eq) were then added. The vial was capped tightly, and the reaction solution swirled to obtain a homogeneous solution. The reaction solution was then heated to 40° C. After 48 h, TLC of the resulting colorless solution indicated complete conversion. The work-up of the reaction solution was as follows: 50 mL EtOAc and 50 mL hexanes was added to the reaction mixture, and the resulting mixture was washed with 0.5 M citric acid (3×50 mL), water (2×50 mL), 10% $K_2CO_3$ (2×50 mL), and sat. NaCl (1×50 mL); dried with $MgSO_4$, filtered and evaporated to afford the desired compound.

Method M

Carbamate Formation Procedure II

Into a reaction vial were combined 84.34 mmol (1.0 eq) of the starting hydroxy compound (typically a tyrosine derivative) and 17.0 g (84.34 mmol, 1.0 eq) 4-nitrophenyl chloroformate. Methylene chloride (700 mL) was-added and the vial was capped with a septum. A nitrogen line was attached and the vial was immersed in a 4:1 water/ethanol dry ice slurry with stirring, to cool to −15° C. Triethylamine (29.38 mL, 21.33 g, 210.81 mmol, 2.5 eq) was added over five minutes with stirring and the stirring was continued at −10 to −15° C. for 1 h. N-Methyl piperazine (9.35 mL, 8.45 g, 84.34 mmol, 1.0 eq) was added over three minutes with stirring and stirring was continued overnight while warming to room temperature. The reaction mixture was diluted with 700 mL hexanes and the resulting mixture was washed repeatedly with 10% $K_2CO_3$, until no yellow color (from 4-nitrophenol) is observed in the aqueous layer. The mixture was then washed with sat. NaCl, dried over anhydrous $MgSO_4$, filtered and evaporated. The residue was dissolved in 500 mL of ethanol and evaporated to remove triethylamine. The residue was again dissolved in 500 mL of ethanol and evaporated to remove triethylamine. The residue was then dissolved in 400 mL of ethanol and 600 mL of water was added with stirring to precipitate a solid or oil. If an oil if formed, the oil is stirred vigorously to induce it to solidify. The solid is then isolated by filtration. Dissolution, precipitation, and filtration are repeated once and the resulting solid is rinsed with water to remove traces of yellow color. The solid is then subjected to high vacuum until the mass remains constant thereby affording the desired carbamyloxy compound.

Method N tert-Butyl Ester Hydrolysis Procedure III

A solution of the tert-butyl ester (typically 0.95 mmol) in 25 mL of formic acid was stirred at 25° C. for 24 hr. The solvent was removed and the residue was washed with diethyl ether (3x) to afford the desired product as a white solid.

Example 1

Synthesis of N-Benzyl-L-pyroglutamyl-L-phenylalanine

Step A—Preparation of N-Benzyl-L-pyroglutamic Acid Ethyl Ester

Ethyl (S)-(+)-2-pyrrolidone-5-carboxylate (1 g, 6.36 mmol) and benzyl bromide (0.76 mL, 6.36 mmol) were placed in dry THF (30 mL). The reaction mixture was stirred and cooled to 0° C. A 1M solution of tert-BuOK was added dropwise (6.36 ML, 6.36 mmol) and the reaction was stirred for an additional 0.5 h at 0° C. and allowed to come to room temperate where it was stirred for 24 hours under $N_2$. The reaction was then dissolved into a 1:1 mixture of $H_2O$/EtOAc. The organic layer was washed with 1M HCl, $H_2O$ and brine, and then dried over $MgSO_4$ to afford N-benzyl-L-pyroglutamic acid ethyl ester an oil.

Step B—Preparation of N-Benzyl-L-pyroglutamic Acid

The ester from Step A was then hydrolyzed using the procedure described in Method F to afford N-benzyl-L-pyroglutamic acid.

Step C—Preparation of N-Benzyl-L-pyroglutamyl-L-phenylalanine Ethyl Ester

The product from Step B was then coupled with L-phenylalanine ethyl ester using the procedure described in Method B (with substitution of N-methylmorpholine for triethylamine) to afford N-Benzyl-L-pyroglutamyl-L-phenylalanine ethyl ester.

NMR data was as follows:

$^1$H NMR (CDCl$_3$): δ 7.29 (m, 6H), 7.10 (m, 4H), 6.28 (brd, 1H), 5.13 (d, 1H), 4.90 (m, 1H), 4.19 (q, 2H), 3.77 (m, 2H), 3.29–2.98 (m, 2H), 2.37 (m, 2H), 2.16 (m, 1H), 1.82 (m, 1H), 1.28 (t, 3H).

$^{13}$C NMR (CDCl$_3$): δ 176.18 171.84, 171.49, 136.32, 136.19, 129.67, 129.37, 129.31, 129.25, 129.01, 128.41, 127.87, 62.38, 60.58, 53.24, 45.89, 38.24, 30.12, 23.84, 14.74.

Step D—Preparation of N-Benzyl-L-pyroglutamyl-L-phenylalanine

The title compound was prepared by hydrolysis of the product from Step C using the procedure described in Method F.

NMR data was as follows:

$^1$H NMR (CDCl$_3$): δ 7.28 (m, 6H), 7.11 (m, 4H), 6.67 (brd, 1H), 5.07 (d, 1H), 4.97 (m, 1H), 3.83 (m, 1H), 3.71 (d, 1H), 3.30 (m, 1H), 3.00 (m, 1H), 2.38 (m, 2H), 2.16 (m, 1H), 1.73 (m, 1H).

Example 2

Synthesis of N-Benzyloxycarbonyl-L-pyroglutamyl-L-phenylalanine

N-Benzyloxycarbonyl-L-pyroglutamyl-L-phenylalanine tert-butyl ester was prepared from the appropriate starting materials using the procedure described in Method B. The title compound was then prepared using the procedure described in Method D.

NMR data was as follows:

$^1$H NMR (CDCl$_3$): δ 7.40–6.92 (m, 1H), 5.19 (s, 2H), 4.93 (m, 1H), 4.55 (m, 1H), 3.25–2.89 (m, 2H), 2.42 (m, 2H), 2.16 (m, 1H), 1.94 (m, 1H).

$^{13}$C NMR (CDCl$_3$): δ 175.1 174.6 171.0, 151.8, 136.4, 135.3, 129.9, 129.2, 129.1, 129.1, 128.8, 127.7, 69.2, 60.6, 53.4, 38.0, 31.8, 22.9.

Example 3

Synthesis of N-Benzyl-L-pyroglutamyl-L-4-(phenylcarbonylamino)phenylalanine

The title compound was prepared from the appropriate starting materials using the procedures described in Examples 1 and 4.

NMR data was as follows:

$^1$H NMR (DMSO-d$_6$): δ 10.24 (s, 1H), 8.53 (d, 1H), 7.93 (d, 2H), 7.74 (d, 2H), 7.64–7.49 (m, 3H), 7.35–7.16 (m, 5H), 7.05 (d, 2H), 4.78 (d, 1H), 4.54 (m, 1H), 3.88 (m, 1H), 3.20–2.78 (m, 2H), 2.22 (m, 2H), 2.12 (m, 1H), 1.73 (m, 1H).

$^{13}$C NMR (DMSO-d$_6$): δ 175.0, 172.9, 171.3, 165.8, 137.7, 136.5, 135.0, 132.7, 131.5, 129.2, 128.5, 128.4, 127.8, 127.6, 127.3, 58.8, 53.2, 44.2, 36.0, 29.3, 22.3.

Example 4

Synthesis of N-(3,4-Dichlorobenzyl)-L-pyroglutamyl-L-4-(phenylcarbonylamino)phenylalanine Step A—Preparation of N-(3,4-Dichlorobenzyl)-L-pyroglutamyl-L-4-aminophenylalanine Methyl Ester N-(3,4-Dichlorobenzyl)-L-pyroglutamyl-L-4-aminophenylalanine methyl ester was prepared from the appropriate starting materials using the procedures described in Methods B and C.

Step B—Preparation of N-(3,4-Dichlorobenzyl)-L-pyroglutamyl-L-4-(phenylcarbonylamino)phenylalanine Methyl Ester The ester from Step A (230 mg, 0.495 mmol) was then placed in pyridine and benzoyl chloride (63.2 mL, 0.545 mmol) was added dropwise and the reaction was stirred for 2 hours. The resulting mixture was evaporated to dryness and taken up in EtOAc. The organic layer was washed with H$_2$O, 1M HCl, brine, and dried over MgSO$_4$ to give N-(3,4-dichlorobenzyl)-L-pyroglutamyl-L-4-(phenylcarbonylamino)-phenylalanine methyl ester as a white solid.

Step C—Preparation of N-(3,4-Dichlorobenzyl)-L-pyroglutamyl-L-4-(phenylcarbonylamino)phenylalanine Methyl Ester The title compound was prepared by hydrolyzing the product from Step B using the procedure described in Method F.

NMR data was as follows:

$^1$H NMR (DMSO-d$_6$): δ 10.22 (s, 1H), 8.56 (brd, 1H), 7.93 (d, 2H), 7.68 (d, 2H), 7.56 (m, 4H), 7.31 (s, 1H), 7.20 (d, 2H), 7.00 (d, 1H), 4.60 (d, 1H), 4.53 (m, 1H), 3.96 (m, 1H), 3,42 (d, 1H), 3.16–2.79 (m, 2H), 2.32 (m, 2H), 2.19 (m, 1H), 1.79 (m, 1H).

$^{13}$C NMR (DMSO-d$_6$): δ 175.4, 173.0, 171.1, 166.0, 138.1, 138.0, 135.4, 133.1, 132.0, 131.5, 130.9, 130.1, 129.8, 129.1, 128.4, 128.3, 127.6, 120.4, 59.4, 53,4, 43.7, 36.5, 29.6, 22.1.

Example 5

Synthesis of N-(3-Chlorobenzyl)-L-pyroglutamyl-L-4-(phenylcarbonylamino)phenylalanine Methyl Ester The title compound was prepared from the appropriate starting materials using the procedure described in Example 4.

NMR data was as follows:

$^1$H NMR (DMSO-d$_6$): δ 10.23 (s, 1H), 8.67 (d, 1H), 7.92 (d, 2H), 7.70 (d, 2H), 7.52 (m, 3H), 7.31 (m, 2H), 7.19 (m, 3H), 6.98 (m, 2H), 4.68 (d, 1H), 4.58 (m, 1H), 3.93 (m, 1H), 3.65 (s, 3H), 3,41 (d, 1H), 3.11–2.82 (m, 2H), 2.30 (m, 2H), 2.15 (m, 1H), 1.77 (m, 1H).

Example 6

Synthesis of N-(3-Chlorobenzyl)-L-pyroglutamyl-L-4-(phenylcarbonylamino)phenylalanine The title compound was prepared from the product of Example 5 using the procedure described in Method F.

NMR data was as follows:

$^1$H NMR (DMSO-d$_6$): δ 10.23 (s, 1H), 8.67 (d, 1H), 7.92 (d, 2H), 7.70 (d, 2H), 7.52 (m, 3H), 7.31 (m, 2H), 7.19 (m, 3H), 6.98 (m, 2H), 4.68 (d, 1H), 4.58 (m, 1H), 3.93 (m, 1H), 3,41 (d, 1H), 3.11–2.82 (m, 2H), 2.30 (m, 2H), 2.15 (m, 1H), 1.77 (m, 1H).

Example 7

Synthesis of N-(4-Chlorobenzyl)-L-pyroglutamyl-L-4-(phenylcarbonylamino)phenylalanine The title compound was prepared from the product of Example 8 using the procedure described in Method F.

NMR data was as follows:

$^1$H NMR (DMSO-d$_6$): δ 10.25 (s, 1H), 8.51 (d, 1H), 7.93 (d, 2H), 7.72 (d, 2H), 7.54 (m, 3H), 7.33 (d, 2H), 7.20 (d, 2H), 7.01 (d, 2H), 4.67 (d, 1H), 4.52 (m, 1H), 3.85 (m, 1H), 3.15–2.77 (m, 2H), 2.30 (m, 2H), 2.11 (m, 1H), 1.76 (m, 1H).

Example 8

Synthesis of N-(4-Chlorobenzyl)-L-pyroglutamyl-L-4-(phenylcarbonylamino)phenylalanine Methyl Ester The title compound was prepared from the appropriate starting materials using the procedure described in Example 4.

NMR data was as follows:

$^1$H NMR (DMSO-d$_6$): δ 10.25 (s, 1H), 8.51 (d, 1H), 7.93 (d, 2H), 7.72 (d, 2H), 7.54 (m, 3H), 7.33 (d, 2H), 7.20 (d, 2H), 7.01 (d, 2H), 4.67 (d, 1H), 4.52 (m, 1H), 3.85 (m, 1H), 3.65 (s, 3H), 3.15–2.77 (m, 2H), 2.30 (m, 2H), 2.11 (m, 1H), 1.76 (m, 1H).

Example 9

Synthesis of N-(4-Methylbenzyl)-L-pyroglutamyl-L-(4-phenylcarbonylamino)phenylalanine Methyl Ester The title compound was prepared from the appropriate starting materials using the procedure described in Example 4.

NMR data was as follows:

¹H NMR (DMSO-d$_6$): δ 10.25 (s, 1H), 8.59 (d, 1H), 7.94 (d, 2H), 7.74 (d, 2H), 7.55 (m, 3H), 7.20 (d, 2H), 7.09 (d, 2H), 6.89 (d, 2H), 4.73 (d, 1H), 4.60 (m, 1H), 3.82 (m, 1H), 3.66 (s, 3H), 3.32 (d, 1H), 3.13–2.81 (m, 2H), 2.30 (m, 2H), 2.24 (s, 3H), 2.10 (m, 1H), 1.73 (m, 1H).

Example 10

Synthesis of N-(4-Methylbenzyl)-L-pyroglutamyl-L-4-(phenylcarbonylamino)phenylalanine The title compound was prepared from the product of Example 9 using the procedure described in Method F.

NMR data was as follows:

¹H NMR (DMSO-d$_6$): δ 10.25 (s, 1H), 8.59 (d, 1H), 7.94 (d, 2H), 7.74 (d, 2H), 7.55 (m, 3H), 7.20 (d, 2H), 7.09 (d, 2H), 6.89 (d, 2H), 4.73 (d, 1H), 4.60 (m, 1H), 3.82 (m, 1H), 3.32 (d, 1H), 3.13–2.81 (m, 2H), 2.30 (m, 2H), 2.24 (s, 3H), 2.10 (m, 1H), 1.73 (m, 1H).

Example 11

Synthesis of N-(4-Methoxybenzyl)-L-pyroglutamyl-L-4-(phenylcarbonylamino)phenylalanine Methyl Ester The title compound was prepared from the appropriate starting materials using the procedures described in Example 4.

NMR data was as follows:

¹H NMR (DMSO-d$_6$): δ 10.25 (s, 1H), 8.59 (d, 1H), 7.94 (d, 2H), 7.74 (d, 2H), 7.55 (m, 3H), 7.42 (d, 2H), 6.92 (d, 2H), 6.83 (d, 2H), 4.73 (d, 1H), 4.60 (m, 1H), 3.83 (m, 1H), 3.70 (s, 3H), 3.65 (s, 3H), 3.32 (d, 1H), 3.16–2.81 (m, 2H), 2.30 (m, 2H), 2.10 (m, 1H), 1.73 (m, 1H).

¹³C NMR (DMSO-d$_6$): δ 174.8, 172.2, 171.6, 165.9, 158.9, 138.2, 136.4, 132.7, 131.9, 129.6, 129.6, 128.8, 128.6, 128.0, 120.4, 114.3, 58.8, 55.4, 53.5, 52.5, 44.0, 36.2, 29.6, 22.8.

Example 12

Synthesis of N-(4-Methoxybenzyl)-L-pyroglutamyl-L-4-(phenylcarbonylamino)phenylalanine The title compound was prepared from the product of Example 11 using the procedure described in Method F.

NMR data was as follows:

¹H NMR (DMSO-d6): δ 10.25 (s, 1H), 8.59 (d, 1H), 7.94 (d, 2H), 7.74 (d, 2H), 7.55 (m, 3H), 7.42 (d, 2H), 6.92 (d, 2H), 6.83 (d, 2H), 4.73 (d, 1H), 4.60 (m, 1H), 3.83 (m, 1H), 3.70 (s, 3H), 3.32 (d, 1H), 3.16–2.81 (m, 2H), 2.30 (m, 2H), 2.10 (m, 1H), 1.73 (m, 1H).

Example 13

Synthesis of N-(3-Chlorobenzyl)-L-pyroglutamyl-L-(N'-benzyl)histidine

N-(3-Chlorobenzyl)-L-pyroglutamyl-L-(N'-benzyl)histidine methyl ester was prepared from the appropriate starting materials using the procedure described in Method B. The title compound was then prepared by hydrolysis of the methyl ester using the procedure described in Method E.

NMR data was as follows:

¹H NMR (DMSO-d$_6$): δ 8.08 (brd, 1H), 7.59 (s, 1H), 7.38–7.12 (m, 8H), 7.05 (s, 1H), 6.84 (s, 1H), 5.08 (m, 2H), 4.68 (d, 1H), 4.27 (m, 1H), 3.97 (m, 1H), 3.59 (d, 1H), 3.05–2.70 (m, 2H), 2.26 (m, 2h), 2.08 (m, 1H), 1.79 (m, 1H).

¹³C NMR (DMSO-d$_6$): δ 175.3, 173.9, 170.5, 139.9, 139.3, 138.1, 136.9, 133.5, 130.7, 129.0, 128.0, 127.8, 127.6, 127.0, 116.7, 59.8, 54.0, 49.8, 44.1, 31.1, 29.6, 22.8.

Example 14

Synthesis of N-(4-Methylbenzyl)-L-pyroglutamyl-L-(N'-benzyl)histidine Methyl Ester The title compound was prepared from the appropriate starting materials using the procedures described in Examples 1 and 13.

NMR data was as follows:

¹H NMR (CDCl$_3$): δ 8.18 (d, 1H), 7.42 (s, 1H), 7.33 (m, 3H), 7.16–7.06 (m, 6H), 6.67 (s, 1H), 5.14 (d, 1H), 5.04 (s, 2H), 4.79 (m, 1H), 3.88 (m, 1H), 3.82 (d, 1H), 3.64 (s, 3H), 3.15–2.94 (m, 2H), 2.70–2.57 (m, 1H), 2.39 (m, 1H), 2.27–2.00 (m, 2H).

¹³C NMR (CDCl$_3$): δ 176.2, 172.1, 172.1, 138.3, 138.0, 137.9, 136.4, 133.5, 130.0, 129.6, 129.2, 120.0, 127.8, 117.5, 60.8, 53.9, 53.9, 51.5, 45.5, 30.9, 29.5, 23.9, 21.7.

Example 15

Synthesis of N-(4-Methylbenzyl)-L-pyroglutamyl-L-(N'-benzyl)histidine

The title compound was prepared from the product of Example 14 using the procedures described in Method E.

NMR data was as follows:

¹H NMR (D$_2$O): δ 7.70 (s, 1H), 7.35–7.20 (m, 5H), 7.08 (d, 2H), 6.98 (s, 1H), 6.74 (d, 2H), 5.05 (s, 2H), 4.49–4.42 (m, 2H), 3.94 (m, 1H), 3.31 (d, 1H), 3.14–2.73 (m, 2H), 2.24 (s, 3H), 2.56–2.11 (m, 3H), 1.91 (m, 1H).

Example 16

Synthesis of N-Benzyl-D-pyroglutamyl-L-phenylalanine

The title compound was prepared from the appropriate starting materials using the procedures described in Examples 1 and 2.

NMR data was as follows:

¹H NMR (DMSO-d$_6$): δ 8.52 (d, 1H), 7.4–7.1 (m, 10H), 6.97 (d, 1H), 4.83 (dd, 2H), 4.73 (dd), 4.50 (m, 1H), 3.84 (m, 1H), 3.50 (dd, 2H), 3,40 (dd), 3.13 (2H), 2.85 (2H), 2.19 (m, 2H), 2.03 (m, 1H), 1.48 (m, 1H).

¹³C NMR (DMSO-d$_6$): δ 175.0, 173.2, 171.3, 138.0, 136.9, 129.5, 129.4, 128.9, 128.9, 128.6, 128.4, 128.2, 127.7, 126.8, 57.1, 53.5, 44.5, 35.8, 29.5, 22.9.

Example 17

Synthesis of N-(4-Benzyl-3-oxothiomorpholin-5-carbonyl)-L-phenylalanine

The title compound was prepared from the product of Example 18 using the procedure described in Method F.

NMR data was as follows:

¹H NMR (CDCl$_3$): δ 7.38–6.98 (m, 10H), 5.48 (d, 1H), 4.97 (m, 1H), 4.20 (t, 1H), 4.09 (t), 3.67 (d, 1H), 3.50–2.78 (m, 6H).

¹³C NMR (CDCl$_3$): δ 175.5, 169.7, 168.0, 136.2, 135.8, 129.9, 129.5, 129.3, 129.0, 128.7, 128.0, 62.5, 53.9, 51.1, 38.0, 31.3, 29.4.

Example 18

Synthesis of N-(4-Benzyl-3-oxothiomorpholin-5-carbonyl)-L-phenylalanine Ethyl Ester Step A—Preparation of N-Benzyl-3-oxothiomorpholin-5-carboxylic Acid S-(Methylcarboxyethyl)cysteine (*Biochemistry*, 1989, 28(2), 465) (1.633 g, 7.88 mmol) was placed in MeOH (50 mL) and benzaldehyde (0.8 mL, 7.88 mmol) was added. The mixture was stirred for 10 minutes and then sodium cyanoborohydride (0.594 g, 946 mmol) was added. The reaction was stirred overnight under $N_2$ and then filtered to afford 853 mg of a white solid. This white solid was then heated in water overnight to afford N-benzyl-3-oxothiomorpholin-5-carboxylic acid as a white solid.

Step B—Preparation of N-(4-Benzyl-3-oxothiomorpholin-5-carbonyl)-L-phenylalanine Ethyl Ester The title compound was prepared from the product of Step A and L-phenylalanine ethyl ester using the procedures described in Method B.

NMR data was as follows:

$^1$H NMR (CDCl$_3$): δ 7.38–7.15 (m, 10H), 6.57 (d, 1H), 5.54 (d, 1H), 4.17 (m, 1H), 4.89 (q, 1H), 4.20 (q, 2H), 3.09 (d, 1H) 3,46 (d, 1H), 3.25–2.80 (m, 5H), 1.29 (t, 3H).

$^{13}$C NMR (CDCl$_3$): δ 171.6, 169.4, 168.6, 136.3, 136.1, 129.8, 129.7, 129.5, 129.3, 129.0, 128.6, 127.0, 62.4, 62.4, 53.8, 50.7, 38.1, 31.3, 29.4, 14.8.

Example 19

Synthesis of N-(4-Benzyl-3-oxothiomorpholin-5-carbonyl)-L-4-nitrophenylalanine Methyl Ester The title compound was prepared from the appropriate starting materials using the procedures described in Example 18.

NMR data was as follows:

$^1$H NMR (CDCl$_3$): δ 8.16 (d, 2H), 7.42–7.17 (m, 7H), 6.84 (d, 1H), 5.63 (d, 1H), 4.99 (m, 1H), 4.18 (m, 1H), 3.78–3.70 (m, 4H), 3.56 (d, 1H), 3.38–3.15 (m, 3H), 3.05–2.87 (m, 2H).

$^{13}$C NMR (CDCl$_3$): δ 171.5, 169.7, 166.5, 147.8, 144.1, 136.1, 130.8, 129.3, 128.9, 128.8, 124.4, 62.5, 53.7, 53.5, 50.9, 38.1, 31.5, 29.6.

Example 20

Synthesis of N-Benzyl-L-pyroglutamyl-L-4-(N,N-dimethylcarbamyloxy)phenylalanine Isopropyl Ester The title compound was prepared from the appropriate starting materials using the procedure described in Method L to afford white crystals, mp 167–169° C.

Physical data was as follows:

Anal. Calc'd for $C_{27}H_{33}N_3O_6$: C, 65.44; H, 6.71; N, 8.48. Found: C, 65.06; H, 6.73; N, 8.42.

MS (+EI): 495 (M+)+.

Example 21

Synthesis of N-Benzyl-L-pyroglutamyl-L-3-chloro-4-(N,N-dimethylcarbamyloxy)phenylalanine Methyl Ester N-Benzyl-L-pyroglutamyl-L-3-chloro-4-hydroxyphenylalanine methyl ester was prepared from the appropriate starting materials using the procedure described in Method B. The title compound was then prepared from the methyl ester using the procedure described in Method L to afford a white solid.

Physical data was as follows:

Anal. Calc'd for $C_{25}H_{28}ClN_3O_6 \cdot 0.1$ $CH_2Cl_2$: C, 59.06; H, 5.57; N, 8.33. Found: C, 59.08; H, 5.37; N, 8.24.

MS (+ESI): 502 (M+1)+.

Example 22

Synthesis of N-(4-Fluorobenzyl)-L-pyroglutamyl-L-4-(N,N-dimethylcarbamyloxy)phenylalanine The title compound was prepared from the appropriate starting materials using the sequential application of the procedure described in Methods B, L and N to afford a white solid, mp 227–230° C.

Physical data was as follows:

Anal. Calc'd for $C_{24}H_{26}FN_3O_6$: C, 61.14; H, 5.56; N, 8.91. Found: C, 60.80; H, 5.48; N, 8.81.

MS (+ESI): 472 (M+1)+.

Example 23

Synthesis of N-(4-Fluorobenzyl)-L-pyroglutamyl-L-4-[(thiomorpholin-4'-yl)carbonyloxy)phenylalanine N-(4-Fluorobenzyl)-L-pyroglutamyl-L-4-[(thiomorpholin-4'-yl)carbonyloxy)phenylalanine tert-butyl ester was prepared from the appropriate starting materials using the procedure described in Method M (thiomorpholine was substituted for N-methylpiperazine). The title compound was then prepared from the tert-butyl ester using the procedure described in Method N to afford a white solid, mp 266–268° C. (dec.)

Physical data was as follows:

Anal. Calc'd for $C_{26}H_{28}FN_3O_6S$: C, 58.97; H, 5.33; N, 7.93. Found: C, 57.98; H, 5.09; N, 7.62.

MS (−ESI): 528 (M−1)−.

Example 24

Synthesis of N-(4-Cyanobenzyl)-L-pyroglutamyl-L-4-(N,N-dimethylcarbamyloxy)phenylalanine The title compound was prepared from the appropriate starting materials using the sequential application of the procedures described in Methods B, L and N to afford a white solid, mp 232–236° C. (dec).

Physical data was as follows:

Anal. Calc'd for $C_{25}H_{26}N_4O_6 \cdot 0.5$ $H_2O \cdot 0.08$ $C_4H_{10}O$: C, 61.63; H, 5.68; N, 11.35. Found: C, 62.01; H, 5.51; N, 11.00.

MS (+APCI): 479 (M+1)+.

Example 25

Synthesis of N-(4-Nitrobenzyl)-L-pyroglutamyl-L-4-(N,N-dimethylcarbamyloxy)phenylalanine tert-Butyl Ester The title compound was prepared from the appropriate starting materials using the sequential application of the procedures described in Methods B and L to afford white crystals, mp 159–161° C.

Physical data was as follows:

Anal. Calc'd for $C_{28}H_{34}N_4O_8$: C, 60.64; H, 6.18; N, 10.10. Found: C, 60.41; H, 6.34; N, 9.73.

MS (+ESI): 555 (M+1)+.

Example 26

Synthesis of N-Benzyl-L-pyroglutamyl-L-3-chloro-4-(N,N-dimethylcarbamyloxy)phenylalanine The title compound was prepared from the product of Example 21 using the procedure described in Method D to afford a white solid.

Physical data was as follows:

Anal. Calc'd for $C_{24}H_{25}ClN_3O_6Li.2.5\ H_2O$: C, 53,49; H, 5.61; N, 7.80. Found: C, 53.18; H, 5.02; N, 7.59.

MS (+ESI): 488 (M+1)+.

Example 27

Synthesis of N-(4-Fluorobenzyl)-L-pyroglutamyl-L-4-[(4'-(pyridin-2'-yl)piperazin-1'-yl)carbonyloxy]phenylalanine The title compound was prepared from the product of Example 28 using the procedure described in Method N.

Physical data was as follows:

Anal. Calc'd for $C_{31}H_{32}FN_5O_6..2.5\ HCO_2H$: C, 60.47; H, 5.39; N, 11.02. Found: C, 57.31; H, 5.69; N, 9.53.

MS (−ESI): 588 (M−1)−.

Example 28

Synthesis of N-(4-Fluorobenzyl)-L-pyroglutamyl-L-4-[(4'-(pyridin-2'-yl)piperazin-1'-yl)carbonyloxy]phenylalanine tert-Butyl Ester The title compound was prepared from the appropriate starting materials using the procedures of Method M (1-(pyridin-2-yl)piperazine was substituted for N-methylpiperazine) to afford white crystals, mp 198–199° C.

Physical data was as follows:

Anal. Calc'd for $C_{35}H_{40}FN_5O_6$: C, 65.10; H, 6.24; N, 10.85. Found: C, 65.04; H, 6.17; N, 10.77.

MS (+ESI): 646 (M+1)+.

Example 29

Synthesis of N-(Pyridin-3-ylmethyl)-L-pyroglutamyl-L-tyrosine tert-Butyl Ester Step A—Preparation of N-(Pyridin-3-ylmethyl)-L-pyroglutamic Acid Methyl Ester N-(Pyridin-3-ylmethyl)-L-pyroglutamic acid methyl ester was prepared by reductive alkylation of L-glutamic acid with the appropriate aldehyde followed by acid catalyzed cyclization employing the procedures described in *J. Amer. Chem. Soc.* 106, 4539 (1984). The following work-up procedures were employed: after the aqueous solution (pH=3) was heated overnight, the solution was cooled to 25° C. and the pH was adjusted to 7 using 2N NaOH. The aqueous phase was lyophilized to a gummy solid which was treated with methanolic HCl overnight. After filtration, the solvent was evaporated to afford the crude methyl ester which was taken up in $CH_2Cl_2$ and washed with saturated sodium bicarbonate, followed by saturated brine, and then dried over $MgSO_4$ and evaporated to an oil. This oil was then flash chromatographed on alumina (activity grade 3) using ethyl acetate/hexane 1:1 as the eluent to afford N-(pyridin-3-ylmethyl)-L-pyroglutamic acid methyl ester as a colorless oil.

Step B—Preparation of N-(Pyridin-3-ylmethyl)-L-pyroglutamyl-L-tyrosine tert-Butyl Ester The title compound was prepared by reacting the acid obtained from the hydrolysis of the product of Step A (using Method D) and L-tyrosine tert-butyl ester following the procedures described in Method B.

Physical data was as follows:

Anal. Calc'd for $C_{24}H_{29}N_3O_5.0.22\ C_3H_7NO.0.7\ H_2O$: C, 63.26; H, 6.87; N, 9.63. Found: C, 63.16; H, 6.60; N, 9.44.

MS (+ESI): 440 (M+1)+.

Example 30

Synthesis of N-(Pyridin-3-ylmethyl)-L-pyroglutamyl-L-4-(N,N-dimethylcarbamyloxy)phenylalanine The title compound was prepared from the product of Example 31 using the procedure described in Method N to afford a white solid.

Physical data was as follows:

Anal. Calc'd for $C_{23}H_{26}N_4O_6.0.12\ C_4H_8O_2.0.25\ H_2O$: C, 60.05; H, 5.89; N, 11.93. Found: C, 59.94; H, 5.77; N, 11.91.

MS (+ESI): 455 (M+1)+.

Example 31

Synthesis of N-(Pyridin-3-ylmethyl)-L-pyroglutamyl-L-4-(N,N-dimethylcarbamoyloxy)phenylalanine tert-Butyl Ester The title compound was prepared from the product of Example 29 using the procedure described in Method M to afford a crystalline solid, mp 157–158° C.

Physical data was as follows:

Anal. Calc'd for $C_{27}H_{34}N_4O_6$: C, 63.51; H, 6.71; N, 10.97. Found: C, 63.35; H, 6.75; N, 10.88.

MS (+ESI): 511 (M+1)+.

Example 32

Synthesis of N-(Pyridin-3-ylmethyl)-L-pyroglutamyl-L-4-[(4'-(pyridin-2'-yl)piperazin-1'-yl)carbonyloxy]phenylalanine tert-Butyl Ester The title compound was prepared from the appropriate starting materials using the procedures of Method M (1-(pyridin-2-yl)piperazine was substituted for N-methylpiperazine) to afford a white solid.

Physical data was as follows:

Anal. Calc'd for $C_{34}H_{40}N_6O_6$: C, 64.95; H, 6.41; N, 13.37. Found: C, 64.94; H, 6.40; N, 13.18.

MS (+ESI): 629 (M+1)+.

Example 33

Synthesis of N-(Pyridin-3-ylmethyl)-L-pyroglutamyl-L-4-[(4'-(pyridin-2'-yl)piperazin-1'-yl)carbonyloxy]phenylalanine The title compound was prepared from the product of Example 32 using the procedure described in Method N to afford a white solid.

Physical data was as follows:

Anal. Calc'd for $C_{30}H_{32}N_6O_6$: C, 62.93; H, 5.63; N, 14.68. Found: C, 62.20; H, 5.49; N, 14.22.

MS (−ESI): 571 (M−1)−.

Example 34

Synthesis of N-(4-Benzyl-5-oxo-4-azatricyclo[4.2.1.0 (3,7)]nonane-3-carbonyl)-L-tyrosine tert-Butyl Ester Step A—Preparation of 5-Oxo-4-azatricyclo[4.2.1.0 (3.7)]nonane-3-carboxylic acid A solution of endo-6-carboxybicyclo[2.2.1]heptane-2-one (6.72 g, 43.6 mmol (*J. Org. Chem.* 41:1233 (1976)), KCN (3,41 g, 52.4 mmol) and $(NH_4)_2CO_3$ (16.77 g, 174.6 mmol) in 206 mL 1:1 $H_2O$-ethanol was heated 24 h at 55° C. The condenser was then removed and the reaction mixture was refluxed for 1.5 h. After the reaction was acidified with conc. HCl and cooled to 5° C., a precipitate was obtained which after washing with $H_2O$ and dried to afford 1.74 g (18%) of a white solid, mp 286° C. This intermediate (1.74g, 7.76 mmol) was converted to the title compound by refluxing in 30 mL of 2.5 N NaOH for 24 h. Acidification to pH=0 gave the desired product as a white solid, mp 298–300° C.

Physical data was as follows:

Anal. Calc'd for $C_9H_{11}NO_3$: C, 59.66; H, 6.12; N, 7.73. Found: C, 59.39; H, 6.24; N, 7.67.

Step B—Preparation of 5-Oxo-4-azatricyclo[4.2.1.0 (3.7)]nonane-3-carboxylic Acid Methyl Ester To a suspension of 5-oxo-4-azatricyclo[4.2.1.0 (3,7)] nonane-3-carboxylic acid (183 mg, 1.0 mmol) in 10 mL MeOH under nitrogen at –78° C. was added $SOCl_2$ (75 μL, 1.0 mmol). After 169 h, the solvent was evaporated to afford 195 mg of a white solid which was taken up in 10 mL $CHCl_3$, washed sequentially with 10 mL saturated $NaHCO_3$ and 10 mL saturated NaCl, dried over $MgSO_4$ and evaporated to give 160 mg (81%) of a white solid, mp 142–144° C.

Physical data was as follows:

MS (FI-POS): 196 (M+1)+.

Step C—Preparation of 4-Benzyl-5-oxo-4-azatricyclo [4.2.1.0 (3.7)]nonane-3-carboxylic Acid Methyl Ester To a suspension of 5-oxo-4-azatricyclo[4.2.1.0 (3,7)] nonane-3-carboxylic acid methyl ester (68 8 mg, 3.52 mmol) in 10 mL of THF under nitrogen at 25° C. was added LiHMDS (3.87 mL of 1N THF solution, 3.87 mmol). After 15 min, benzyl bromide (0.42 mL, 3.53 mmol) was added. After 169 h, the reaction was quenched by addition of 10 mL of saturated $NH_4Cl$ solution. The reaction mixture was partitioned between 30 mL $CH_2Cl_2$ and 10 mL $H_2O$. The organic phase was separated, washed with 50 mL saturated NaCl, dried over $MgSO_4$ and evaporated to give 770 mg of an oil. Flash chromatography of 740 mg of this material, eluting with 95:5, $CH_2Cl_2$-EtOAc, afforded 510 mg (51%) of the title compound as a colorless oil (0.14 $CH_2Cl_2$ solvate).

Physical data was as follows:

MS (+ESI): 286 (M+1)+.

Step D—Preparation of 4-Benzyl-5-oxo-4-azatricyclo [4.2.1.0 (3,7)]nonane-3-carboxylic Acid To a solution of 4-benzyl-5-oxo-4-azatricyclo[4.2.1.0 (3,7)]nonane-3-carboxylic acid methyl ester•0.14 methylene chloride solvate (399 mg, 1.34 mmol) in 13 mL MeOH under nitrogen at 25° C. was added 1.5 mL of 1N LiOH. After 117 h, most of the solvent was removed and the residue was taken up in 10 mL 1N NaOH, washed with 2×10 mL $Et_2O$, acidified by addition of 10 mL 2 N HCl, extracted 2×with 10 mL $Et_2O$, dried over $MgSO_4$ and evaporated to give 225 mg (71%) of a white solid, mp 191–194° C.

Physical data was as follows:

Anal. Calc'd for $C_{16}H_{17}NO_3$: C, 70.83; H, 6.32; N, 5.16. Found: C, 70.56; H, 6.39; N, 5.01.

Step E—Preparation of N-(4-Benzyl-5-oxo-4-azatricyclo [4.2.1.0 (3,7)]nonane-3-carbonyl)-L-tyrosine tert-Butyl Ester The title compound was prepared from 4-benzyl-5-oxo-4-azatricyclo[4.2.1.0 (3,7)]nonane-3-carboxylic acid (0.60 mmol) and L-tyosine tert-butyl ester using the procedures described in Example 1 to afford 300 mg (93%) of a white solid.

Physical data was as follows:

Anal. Calc'd for $C_{29}H_{34}N_2O_5$.0.5 $C_4H_8O_2$: C, 69.64; H, 7.16; N, 5.24. Found: C, 69.41, H, 7.02; N, 5.34.

MS (+ESI): 491 (M+1)+.

Example 35

Synthesis of N-(4-Benzyl-5-oxo-4-azatricyclo [4.2.1.0 (3,7)]nonane-3-carbonyl)-L-4-(N,N-dimethylcarbamyloxy)phenylalanine tert-Butyl Ester The title compound was prepared from the product of Example 34 using the procedure described in Method L to afford a white solid.

Physical data was as follows:

Anal. Calc'd for $C_{32}H_{39}N_3O_6$: C, 68.43; H, 7.00; N, 7.48. Found: C, 67.98; H, 7.00; N, 7.27.

MS (+ESI): 562 (M+1)+.

Example 36

Synthesis of N-(4-Benzyl-5-oxo-4-azatricyclo [4.2.1.0 (3,7)]nonane-3-carbonyl)-L-4-(N,N-dimethylcarbamyloxy)phenylalanine The title compound was prepared from the product of Example 35 using the procedure described in Method N to afford a white solid.

Physical data was as follows:

Anal. Calc'd for $C_{28}H_{31}N_3O_6$.0.5 $C_4H_{10}O$: C, 66.40; H, 6.69; N, 7.74. Found: C, 65.72; H, 6.42; N, 7.95.

MS (+ESI): 506 (M+1)+.

Example 37

Synthesis of N-(Benzyl)-L-pyroglutamyl-L-tyrosine Ethyl Ester

To a solution of N-benzyl-L-pyroglutamic acid (*J. Am. Chem. Soc.* 106:4539 (1984), 1.00 g, 4.56 mmol), L-tyrosine ethyl ester hydrochloride (1.23 g, 5.01 mmol) and BOP (2.22 g, 5.01 mmol) in DMF (32 mL) under nitrogen was added triethylamine (1.14 g, 11.26 mmol) dropwise and the resulting solution was stirred at ambient temperature for 22.5 h. The reaction was quenched by addition of 150 mL of saturated sodium bicarbonate and 150 mL of EtOAc. The organic layer was separated and washed sequentially with 150 mL $H_2O$, 150 mL 10% citric acid and 150 mL saturated brine, dried over $MgSO_4$ and evaporated to 1.6 g (82%) of a white solid, mp 192–194° C.

Physical data was as follows:

$^1$H NMR (DMSO-$d_6$, 400 MHz) δ 9.23 (s, 1H); 8.52 (d, 1H, J=7.9 Hz); 7.32–7.23 (m, 3H); 7.03–6.97 (m, 4H); 6.69–6.65 (m, 2H); 4.75 (d, 1H, J=15.2 Hz); 4.49–4.43 (m, 1H); 4.11–4.01 (m, 2H); 3.88–3.85 (m, 1H); 3.37 (d, 1H,

J=15.2 Hz); 2.99–2.94 (m, 1H); 2.78–2.72 (m, 1H); 2.33–2.08 (m, 3H); 1.98 (s, 0.2H); 1.76–1.70 (m, 1H); 1.14 (t, 3H, J=7.25 Hz).

IR (KBr, cm$^{-1}$) 3400; 3250; 3060; 1725; 1680; 1670; 1550; 1510; 1440; 1265; 1220.

MS (–FAB) 409.1 (M–H); 381.0; 302.0; 275.0; 257.0; 217.0; 183.0; 91.0.

Anal. Calc'd for $C_{23}H_{26}N_2O_5 \cdot 0.2M$ EtOAc: C, 66.78; H, 6.50; N, 6.54. Found: C, 66.48; H, 6.35; N, 6.66.

Example 38

Synthesis of N-(Benzyl)-L-pyroglutamyl-L-tyrosine

To a solution of N-(benzyl)-L-pyroglutamyl-L-tyrosine ethyl ester 0.2 ethyl acetate solvate (0.139 g, 0.325 mmol) in MeOH (3.25 mL) under nitrogen was added 1 N aqueous LiOH (0.72 mL, 0.72 mmol). After 3 days, the solvent was evaporated and the residue was partitioned between 10 mL $H_2O$ and 10 mL $CH_2Cl_2$. The aqueous layer was washed with 10 mL $CH_2Cl_2$ and acidified to pH=1 by addition of 7 mL 1 N HCl. The precipitate was filtered, washed with 20 mL 1:1 $CHCl_3$/EtOAc and dried to afford 0.0835 g of a white solid (67%).

Physical data was as follows:

$^1$H NMR (DMSO-$d_6$, 400 MHz) δ 12.76 (brd s,1H); 9.22 (s, 1H); 8.40 (d, 1H, J=8.35 Hz); 7.32–7.23 (m, 3H); 7.02–6.97 (m, 4H); 6.68–6.65 (m, 2H); 4.74 (d, 1H, J=14.94 Hz); 4.47–4.41 (m, 1H); 3.87–3.84 (m, 1H); 3.40–3.24 (m, 1H); 3.03–2.98 (m, 1H); 2.75–2.69 (m, 1H); 2.35–2.04 (m, 3H); 1.76–1.69 (m, 1H).

IR (KBr, cm$^{-1}$) 3280; 1745; 1670; 1660; 1550; 1515; 1255; 1200; 820; 700.

MS (+FAB) 383.1 (M+H); 367.1; 327.0; 311.0; 295.0; 279.0; 237.0; 197.0; 174.1; 136.0; 105.0.

Anal. Calc'd for $C_{21}H_{22}N_2O_5 \cdot 0.2M$ $H_2O$: C, 65.35; H, 5.85; N, 7.26. Found: C, 65.14; H, 5.66; N, 7.13.

Example 39

Synthesis of N-(Benzyl)-L-pyroglutamyl-L-4-[(4'-methylpiperazin-1'-yl)carbonyloxy]phenylalanine Ethyl Ester To a suspension of N-(benzyl-L-pyroglutamyl)-L-tyrosine ethyl ester 0.2 ethyl acetate solvate (0.894 g, 2.09 mmol) and 4-nitrophenyl chloroformate (0.435 g, 2.09 mmol) in 13 mL of 1:1 $CH_3CN/CH_2Cl_2$ under nitrogen at 0° C. was added DMAP (0.032 g, 0.26 mmol) followed by TEA (0.529 g, 5.22 mmol). After 30 min at 0° C. the reaction mixture was warmed up to 25° C. and kept at this temperature for 30 min. The reaction was then cooled back down to 0° C. and 1-methylpiperazine (0.206 g, 1.06 mmol) was added. The ice bath was then removed and the reaction mixture was stirred at 25° C. for 3 h 15 min. The reaction mixture was then diluted with 50 mL $Et_2O$ and washed with 4×25 mL 10% sodium carbonate, diluted with $CH_2Cl_2$, dried over $K_2CO_3$ and evaporated to 1.0 g (88%) of crude solid which was recrystallized from toluene/hexane to afford white crystals, mp 145–148° C.

Physical data was as follows:

$^1$H NMR (DMSO-$d_6$, 400 MHz) δ 8.59 (d, 1H, J=8.1 Hz); 7.31–7.19 (m, 5H); 7.04–7.00 (m, 4H); 4.76 (d, 1H, J=15.2 Hz); 4.56–4.51 (m, 1H); 4.11–4.05 (m, 2H); 3.87–3.84 (m, 1H);); 3.54–3.35 (m, 5H); 3.10–3.05 (m, 1H); 2.90–2.84 (m, 1H); 2.32–2.09 (m, 10H); 1.74–1.69 (m, 1H); 1.24–1.23 (m, 0.4H); 1.15 (t, 3H, J=7.0 Hz); 0.85 (m, 0.3H).

IR (KBr, cm$^{-1}$) 3300; 1740; 1720; 1680; 1650; 1550; 1410; 1240; 1210; 1200; 1160; 700.

MS (EI) 536 (M+); 491; 234; 174; 127; 91; 83; 70; 58; 44.

Anal. Calc'd for $C_{29}H_{36}N_4O_6 \cdot 0.1M$ $C_6H_{14}$: C, 65.22; H, 6.90; N, 10.28. Found: C, 65.06; H, 6.66; N, 9.88.

Example 40

Synthesis of N-(Benzyl)-L-pyroglutamyl-L-4-(1'-methylpiperidin-4'-yloxy)phenylalanine Lithium Salt To a solution of N-(benzyl)-L-pyroglutamyl-L-4-[(4'-methylpiperazin-1'-yl)carbonyloxy]phenylalanine ethyl ester 0.1 hexane solvate (0.200 g, 0.367 mmol) in MeOH (3.67 mL) under nitrogen was added 1 N aqueous LiOH (0.35 mL, 0.35 mmol). After 28 h the solvent was removed, 25 mL $H_2O$ was added, the aqueous solution was washed twice with 25 mL of $CH_2Cl_2$, filtered and lyophilized to afford 0.16 g (77%) of a white solid.

Physical data was as follows:

$^1$H NMR (DMSO-$d_6$, 400 MHz) δ 7.60 (d, 2H, J=7.3 Hz); 7.30–7.21 (m, 3H); 7.13–7.10 (m, 2H); 7.05–7.03 (m, 2H); 6.92–6.88 (m, 2H); 4.75 (d, 1H, J=15.2 Hz); 4.04–4.01 (m, 1H); 3.89–3.86 (m, 1H); 3.54–3.33 (m, 1H); 3.13–3.09 (m, 1H); 2.92–2.87 (m, 1H); 2.33–2.05 (m, 10H); 1.79–1.75 (m, 1H).

IR (KBr, cm$^{-1}$) 3400; 1720; 1680;1610;1420; 1240; 1200; 1160; 1000; 710.

MS (+FAB) 515.0 (M+Li); 471.0; 220.9; 174.0; 91.0.

Anal. Calc'd for $C_{27}H_{31}N_4O_6Li \cdot 3.0M$ H20: C, 57.04; H, 6.56; N, 9.85. Found: C, 57.27; H, 5.70; N, 9.59.

Example 41

Synthesis of N-(Benzyl)-L-pyroglutamyl-L-4-(pyridin-4-ylcarbonylamino)phenylalanine Methyl Ester A solution of N-benzyl-L-pyroglutamic acid (J. Am. Chem. Soc. 106:4539 (1984), 1.00 g, 4.562 mmol), 4-[(4-pyridinylcarbonyl)amino]-L-phenylalanine methyl ester (1.532 g, 4.562 mmol) and BOP (2.018 g, 4.562 mmol) in acetonitrile (30.0 mL) was charged to a 100 mL round bottom flask equipped with a stir bar and nitrogen inlet. Triethylamine (1.272 mL, 9.123 mmol) was added dropwise and the resulting solution was stirred at 25° C. for 16 h. The solvent was stripped off and the material taken up in methylene chloride (75 mL) and washed with saturated sodium bicarbonate solution (50 mL×3), dried ($K_2CO_3$) and the solvent removed to give a beige solid (2.000 g). This material was chromatographed on silica gel (9:1 $CH_2Cl_2:CH_3OH$) yielding a white solid which was recrystallized from acetonitrile to provide 1.744 g (76%) of white needles, mp 204–208° C.

Physical data was as follows:

$^1$H NMR (DMSO-$d_6$, 400 MHz) δ 10.47 (s, 1H); 8.77 (d, 2H, J=6.2 Hz); 8.60 (d, 1H, J=7.9 Hz); 7.83 (d, 2H, J=6.2 Hz); 7.71 (d, 2H, J=8.6 Hz); 7.31–7.19 (m, 5H); 7.02 (d, 2H, J=5.1 Hz); 4.76 (d, 1H, J=14.9 Hz); 4.61–4.55 (m, 1H); 3.87–3.84 (m, 1H); 3.65 (s, 3H); 3.36 (d, 1H, J=14.4 Hz); 3.11–3.06 (m, 1H); 2.89–2.83 (m, 1H); 2.34–2.21 (m, 2H); 2.17–2.09 (m, 1H); 1.76–1.70 (m, 1H).

IR (KBr, cm$^{-1}$) 3460; 3325; 3100; 3030; 2960; 1660; 1625; 1540; 1490; 1425; 1325; 1225; 700.

MS (+FAB) 501.1 (M+H); 485.1; 475.1; 465.1; 451.0; 394.1; 279.0; 174.0; 91.0.

Anal. Calc'd for $C_{28}H_{28}N_4O_5 \cdot 0.15$ $CH_2Cl_2$: C, 65.87; H, 5.56; N, 10.92. Found: C, 65.87; H, 5.70; N, 11.36.

Example 42

Synthesis of N-(Benzyl)-L-pyroglutamyl-L-4-(pyridin-4-ylcarbonylamino)phenylalanine Lithium Salt N-(Benzyl)-L-pyroglutamyl-L-4-(pyridin-4-ylcarbonylamino)-phenylalanine methyl ester 0.15 methylene chloride solvate (0.400 g, 0.799 mmol) was taken up in methanol (15 mL) and the solvent stripped off using a rotovap. This procedure was repeated twice more to remove any traces of acetonitrile. The solid was dissolved in methanol (15 mL) and charged to a 25 mL round bottom flask equipped with a magnetic stir bar, air condenser and nitrogen inlet. The mixture was warmed until the ester dissolved (oil bath temperature =40° C.) and 1N LiOH (759 µL, 0.759 mmol) was added, via syringe, and the solution stirred for 16 h under nitrogen. The reaction solution was transferred to a 50 mL round bottom flask and the solvent stripped off yielding a white solid (0.731 g). This solid was taken up in water (50 mL) and washed with methylene chloride (25 mL). An emulsion formed and was allowed to separate. The organic phase was separated and the aqueous phase was filtered, pumped on for 3 h and lyophilized to give 0.353 g (94%) of a fluffy white solid, mp=347° C. (decompose).

Physical data was as follows:

$^1$H NMR (DMSO-$d_6$, 400 MHz) δ 10.48 (s, 1H); 8.76–8.74 (m, 2H); 7.85–7.83 (m, 2H); 7.60 (t, 2H, J=8.6 Hz); 7.53 (d, 1H, J=6.8 Hz); 7.30–7.20 (m, 3H); 7.15–7.09 (m, 2H); 7.04 (d, 2H, J=7.6 Hz); 4.77 (d, 1H, J=15.4 Hz); 4.01–3.98 (m, 1H); 3.90–3.86 (m, 1H); 3.43 (d, 1H, J=15.2 Hz); 3.13–3.08 (m, 1H); 2.94–2.89 (m, 1H); 2.29–2.19 (m, 2H); 2.11–2.05 (m, 1H); 1.80–1.77 (m, 1H).

IR (KBr, cm$^{-1}$) 3325; 3030; 2960; 1660; 1600; 1530; 1425; 1325; 830; 700.

MS (+FAB) 487.0 (M+H); 471.0; 450.9; 429.0; 417.0; 400.9; 385.0; 279.0; 236.9; 91.0.

Anal. Calc'd for $C_{27}H_{26}N_4O_5 \cdot 3.00$ $H_2O$ C, 58.34; H, 5.72; N, 10.25. Found: C, 58.45; H, 5.44; N, 9.95.

Example 43

Synthesis of N-(Benzyl)-L-pyroglutamyl-L-4-nitrophenylalanine Ethyl Ester

A solution of N-benzyl-L-pyroglutamic acid (*J. Am. Chem. Soc.* 106:4539 (1984), 1.00 g, 4.562 mmol), (S)-4-nitro-phenylalanine ethyl ester (1.262 g, 4.562 mmol) and HOBT (1.233 g, 9.123 mmol) in methylene chloride (40.0 mL) was charged to a 100 mL round bottom flask equipped with a stir bar and nitrogen inlet. Hunig's base (3.25 mL, 18.246 mmol) was added dropwise. The solution remained heterogeneous so acetonitrile (10 mL) was added followed by the addition of EDC (1.749 g, 9.123 mmol) and the resulting milk white mixture was stirred at 25° C. for 16 h. The solvent was stripped off and the solid taken up in ethyl acetate (100 mL) and washed with saturated ammonium chloride solution (100 mL×2), saturated sodium bicarbonate solution (50 mL×2), brine (50 mL×2), dried (MgSO$_4$) and the solvent removed to yield 1.166 g (58%) of a yellow solid. This material was recrystallized from ethyl acetate giving a white solid, mp=186–187° C.

Physical data was as follows:

$^1$H NMR (DMSO-$d_6$, 400 MHz) δ 8.63 (d, 1H, J=8.1 Hz); 8.15 (d, 2H, J=9.1 Hz); 7.51 (d, 2H, J=8.8 Hz); 7.29–7.23 (m, 3H); 6.99–6.95 (m, 2H); 4.76 (d, 1H, J 15.2 Hz); 4.69–4.64 (m, 1H); 4.11 (q, 2H, J=5.5 Hz); 3.82–3.79 (m, 2H); 3.37 (d, 1H, J=15.2 Hz); 3.28–3.23 (m, 1H); 3.06–3.00 (m, 1H); 2.33–2.21 (m, 2H); 2.17–2.09 (m, 1H); 1.73–1.65 (m, 1H); 1.16 (t, 3H, J=7.1 Hz).

IR (KBr, cm$^{-1}$) 3300; 3100; 2990; 2900; 1730; 1690; 1600; 1515; 1450; 1350; 1275; 1250; 1175; 1100; 1025; 840; 750; 700.

MS (+FAB) 439.0 (M+H); 422.0; 394.0; 366.0; 176.0; 175.0; 174.0; 165.0; 146.0; 118.0; 106.0; 92.0; 91.0; 90.0; 84.0; 65.0.

Anal. Calc'd for $C_{24}H_{26}N_2O_6 \cdot 0.09$ $CH_2Cl_2$ C, 62.03; H, 5.80; N, 9.59. Found: C, 62.03; H, 5.68; N, 9.40.

Example 44

Synthesis of N-(Benzyl)-L-pyroglutamyl-L-4-nitrophenylalanine Lithium Salt

N-(Benzyl)-L-pyroglutamyl-L4-nitrophenylalanine ethyl ester 0.09 methylene chloride solvate (0.100 g, 0.228 mmol) was dissolved in refluxing ethanol (10 mL) and charged to a 25 mL round bottom flask equipped with a magnetic stir bar, air condenser and nitrogen inlet. 1N LiOH (216 µL, 0.216 mmol) was added, via syringe, and the solution stirred at 70° C. for 16 h under nitrogen. The reaction solution went from clear to brown upon the LiOH addition and some precipitate was noted. This solution was transferred to a 125 mL separatory funnel with an additional 50 mL of water and washed with methylene chloride (50 mL). An emulsion formed and was allowed to separate. The organic phase was removed and the aqueous phase was filtered, pumped on for 3 h and lyophilized to give 0.048 g, (53%) of a fluffy white solid, mp=285–287° C. (decompose).

Physical data was as follows:

$^1$H NMR (DMSO-$d_6$, 400 MHz) δ 8.07–8.02 (m, 2H); 7.64–7.61 (m, 1H); 7.39–7.36 (m, 2H); 7.31–7.21 (m, 3H); 7.13 (d, 1H, J=7.5 Hz); 7.00 (d, 1H, J=7.6 Hz); 4.75 (d, 1H, J=15.4 Hz); 4.06–4.01 (m, 1H); 3.94–3.89 (m, 1H); 3.45 (d, 1H, J=15.4 Hz); 3.07–2.99 (m, 1H); 2.29–2.14 (m, 2H); 2.12–2.00 (m, 1H); 1.79–1.73 (m, 1H); 1.57–1.54 (m, 1H).

IR (KBr, cm$^{-1}$) 3400; 3100; 2900; 1675; 1600; 1515; 1450; 1425; 1350; 1250; 1100; 840; 690.

MS (-FAB) 410.1 (M-H); 394.0; 337.1; 275.1; 217.1; 183.0; 153.0; 109.0; 91.0.

Anal. Calc'd for $C_{21}H_{21}N_3O_6 \cdot 1.25$ $H_2O$ C, 57.34; H, 5.16; N, 9.55. Found: C, 57.44; H, 5.05; N, 9.48.

Example 45

Synthesis of N-(Benzyl)-L-pyroglutamyl-L-4-aminophenylalanine Ethyl Ester

A solution of N-(benzyl)-L-pyroglutamyl-L-4-nitrophenylalanine ethyl ester 0.09 methylene chloride solvate (0.900 g, 2.048 mmol) and $SnCl_2 \cdot H_2O$ in ethanol (30 mL) was charged to a 100 mL round bottom flask equipped with a magnetic stir bar and nitrogen inlet. This solution was stirred at ambient temperature, under nitrogen, for 16 h. The reaction solution was transferred to a 125 mL separatory funnel with 50 mL of ethyl acetate. The organic phase was washed with saturated sodium bicarbonate (50 mL), dried ($K_2CO_3$), and the solvent removed to yield 0.702 g of a white solid. This material was chromatographed on silica gel (ethyl acetate) giving 0.362 g (39%) of a white solid, mp=147–149° C.

Physical data was as follows:

$^1$H NMR (DMSO-$d_6$, 400 MHz) δ 8.49 (d, 1H, J 8.1 Hz); 7.34–7.24 (m, 3H); 7.04 (d, 2H, J=7.7 Hz); 6.84 (d, 2H, J=8.3 Hz); 6.48 (d, 2H, J=9.3 Hz); 4.94 (s, 2H); 4.76 (d, 1H, J=14.9 Hz); 4.44–4.38 (m, 1H); 4.11–4.01 (m, 2H); 3.89–3.86 (m, 1H); 3.40 (d, 1H, J=15.2 Hz); 2.91–2.86 (m, 1H); 2.72–2.66 (m, 1H); 2.34–2.20 (m, 2H); 2.16–2.08 (m, 1H); 1.77–1.71 (m, 1H); 1.16 (t, 3H, J=7.1 Hz).

IR (KBr, cm$^{-1}$) 3400; 3300; 3040; 3030; 2990; 2950; 1740; 1675; 1550; 1525; 1425; 1225; 1200; 1125; 830; 700.

MS (+FAB) 409.0 (M+H); 336.0; 254.0; 253.0; 191.0; 174.0; 146.0; 107.0; 106.0; 91.0; 90.0; 77.0; 65.0; 55.0; 46.0; 45.0; 44.0.

Anal. Calc'd for $C_{23}H_{27}N_3O_4$: C, 67.47; H, 6.65; N, 10.26. Found: C, 67.08; H, 6.69; N, 10.20.

Example 46

Synthesis of N-(Benzyl)-L-pyroglutamyl-L-4-[(thiomorpholin-4'-yl)carbonyloxy]phenylalanine tert-Butyl Ester A solution of N-benzyl-L-pyroglutamic acid (*J. Am. Chem. Soc.* 106:4539 (1984), 10.00 g, 45.62 mmol), L-tyrosine tert-butyl ester (11.91 g, 50.17 mmol) and BOP (22.19 g, 50.17 mmol) in DMF (250.0 mL) was charged to a 500 mL round bottom flask equipped with a stir bar and nitrogen inlet. Triethylamine (7.00 mL, 50.17 mmol) was added dropwise and the resulting solution was stirred at 25° C. for 16 h. The solution was transferred to a 1.0 L separatory funnel with ethyl acetate (300 mL) and washed with saturated sodium bicarbonate solution (300 mL×2), brine (300 mL×2), dried (MgSO$_4$) and the solvent removed to give 18.63 g (93%) of N-(benzyl)-L-pyroglutamyl-L-tyrosine tert-butyl ester as a white solid.

A solution of N-(benzyl)-L-pyroglutamyl-L-tyrosine tert-butyl ester (1.00 g, 2.280 mmol) and 4-nitrophenyl chloroformate (0.442 g, 2.092 mmol) were dissolved in methylene chloride (5 mL) and charged to a 25 mL round bottom flask equipped with a magnetic stir bar and nitrogen inlet. The solution was cooled in an ice bath and triethylamine (729 µL, 5.230 mmol) was added, via syringe, and the resulting yellow solution was stirred for 30 min in an ice bath, then 30 min at ambient temperature. The solution was recooled in an ice bath and thiomorpholine (210 µL, 2.092 mmol) was added. The solution was allowed to warm to room temperature and stirred for 16 h under nitrogen. The solution was transferred to a 250 mL separatory funnel with 100 mL of diethyl ether and this organic phase was washed with 10% K$_2$CO$_3$ (50 mL×12), dried (K$_2$CO$_3$) and the solvent removed to give a white solid (0.992 g). This material was recrystallized from ethanol to yield 0.411 g (35%) of white crystals, mp=169–171° C.

Physical data was as follows:

$^1$H NMR (DMSO-$d_6$, 400 MHz) δ 8.53 (d, 1H, J=8.1 Hz); 7.33–7.21 (m, 5H); 7.07–7.03 (m, 4H); 4.78 (d, 1H, J=15.2 Hz); 4.49–4.36 (m, 1H); 3.89–3.86 (m, 1H); 3.82 (s, 2H); 3.68 (s, 2H); 3.43 (d, 1H, J=17.0 Hz); 3.08–3.03 (m, 1H); 2.89–2.83 (m, 1H); 2.67 (s, 4H); 2.32–2.26 (m, 2H); 2.17–2.11 (m, 1H); 1.77–1.73 (m, 1H); 1.38 (s, 9H).

IR (KBr, cm$^{-1}$) 3400; 3300; 3100; 2980; 2910; 1725; 1675; 1660; 1560; 1510; 1460; 1420; 1375; 1300; 1225; 1200; 1100; 960; 800; 760; 700; 650; 550.

MS (+FAB) 635.5 (M+NH$_4$); 618.4; 562.2; 506.4; 407.8; 344.5; 255.9.

Example 47

Synthesis of N-(Benzyl)-L-pyroglutamyl-L-4-(1'-benzyloxycarbonylpiperidin-4'-ylcarbonylamino) phenylalanine Methyl Ester To a solution of N-benzyl-L-pyroglutamic acid (0.50 g, 2.275 mmol), L-4-(1'-benzyloxycarbonylpiperidin-4'-ylcarbonylamino)phenylalanine methyl ester hydrochloride (1.08 g, 2.275 mmol) and BOP (1.10 g, 2.48 mmol) in acetonitrile (60 mL) under nitrogen was added triethylamine (0.7 mL, 5.005 mmol) dropwise. The mixture was stirred 48 h at room temperature. The reaction was then worked-up by evaporation of the solvent, addition of ethyl acetate, sequential washing with 1N HCl solution, water, saturated sodium bicarbonate solution, saturated brine and drying with MgSO$_4$. Evaporation of the solvent gave a crude solid which was purified by flash chromatography using EtOAc/MeOH (99: 1) as eluent, to afford the desired product as a solid (0.332 g, mp 223–225° C., 23% yield).

Physical data was as follows:

$^1$H NMR (DMSO-$d_6$, 400MHz) δ 9.88 (s, 1H); 8.56 (d, 1H, J=8.1 Hz); 7.52 (d, 2H, J=8.5 Hz); 7.4–7.2 (m, 8H); 7.11 (d, 2H, J=8.3 Hz); 6.99 (d, 2H, J=8.1 Hz); 5.07 (s, 2H); 4.73 (d, 1H, J=14.7 Hz); 4.54 (m, 1H); 4.02 (m, 2H); 3.84 (m, 1H); 3.63 (s, 3H); 3.27 (m, 2H); 3.02 (m, 1H); 2.90–2.79 (brd m, 3H); 2.30–2.23 (brd m, 2H); 2.10 (m, 1H); 1.80–1.70 (brd m, 3H); 1.55–1.45 (brd m, 2H).

IR (KBr, cm$^{-1}$) 3400; 3275; 2910; 1690; 1550; 1435; 1325; 1225; 1120; 1100; 1010; 940; 700.

MS (+FAB) 663.1 ([M+Na]$^+$); 597.1; 507.1; 174.0; 91.0.

Anal. Calc'd for $C_{36}H_{40}N_4O_7 \cdot 0.15 C_4H_8O_2$: C, 66.12; H, 6.35; N, 8.56. Found: C, 66.03; H, 5.01; N, 8.56.

Example 48

Synthesis of N-(Benzyl)-L-pyroglutamyl-L-4-(1'-benzyloxycarbonylpiperidin-4'-ylcarbonylamino) phenylalanine To a suspension of N-(benzyl)-L-pyroglutamyl-L-4-(1'-benzyloxycarbonyl-piperidin-4'-ylcarbonylamino) phenylalanine methyl ester (0.30 g, 0.468 mmol) in a aqueous methanol solution (MeOH/H$_2$O, 12 mL/1 mL) under nitrogen was added solid LiOH (0.039 g, 0.929 mmol). After stirring for 24 h, the solvent was concentrated to about 3mL and acidified using 10% citric acid solution. A white precipitate was filtered off, washed with water and dried in vacuo to yield the product as a off white solid (0.22 g, mp 193–196° C., yield 75%).

Physical data was as follows:

$^1$H NMR (DMSO-$d_6$, 400MHz) δ 9.87 (s, 1H); 8.42 (d, 1H, J=8.3 Hz); 7.52 (d, 2H, J=8.5 Hz); 7.4–7.2 (m, 8H); 7.11 (d, 2H, J=8.5 Hz); 6.97 (d, 2H, J=7.9 Hz); 5.07 (s, 2H); 4.73 (d, 1H, J=15.1 Hz); 4.49 (m, 1H); 4.02 (brd d, 2H, J=12.7 Hz); 3.84 (m, 1H); 3.26 (s, 1H); 3.07 (m, 1H); 2.98–2.7 (brd m, 3H); 2.32–2.20 (brd m, 2H); 2.10 (m, 1H); 1.80–1.70 (brd m, 3H); 1.55–1.45 (brd m, 2H).

IR (KBr, cm$^{-1}$) 3420; 3300; 3050; 2950; 1660; 1550; 1440; 1325; 1225; 1175; 1110; 1060; 950; 820; 760; 700; 510.

MS (−FAB) 625.4 ([M−H]−); 491.3; 367.2; 275.1; 183.1; 91.0.

Anal. Calc'd for $C_{35}H_{38}N_4O_7 \cdot 1.5 H_2O$: C, 64.30; H, 6.32; N, 8.57. Found: C, 64.33; H, 6.09; N, 8.44.

Example 49

Synthesis of N-(Benzyl)-L-pyroglutamyl-L-4-(piperidin-4'-ylcarbonylamino)phenylalanine Hydrobromide Hydrogen bromide in HOAc (33 wt. %, 2 mL) was added to a flask containing N-(benzyl)-L-pyroglutamyl-L-4-(1'-benzyloxycarbonylpiperidin-4'-ylcarbonylamino)

phenylalanine (0.10 g, 0.16 mmol) and stirred for 50 min. Et$_2$O was added until a precipitate fell out of solution and the mixture was then stirred for 10 min. The precipitate was filtered off and washed with fresh Et$_2$O. The Et$_2$O layers were discarded. The precipitate was then washed with water until all of the material on the filter paper dissolved. This aqueous phase was then lyophilized to generate the product as a solid (0.082 g, mp 191–194° C., 81% yield).

Physical data was as follows:

$^1$H NMR (DMSO-d$_6$, 400MHz) δ 9.98 (s, 1H); 8.48 (m, 2H); 8.25 (brd s, 1H); 7.52 (d, 2H, J=8.3 Hz); 7.27–7.20 (m, 3H); 7.13 (d, 2H, J=8.5 Hz); 6.97 (d, 2H, J=8.1 Hz); 4.70 (d, 1H, J=14.9 Hz); 4.49 (m, 1H); 3.83 (m, 1H); 3.05 (m, 1H); 2.86–2.94 (m, 2H); 2.89–2.73 (m, 1H); 2.67–2.57 (m, 1H); 2.32–2.19 (brd m, 2H); 2.14–2.06 (brd m, 1H); 1.98–1.90 (m, 2H); 1.83–1.68 (brd m, 2H).

MS (+FAB) 493.2 ([M+H]$^+$); 482.0; 460.1; 307.1; 220.2; 176.0; 154.1.

Anal. Calc'd for C$_{27}$H$_{32}$N$_4$O$_5$·HBr. 3.3 H$_2$O: C, 51.23; H, 6.30; N, 8.85. Found: C, 51.19; H, 5.79; N, 8.80

Example 50

Synthesis of N-(Benzyl)-L-pyroglutamyl-L-4-(1'-methylpiperidin-4'-yloxy)phenylalanine Ethyl Ester To a solution of N-(benzyl)-pyroglutamic acid (0.29 g, 1.32 mmol), L-4-(1'-methylpiperidin-4'-yloxy) phenylalanine ethyl ester dihydrochloride salt (0.50 g, 1.32 mmol) and BOP (0.64 g, 1.45 mmol) in DMF (15 mL) under nitrogen was added triethylamine (0.65 mL, 4.62 mmol) and the mixture stirred at room temperature for 7 days. The reaction was quenched by addition of excess saturated sodium bicarbonate solution and EtOAc. The organic phase was separated and concentrated to an oil that was flash chromatographed using CH$_2$Cl$_2$/MeOH (95:5) as eluent to afford the product as a solid (0.15 g, 22% yield).

Physical data was as follows:

$^1$H NMR (DMSO-d$_6$, 400MHz) δ 8.57 (d, 1H, J=7.9 Hz); 7.26 (m, 3H); 7.11 (d, 2H, J=8.5 Hz); 7.01 (m, 2H); 6.86 (d, 2H, J=8.5 Hz); 4.72 (d, 1H, J=15.1 Hz); 4.52 (m, 1H); 4.33 (brd s, 1H); 4.0–4.1 (brd m,3H); 3.85 (m, 1H); 3.02 (m, 1H); 2.70–2.83 (brd m, 3H); 2.40–2.20 (brd m, 7H); 2.12 (m, 1H); 1.93–1.85 (brd s, 2H); 1.75–1.50 (brd m, 4H); 1.21–1.12 (m, 3H).

MS (EI) 507 ([M+H]$^+$); 421; 174; 133; 107; 98; 70.

Anal. Calc'd for C$_{29}$H$_{37}$N$_3$O$_5$: C, 68.62; H, 7.35; N, 8.28. Found: C, 60.53; H, 6.91; N, 8.20.

Example 51

Synthesis of -N-(Benzyl)-L-pyroglutamyl-L-4-(1'-methylpiperidin-4'-yloxy)phenylalanine Lithium Salt To a solution of N-(benzyl)-L-pyroglutamyl-L4-(1'-methylpiperidin-4'-yloxy)phenylalanine ethyl ester (0.10 g, 0.197 mmol) in MeOH (3 mL) under nitrogen was added 1N LiOH solution (0.187 mL, 0.187 mmol). After stirring overnight, the solvent was evaporated and 10% citric acid solution was added. A precipitate was filtered off, washed with water and dried in vacuo to produce the product as a solid (0.08 g, m p 232–235° C., 83% yield).

Physical data was as follows:

$^1$H NMR (DMSO-d$_6$, 400 MHz) δ 7.60 (d, 1H, J 7.2 Hz); 7.25 (m, 3H); 7.01 (m, 4H); 6.70 (d, 2H, J=11.4 Hz); 4.71 (d, 1H, J=15.1 Hz); 4.18 (m, 1H); 4.02 (m, 1H); 3.87 (m,1H); 3.05 (m, 1H); 2.85 (m, 1H); 2.57–2.54 (brd m, 2H); 2.28–2.18 (m, 2H); 2.13 (s, 3H); 2.11–2.05 (brd m, 3H); 1.87–1.72 (brd m, 3H); 1.58–1.49 (m, 2H).

MS (+ESI) 480.1 ([M+H]$^+$); 352.0; 274.0; 240.9; 179.9.

Example 52

Synthesis of N-(Benzyl)-L-pyroglutamyl-L-4-(N,N-dimethylcarbamyloxy)phenylalanine Ethyl Ester To a solution of N-(benzyl)-L-pyroglutamyl-L-tyrosine ethyl ester (0.50 g, 1.22 mmol), dimethylaminopyridine (0.146 g, 1.20 mmol), triethylamine (0.25 mL, 1.83 mmol) and pyridine (1.5 mL) in CH$_2$Cl$_2$ (10 mL) was added dimethylcarbamyl chloride (0.15 mL, 1.70 mmol) dropwise. After stirring for 60 h, the reaction was quenched by addition of 10% citric acid solution (40 mL) followed by extraction using ethyl acetate/hexane (65:35) (100 mL). The organic phase was separated and washed sequentially with water, saturated sodium bicarbonate solution, water, saturated brine, dried with MgSO$_4$ and evaporated in vacuo to afford the product as a solid (0.57 g, mp 150–152° C., 99% yield).

Physical data was as follows:

$^1$H NMR (DMSO-d$_6$, 400 MHz) δ 8.59 (d, 1H, J=8.1 Hz); 7.25 (m, 3H); 7.18 (d, 2H, J=8.5 Hz); 7.02 (m, 4H); 4.75 (d, 1H, J=15.3 Hz); 4.53 (m, 1H); 4.10 (m, 2H); 3.85 (m, 1H); 3.40 (d, 1H, J=15.1 Hz); 3.09 (m, 1H); 3.01 (s, 3H); 2.88 (m, 4H); 2.33–2.24 (m, 2H); 2.18–2.08 (m, 1H); 1.76–1.67 (m, 1H); 1.14 (t, 3H, J=7.0 Hz).

IR (KBr, cm$^{-1}$) 3425; 2900; 1725; 1690; 1660; 1525; 1425; 1380; 1210; 1175; 1010; 845; 800; 750; 650; 520.

MS (EI) 481 ([M+H]$^+$); 436; 308; 263; 174; 91; 72.

Anal. Calc'd for C$_{26}$H$_{31}$N$_3$O$_6$: C, 64.85; H, 6.49; N, 8.73. Found: C, 65.00; H, 6.55; N, 8.70.

Example 53

Synthesis of N-(Benzyl)-L-pyroglutamyl-L-4-(N,N-dimethylcarbamyloxy)phenylalanine Lithium Salt To a stirred mixture of N-(benzyl)-L-pyroglutamyl-L-4-(N,N-dimethylcarbamyloxy)phenylalanine ethyl ester (0.3 g, 0.62 mmol) in THF (4 mL) was added 1N LiOH solution (0.59 mL, 0.59 mmol) and the mixture was stirred for 72 h. The reaction was quenched by dilution with water (15–20 mL) and the aqueous phase was extracted with CH$_2$Cl$_2$ three times. Lyophilization of the aqueous layer produced the product as a solid (0.27 g, 94% yield).

Physical data was as follows:

$^1$H NMR (DMSO-d$_6$, 400 MHz) δ 7.54 (d, 1H, J 6.8 Hz); 7.30–7.20 (brd m, 3H); 7.10 (d, 2H, J=8.5 Hz); 7.04 (m, 2H); 6.88 (m, 2H); 4.75 (d, 1H, J=15.1 Hz); 3.99 (q, 1H, J=6.3 Hz); 3.86 (m, 1H); 3.41 (d, 1H, J=15.3 Hz);, 3.11 (m, 1H); 3.00 (s, 3H); 2.88 (m, 4H); 2.30–2.19 (brd m, 2H); 2.12–2.05 (m, 1H); 1.79–1.72 (m, 1H).

IR (KBr, cm$^{-1}$) 3400; 2950; 1660; 1600; 1400; 1220; 1175; 700; 510.

MS (+FAB) 454.0 ([M+H]$^+$); 460.0 ([M+Li]$^+$); 410.0; 326.9; 279.0; 220.9; 173.9; 130.6; 80.3.

Anal. Calc'd for C$_{24}$H$_{27}$N$_3$O$_6$Li. 3 H$_2$O: C, 56.14; H, 6.28; N, 8.18. Found: C, 56.07; H, 5.88; N, 7.95.

Example 54

Synthesis of N-(Benzyl)-L-pyroglutamyl-L-4-(N,N-dimethylcarbamyloxy)phenylalanine tert-Butyl Ester BOP coupling of N-(benzyl)-L-pyroglutamic acid (1.96 g, 8.9 mmol) and L-tyrosine tert-butyl ester (2.32 g, 9.78 mmol) with triethylamine in DMF according to the method of Example 46 followed by a saturated sodium bicarbonate quench, addition of EtOAc and extraction with 10% citric acid solution, water, brine, drying (MgSO$_4$), filtration and concentration produced the precursor N-(benzyl)-L-pyroglutamyl-L-tyrosine acid tert-butyl ester (3.59 g, mp 167–169° C., 92% yield) as a crystalline solid.

Physical data was as follows:

Anal. Calc'd for C$_{25}$H$_{30}$N$_2$O$_5$: C, 68.48; H, 6.90; N, 6.39. Found: C, 68.20; H, 6.78; N, 6.75.

To a combined mixture of N-(benzyl)-L-pyroglutamyl-L-tyrosine acid tert-butyl ester (0.5 g, 1.14 mmol), N,N-dimethylaminopyridine (0.14 g, 1.14 mmol) and triethylamine (0.24 mL, 1.71 mmol) in CH$_2$Cl$_2$ (8 mL) was added dimethylcarbamyl chloride (0.15 mL, 1.59 mmol) dropwise. After stirring for 66 h, the reaction was quenched by addition of 10% citric acid solution (30 mL) followed by extraction using ethyl acetate/hexane (65:35) mixture (100 mL). The organic phase was separated, washed sequentially with water, saturated sodium bicarbonate solution, water, saturated brine, dried with MgSO$_4$ and evaporated in vacuo to afford the product as a solid (0.52 g, mp 184–185° C., 90% yield).

Physical data was as follows:

$^1$H NMR (DMSO-d$_6$, 400 MHz) δ 8.52 (d, 1H, J=8.1 Hz); 7.32–7.20 (m, 5H); 7.05–7.01 (m, 4H); 4.76 (d, 1H, J=15.1 Hz); 4.46 (m, 1H); 3.88 (m, 1H); 3.40 (d, 1H, J=15.1 Hz); 3.05–3.0 (m, 4H); 2.90(s, 3H); 2.85 (m, 1H); 2.34–2.26 (m,2H); 2.18–2.11 (m, 1H); 1.78–1.71 (m, 1H); 1.37 (s, 9H).

IR (KBr, cm$^{-1}$) 3410; 3275; 2950; 1725; 1660; 1550; 1430; 1375; 1210; 1150; 750; 690; 520.

MS (EI) 509 ([M+H]$^+$); 453; 408; 233; 174; 91; 72.

Anal. Calc'd for C$_{28}$H$_{35}$N$_3$O$_6$: C, 66.00; H, 6.92; N, 8.25. Found: C, 65.88; H, 6.91; N, 8.24.

Example 55

Synthesis of N-(Benzyl)-L-pyroglutamyl-L-4-[(4'-methylpiperazin-1'-yl)carbonyloxy]phenylalanine tert-Butyl Ester N-(benzyl)-L-pyroglutamyl-L-tyrosine acid tert-butyl ester (0.50 g, 1.14 mmol) was combined with p-nitrophenyl chloroformate (0.218 g, 1.08 mmol) in CH$_2$Cl$_2$ (10 mL) and the reaction mixture was cooled to 0° C. under N$_2$. Triethylamine (0.4 mL, 2.85 mmol), previously dissolved in 2 mL CH$_2$Cl$_2$, was added dropwise to the mixture and stirred 30 min at 0° C. The mixture is then brought to ambient temperature and stirred 30 min followed by a recooling to 0° C. and addition of 1-methyl-piperazine (0.12 mL, 1.08 mmol). The reaction mixture was then allowed to warm to room temperature and stirred 66 h. The reaction was quenched by dilution with Et2O and washed sequentially with 10% K$_2$CO$_3$ solution (5×) and 1N HCl. The acid layer was removed and the pH adjusted to 8 using saturated sodium bicarbonate solution. Extraction of the aqueous phase with EtOAc and followed by brine wash, drying over MgSO$_4$, evaporation and recrystallization (CH$_2$Cl$_2$/hexane) produced the product as a solid (0.372 g, mp 113–116° C., 58% yield).

Physical data was as follows:

$^1$H NMR (DMSO-d$_6$, 400 MHz) δ 8.52 (d, 1H, J 8.1 Hz); 7.30–7.20 (m, 5H); 7.03 (m, 4H); 4.76 (d, 1H, J=15.1 Hz); 4.46 (m, 1H); 3.88 (m, 1H); 3.58 (brd s, 2H); 3.41 (m, 3H); 2.38–2.32 (brd s, 4H); 2.22 (s, 3H); 1.78–1.70 (m, 1H); 1.37 (s, 9H).

IR (KBr, cm$^{-1}$) 3410; 3275; 2925; 1725; 1690; 1660; 1550; 1475; 1350; 1290; 1220; 1150; 1050; 1000; 850; 700; 510.

MS (+ESI) 565.5 ([M+H]$^+$); 509.2; 475.5; 344.1; 279.1; 221.0.

Anal. Calc'd for C$_{31}$H$_{40}$N$_4$O$_6$.0.1 CH$_2$Cl$_2$: C, 64.96; H, 7.06; N, 9.77. Found: C, 64.93; H, 7.10; N, 9.62.

Other compounds prepared by the methods described herein include those set forth in Table I above which are not specifically exemplified herein.

Example A

In vitro Assay For Determining Binding of Candidate Compounds to VLA-4

An in vitro assay was used to assess binding of candidate compounds to α$_4$β$_1$ integrin. Compounds which bind in this assay can be used to assess VCAM-1 levels in biological samples by conventional assays (e.g., competitive assays). This assay is sensitive to IC$_{50}$ values as low as about 1 nM.

The activity of α$_4$β$_1$ integrin was measured by the interaction of soluble VCAM-1 with Jurkat cells (e.g., American Type Culture Collection Nos. TIB 152, TIB 153, and CRL 8163), a human T-cell line which expresses high levels of α$_4$β$_1$ integrin. VCAM-1 interacts with the cell surface in an α$_4$β$_1$ integrin-dependent fashion (Yednock, et al. J. Biol. Chem., 1995, 270:28740).

Recombinant soluble VCAM-1 was expressed as a chimeric fusion protein containing the seven extracellular domains of VCAM-1 on the N-terminus and the human IgG$_1$ heavy chain constant region on the C-terminus. The VCAM-1 fusion protein was made and purified by the manner described by Yednock, supra.

Jurkat cells were grown in RPMI 1640 supplemented with 10% fetal bovine serum, penicillin, streptomycin and glutamine as described by Yednock, supra.

Jurkat cells were incubated with 1.5 mM MnCl$_2$ and 5 μg/mL 15/7 antibody for 30 minutes on ice. Mn$^{+2}$ activates the receptor to enhance ligand binding, and 15/7 is a monoclonal antibody that recognizes an activated/ligand occupied conformation of α$_4$β$_1$ integrin and locks the molecule into this conformation thereby stabilizing the VCAM-1/α$_4$β$_1$ integrin interaction. Yednock, et al., supra. Antibodies similar to the 15/7 antibody have been prepared by other investigators. (Luque, et al, 1996, J. Biol. Chem. 271:11067) and may be used in this assay.

Cells were then incubated for 30 minutes at room temperature with candidate compounds, in various concentrations ranging from 66 μM to 0.01 μM using a standard 5-point serial dilution. 15 μL soluble recombinant VCAM-1 fusion protein was then added to Jurkat cells and incubated for 30 minutes on ice. (Yednock et al., supra.).

Cells were then washed two times and resuspended in PE-conjugated goat F(ab')$_2$ anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock, et al., supra.

Compounds having an IC$_{50}$ of less than about 15 μM possess binding affinity to α$_4$β$_1$.

When tested in this assay, each of the compounds in Examples 1–36 had an IC$_{50}$ of 15 μM or less.

Example B

In vitro Saturation Assay For Determining Binding of Candidate Compounds to α$_4$β$_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 µg/ml of the 15/7 antibody (described in the above example).

The Jurkat cells are diluted two-fold into either normal plasma samples containing known candidate compound amounts in various concentrations ranging from 66 µM to 0.01 µM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al. J. Biol. Chem., 1995, 270:28740.

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha_9\beta_1$ integrin, which is the integrin most closely related $\alpha_4\beta_1$ (Palmer et al, 1993, J. Cell Bio., 123:1289). Such binding is predictive of in vivo utility for inflammatory conditions mediated by $\alpha_9\beta_1$ integrin, including by way of example, airway hyper-responsiveness and occlusion that occurs with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease.

Accordingly, the above-described assay may be performed with a human colon carcinoma cell line, SW 480 (ATTC #CCL228) transfected with cDNA encoding $\alpha_9$ integrin (Yokosaki et al., 1994, J. Biol. Chem., 269:26691), in place of the Jurkat cells, to measure the binding of the $\alpha_9\beta_1$ integrin. As a control, SW 480 cells which express other α and $\beta_1$ subunits may be used.

Accordingly, another aspect of this invention is directed to a method for treating a disease in a mammalian patient, which disease is mediated by $\alpha_9\beta_1$ and which method comprises administering to said patient a therapeutically effective amount of a compound of this invention. Such compounds are preferably administered in a pharmaceutical composition described herein above. Effective daily dosing will depend upon the age, weight, condition of the patient which factors can be readily ascertained by the attending clinician. However, in a preferred embodiment, the compounds are administered from about 20 to 500 µg/kg per day.

Example C

In vivo Evaluation

The standard multiple sclerosis model, Experimental Autoimmune (or Allergic) Encephalomyelitis ("EAE"), was used to determine the effect of candidate compounds to reduce motor impairment in rats or guinea pigs. Reduction in motor impairment is based on blocking adhesion between leukocytes and the endothelium and correlates with anti-inflammatory activity in the candidate compound. This model has been previously described by Keszthelyi et al., Neurology, 1996, 47:1053–1059, and measures the delay of onset of disease.

Brains and spinal cords of adult Hartley guinea pigs were homogenized in an equal volume of phosphate-buffered saline. An equal volume of Freund's complete adjuvant (100 mg *mycobacterium tuberculosis* plus 10 ml Freund's incomplete adjuvant) was added to the homogenate. The mixture was emulsified by circulating it repeatedly through a 20 ml syringe with a peristaltic pump for about 20 minutes.

Female Lewis rats (2–3 months old, 170–220 g) or Hartley guinea pigs (20 day old, 180–200 g) were anesthetized with isoflurane and three injections of the emulsion, 0.1 ml each, were made in each flank. Motor impairment onset is seen in approximately 9 days.

Candidate compound treatment began on Day 8, just before onset of symptoms. Compounds were administered subcutaneously ("SC"), orally ("PO") or intraperitoneally ("IP"). Doses were given in a range of 10 mg/kg to 200 mg/kg, bid, for five days, with typical dosing of 10 to 100 mg/kg SC, 10 to 50 mg/kg PO, and 10 to 100 mg/kg IP.

Antibody GG5/3 against $\alpha_4\beta_1$ integrin (Keszthelyi et al., Neurology, 1996, 47:1053–1059), which delays the onset of symptoms, was used as a positive control and was injected subcutaneously at 3 mg/kg on Day 8 and 11.

Body weight and motor impairment were measured daily. Motor impairment was rated with the following clinical score:

| | |
|---|---|
| 0 | no change |
| 1 | tail weakness or paralysis |
| 2 | hindlimb weakness |
| 3 | hindlimb paralysis |
| 4 | moribund or dead |

A candidate compound was considered active if it delayed the onset of symptoms, e.g., produced clinical scores no greater than 2 or slowed body weight loss as compared to the control.

Example D

Asthma Model

Inflammatory conditions mediated by $\alpha_4\beta_1$ integrin include, for example, airway hyper-responsiveness and occlusion that occurs with chronic asthma. The following describes an asthma model which can be used to study the in vivo effects of the compounds of this invention for use in treating asthma.

Following the procedures described by Abraham et al, J. Clin. Invest, 93:776–787 (1994) and Abraham et al, Am J. Respir Crit Care Med, 156:696–703 (1997), both of which are incorporated by reference in their entirety, compounds of this invention are formulated into an aerosol and administered to sheep which are hypersensitive to *Ascaris suum* antigen. Compounds which decrease the early antigen-induced bronchial response and/or block the late-phase airway response, e.g., have a protective effect against antigen-induced late responses and airway hyper-responsiveness ("AHR"), are considered to be active in this model.

Allergic sheep which are shown to develop both early and late bronchial responses to inhaled *Ascaris suum* antigen are used to study the airway effects of the candidate compounds. Following topical anesthesia of the nasal passages with 2% lidocaine, a balloon catheter is advanced through one nostril into the lower esophagus. The animals are then intubated with a cuffed endotracheal tube through the other nostril with a flexible fiberoptic bronchoscope as a guide.

Pleural pressure is estimated according to Abraham (1994). Aerosols (see formulation below) are generated using a disposable medical nebulizer that provides an aerosol with a mass median aerodynamic diameter of 3.2 μm as determined with an Andersen cascade impactor. The nebulizer is connected to a dosimeter system consisting of a solenoid valve and a source of compressed air (20 psi). The output of the nebulizer is directed into a plastic T-piece, one end of which is connected to the inspiratory port of a piston respirator. The solenoid valve is activated for 1 second at the beginning of the inspiratory cycle of the respirator. Aerosols are delivered at $V_T$ of 500 ml and a rate of 20 breaths/minute. A 0.5% sodium bicarbonate solution only is used as a control.

To assess bronchial responsiveness, cumulative concentration-response curves to carbachol can be generated according to Abraham (1994). Bronchial biopsies can be taken prior to and following the initiation of treatment and 24 hours after antigen challenge. Bronchial biopsies can be preformed according to Abraham (1994).

An in vitro adhesion study of alveolar macrophages can also be performed according to Abraham (1994), and a percentage of adherent cells is calculated.

Aerosol Formulation

A solution of the candidate compound in 0.5% sodium bicarbonate/saline (w/v) at a concentration of 30.0–100.0 mg/mL is prepared using the following procedure:

A. Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure

1. Add 0.5 g sodium bicarbonate into a 100 mL volumetric flask.

2. Add approximately 90.0 mL saline and sonicate until dissolved.

3. Q.S. to 100.0 mL with saline and mix thoroughly.

B. Preparation of 30.0 mg/mL Candidate Compound: 10.0 mL

| Ingredient | Gram/10.0 mL | Final Concentration |
|---|---|---|
| Candidate Compound | 0.300 g | 30.0–100.0 mg/mL |
| 0.5% Sodium Bicarbonate/Saline Stock Solution | q.s. ad 10.0 mL | q.s ad 100% |

Procedure

1. Add 0.300 g of the candidate compound into a 10.0 mL volumetric flask.

2. Add approximately 9.7 mL of 0.5% sodium bicarbonate/saline stock solution.

3. Sonicate until the candidate compound is completely dissolved.

4. Q.S. to 10.0 mL with 0.5% sodium bicarbonate/saline stock solution and mix thoroughly.

Using a conventional oral formulation, compounds of this invention were active or are expected to be active in this model when employed at the concentrations indicated.

What is claimed is:

1. A pharmaceutical composition comprising a pharmaceutically acceptable carrier and a compound of formula I or II.

wherein:

$R^1$ has the formula:

where $R^6$ and $R^7$ are independently selected from the group consisting of hydrogen, alkyl, alkoxy, amino, cyano, halo and nitro;

Z is CH or N;

$R^2$ is selected from the group consisting of alkylene having from 2 to 4 carbon atoms in the alkylene chain, substituted alkylene having from 2 to 4 carbon atoms in the alkylene chain, heteroalkylene containing from 1 to 3 carbon atoms and from 1 to 2 heteroatoms selected from nitrogen, oxygen and sulfur and having from 2 to 4 atoms in the heteroalkylene chain, and substituted heteroalkylene containing, in the heteroalkylene chain, from 1 to 3 carbon atoms and from 1 to 2 heteroatoms selected from nitrogen, oxygen and sulfur and having from 2 to 4 atoms in the heteroalkylene chain;

$R^3$ is selected from the group consisting of hydrogen, alkyl, substituted alkyl, cycloalkyl, substituted cycloalkyl, cycloalkenyl, substituted cycloalkenyl, aryl, substituted aryl, heteroaryl, substituted heteroaryl, heterocyclic, substituted heterocyclic; or $R^3$ can be joined to $R^2$ to form a fused cycloalkyl, substituted cycloalkyl, cycloalkenyl, substituted cycloalkenyl, heterocyclic or substituted heterocyclic ring;

X is selected from the group consisting of hydrogen, alkyl, substituted alkyl, cycloalkyl, substituted cycloalkyl, alkoxy, substituted alkoxy, aryl, substituted aryl, aryloxy, substituted aryloxy, aryloxyaryl, substituted aryloxyaryl, heteroaryl, substituted heteroaryl, heterocyclic, substituted heterocyclic, acylamino, carboxyl, carboxylalkyl, carboxyl-substituted akyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, and hydroxyl with the proviso that in formula II, X is not hydroxyl;

W is oxygen or sulfur;

and pharmaceutically acceptable salts thereof.

2. A pharmaceutical composition comprising a pharmaceutically acceptable carrier and a compound of formula IA or IIA

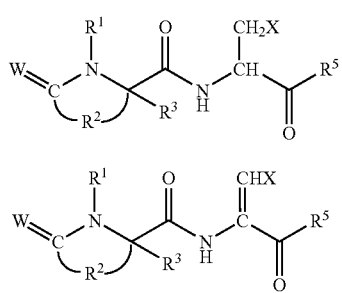

wherein:

$R^1$ has the formula:

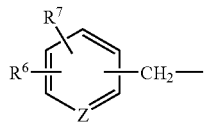

where $R^6$ and $R^7$ are independently selected from the group consisting of hydrogen, alkyl, alkoxy, amino, cyano, halo and nitro;

Z is CH or N;

$R^2$ is selected from the group consisting of alkylene having from 2 to 4 carbon atoms in the alkylene chain, substituted alkylene having from 2 to 4 carbon atoms in the alkylene chain, heteroalkylene containing from 1 to 3 carbon atoms and from 1 to 2 heteroatoms selected from nitrogen, oxygen and sulfur and having from 2 to 4 atoms in the heteroalkylene chain, and substituted heteroalkylene containing, in the heteroalkylene chain, from 1 to 3 carbon atoms and from 1 to 2 heteroatoms selected from nitrogen, oxygen and sulfur and having from 2 to 4 atoms in the heteroalkylene chain;

$R^3$ is selected from the group consisting of hydrogen, alkyl, substituted alkyl, cycloalkyl, substituted cycloalkyl, cylcloalkenyl, substituted cycloalkenyl, aryl, substituted aryl, heteroaryl, substituted heteroaryl, heterocyclic, substituted heterocyclic; or $R^3$ can be joined to $R^2$ to form a fused cycloalkyl, substituted cycloalkyl, cycloalkenyl, substituted cycloalkenyl, heterocyclic or substituted heterocyclic ring;

$R^5$ is selected from the group consisting of amino, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, —NH-adamantyl, —NHSO₂-p-CH₃-φ, —NHOY where Y is hydrogen, alkyl, substituted alkyl, aryl, or substituted aryl, and —NH(CH₂)$_p$COOY' where Y' is hydrogen, alkyl, substituted alkyl, aryl, or substituted aryl, and p is an integer of from 1 to 8, —O-cholest-5-en-3-β-yl, —OCH₂OC(O)CH₃, —O(CH₂)$_z$NHC(O)$R^9$ where z is 1 or 2 and $R^9$ is selected from the group consisting of pyrid-3-yl, N-methylpyridyl, and N-methyl-1,4-dihydro-pyrid-3-yl, —NR"C(O)—R' where R' is aryl, heteroaryl or heterocyclic and R" is hydrogen or —CH₂C(O)OCH₂CH₃;

X is selected from the group consisting of hydrogen, alkyl, substituted alkyl, cycloalkyl, substituted cycloalkyl, alkoxy, substituted alkoxy, aryl, substituted aryl, aryloxy, substituted aryloxy, aryloxyaryl, substituted aryloxyaryl, heteroaryl, substituted heteroaryl heterocyclic, substituted heterocyclic, acylamino, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, and hydroxyl with the proviso that in formula II, X is not hydroxyl;

W is oxygen or sulfur;

and pharmaceutically acceptable salts thereof with the provisos that when:

(a) $R^1$ is benzyl, $R^2$ is —CH₂CH₂—, $R^3$ is hydrogen, $R^4$ is benzyl, then $R^5$ is not ethoxy;

(b) $R^1$ is 3,4-dichlorobenzyl, $R^2$ is —CH₂CH₂—, $R^3$ is hydrogen, $R^4$ is 4-(phenyl-carbonylamino)benzyl, then $R^5$ is not methoxy;

(c) $R^1$ is benzyl, $R^2$ is —CH₂CH₂—, $R^3$ is hydrogen, $R^4$ is 4-hydroxy-benzyl, then $R^5$ is not isopropyloxy or tert-butyloxy;

(d) $R^1$ is 4-fluorobenzyl, $R^2$ is —CH₂CH₂—, $R^3$ is hydrogen, $R^5$ is tert-butyloxy, then $R^4$ is not 4-hydroxybenzyl or 4-(4-nitrophenoxycarbonyl-oxy) benzyl;

(e) $R^1$ is 4-cyanobenzyl, $R^2$ is —CH₂CH₂—, $R^3$ is hydrogen, $R^4$ is 4-hydroxy-benzyl, then $R^5$ is not tert-butyloxy; and (f) $R^1$ is benzyloxycarbonyl, $R^2$ is —NHCH₂—, $R^3$ is hydrogen, $R^5$ is tert-butyloxy, then $R^4$ is not 4-hydroxybenzyl or 4-(N,N-dimethylcarbamyl-oxy) benzyl.

3. The pharmaceutical composition according to claim 1 or claim 2 wherein Z is CH.

4. The pharmaceutical composition according to claim 3 wherein one of $R^6$ and $R^7$ is hydrogen and the other is selected from the group consisting of hydrogen, methyl, methoxy, amino, chloro, fluoro, cyano or nitro; or both $R^6$ and $R^7$ are chloro.

5. The pharmaceutical composition according to claim 1 or claim 2 wherein $R^1$ is selected from the group consisting of benzyl, 4-aminobenzyl, 3-chlorobenzyl, 4-chlorobenzyl, 3,4-dichlorobenzyl, 4-cyanobenzyl, 4-fluorobenzyl, 4-methylbenzyl, 4-methoxybenzyl, 4-nitrobenzyl, and (pyrdin-3-yl)methyl.

6. The pharmaceutical composition according to claim 1 or claim 2 wherein $R^2$ is selected from the group consisting of alkylene having 2 or 3 carbon atoms in the alkylene chain, substituted alkylene having 2 or 3 carbon atoms in the alkylene chain, heteroalkylene containing 1 or 2 carbon atoms and 1 heteroatom selected from the group consisting of nitrogen, oxygen and sulfur and having 2 or 3 atoms in the heteroalkylene chain, and substituted heteroalkylene containing, in the heteroalkylene chain, 1 or 2 carbon atoms and 1 heteroatom selected from the group consisting of nitrogen, oxygen and sulfur and having 2 or 3 atoms in the heteroalkylene chain.

7. The pharmaceutical composition according to claim 6 wherein $R^2$ is selected from the group consisting of —$CH_2CH_2$—, —$CH_2$—S—$CH_2$—, —$CH_2$—O—$CH_2$— and —$NHCH_2$—.

8. The pharmaceutical composition according to claim 1 or claim 2 wherein $R^3$ is hydrogen.

9. The pharmaceutical composition according to claim 1 or claim 2 wherein $R^3$ is joined to $R^2$ to form a fused and/or bridged cycloalkyl, substituted cycloalkyl, cycloalkenyl, substituted cycloalkenyl, heterocyclic or substituted heterocyclic ring.

10. The pharmaceutical composition according to claim 9 wherein $R^2$ and $R^3$, together with the other atoms of the nitrogen-containing ring form a 5-oxo-4-azatri-cyclo[4.2.1.0 (3,7)]nonane ring.

11. The pharmaceutical composition according to claim 1 or claim 2 wherein W is oxygen.

12. The pharmaceutical composition according to claim 2 wherein $R^5$ is selected from the group consisting of 2,4-dioxo-tetrahydrofuran-3-yl (3,4-enol), methoxy, ethoxy, iso-propoxy, n-butoxy, t-butoxy, cyclopentoxy, neo-pentoxy, 2-α-iso-propyl-4-β-methyl-cyclohexoxy, 2-β-isopropyl-4-β-methylcyclohexoxy, —$NH_2$, benzyloxy, —$NHCH_2COOH$, —$NHCH_2CH_2COOH$, —NH-adamantyl, —$NHCH_2CH_2COOCH_2CH_3$, —$NHSO_2$-p-$CH_3$-φ, —$NHOR^8$ where $R^8$ is hydrogen, methyl, iso-propyl or benzyl, O—(N-succinimidyl), —O-cholest-5-en-3-β-yl, —$OCH_2$—OC(O)C($CH_3$)$_3$, —O($CH_2$)$_z$NHC(O)$R^9$ where z is 1 or 2 and $R^9$ is selected from the group consisting of pyrid-3-yl, N-methylpyridyl, and N-methyl-1,4-dihydro-pyrid-3-yl, —NR"C(O)—R' where R' is aryl, heteroaryl or heterocyclic and R" is hydrogen or —$CH_2C(O)OCH_2CH_3$.

13. The pharmaceutical composition according to claim 1 or claim 2 wherein —$CH_2X$ is selected from the group consisting of:

4-methylbenzyl,
4-hydroxybenzyl,
4-methoxybeuzyl,
4-t-butoxybenzyl,
4-benzyloxybenzyl,
4-[φ-CH($CH_3$)O—]benzyl,
4-[φ-CH(COOH)O—]benzyl,
4-[BocNHCH$_2$C(O)NH—]benzyl,
4-chlorobenzyl,
4-[NH$_2$CH$_2$C(O)NH—]benzyl,
4-carboxybenzyl,
4-[CbzNHCH$_2$CH$_2$NH—]benzyl,
3-hydroxy-4-(φ-OC(O)NH-)benzyl,
4-[HOOCCH$_2$CH$_2$C(O)NH—]benzyl,
benzyl,
4-[2'-carboxylphenoxy—]benzyl,
4-[φ-C(O)NH—]benzyl,
3-carboxybenzyl,
4-iodobenzyl,
4-hydroxy-3,5-diiodobenzyl,
4-hydroxy-3-iodobenzyl,
4-[2'-carboxyphenyl—]benzyl,
φ-$CH_2CH_2$—,
4-nitrobenzyl,
2-carboxybenzyl,
4-[dibenzylamino]-benzyl,
4-[(1'-cyclopropylpiperidin-4'-yl)C(O)NH-—]benzyl,
4-[—NHC(O)CH$_2$NHBoc]benzyl,
4-carboxybenzyl,
4-hydroxy-3-nitrobenzyl,
4-[—NHC(O)CH($CH_3$)NHBoc]benzyl,
4-[—NHC(O)CH($CH_2$φ)NHBoc]benzyl,
isobutyl,
methyl,
4-[$CH_3$C(O)NH—]benzyl,
—$CH_2$-(3-indolyl),
n-butyl,
t-butyl-OC(O)$CH_2$—,
t-butyl-OC(O)$CH_2CH_2$—,
$H_2$NC(O)$CH_2$—,
$H_2$NC(O)$CH_2CH_2$—,
BocNH—($CH_2$)$_4$—,
HOOC$CH_2$—,
HOOC($CH_2$)$_2$—,
$H_2$N($CH_2$)$_4$—,
isopropyl,
(1-naphthyl)-$CH_2$—,
(2-naphthyl)-$CH_2$—,
(2-thiophenyl)-$CH_2$—,
φ-$CH_2$—OC(O)NH—($CH_2$)$_4$—,
cyclohexyl-$CH_2$—,
benzyloxy-$CH_2$—,
HOC$H_2$—,
5-(3-N-benzyl)imidazolyl-$CH_2$—,
2-pyridyl-$CH_2$—,
3-pyridyl-$CH_2$—,
4-pyridyl-$CH_2$—,
5-(3-N-methyl)imidazolyl-$CH_2$—,
N-benzylpiperid-4-yl-$CH_2$—,
N-Boc-piperidin-4-yl-$CH_2$—,
N-(phenylcarbonyl)piperidin-4-yl-$CH_2$—,
$H_3$CSC$H_2CH_2$—,
1-N-benzylimidazol-4-yl-$CH_2$—,
iso-propyl-C(O)NH—($CH_2$)$_4$—,
iso-butyl-C(O)NH—($CH_2$)$_4$—,
phenyl-C(O)NH—($CH_2$)$_4$—,
benzyl-C(O)NH—($CH_2$)$_4$—,
allyl-C(O)NH—($CH_2$)$_4$—,
4-(3-N-methylimidazolyl)-$CH_2$—,
4-imidazolyl,
4-[($CH_3$)$_2$NC$H_2CH_2CH_2$—O—]benzyl,
4-[(benzyl)$_2$N—]-benzyl,
4-aminobenzyl,
allyloxy-C(O)NH($CH_2$)$_4$—,
allyloxy-C(O)NH($CH_2$)$_3$—,
allyloxy-C(O)NH($CH_2$)$_2$—,
$NH_2$C(O)$CH_2$—,
2-pyridyl-C(O)NH—($CH_2$)$_4$—, 4-methylpyrid-3-yl-C(O)NH—(CH$_2$)$_4$—,
3-methylthien-2-yl-C(O)NH—(CH$_2$)4—,
2-pyrrolyl-C(O)NH—(CH$_2$)$_4$—,
2-furanyl-C(O)NH—(CH$_2$)$_4$—,
4-methylphenyl-SO$_2$—N(CH$_3$)CH$_2$C(O)NH(CH$_2$)$_4$—,
4-[cyclopentylacetylenyl]-benzyl,
4-[—NHC(O)-(N-Boc)-pyrrolidin-2-yl]-benzyl-,
1-N-methylimidazol-4-yl-CH$_2$—,
1-N-methylimidazol-5-yl-CH$_2$—,
imidazol-5-yl-CH$_2$—,
6-methylpyrid-3-yl-C(O)NH—(CH$_2$)4—,
4-[2'-carboxymethylphenyl]-benzyl,
4-[—NHC(O)NHCH$_2$CH$_2$CH$_2$-φ]-benzyl,
4-[—NHC(O)NHCH$_2$CH$_2$-φ]-benzyl,
—CH$_2$C(O)NH(CH$_2$)$_4$φ,
4-[φ(CH$_2$)$_4$O—]-benzyl,
4-[—C≡C-φ-4'-φ]-benzyl,
4-[—C≡C—CH$_2$—O—S(O)$_2$-4'-CH$_3$-φ]-benzyl,
4-[—C≡C—CH$_2$NHC(O)NH$_2$]-benzy,
4-[—C≡C—CH$_2$—O-4'-COOCH$_2$CH$_3$-φ]-benzyl,
4-[—C≡C—CH(NH$_2$)-cyclohexyl]-benzyl,
—(CH$_2$)$_4$NHC(O)CH$_2$-3-indolyl,
—(CH$_2$)$_4$NHC(O)CH$_2$CH$_2$-3-indolyl,
—(CH$_2$)$_4$NHC(O)-3-(5-methoxyindolyl),
—(CH$_2$)$_4$NHC(O)-3-(1-methylindolyl),
—(CH$_2$)$_4$NHC(O)-4-(—SO$_2$(CH$_3$)-φ),
—(CH$_2$)$_4$NHC(O)-4-(C(O)CH$_3$)-phenyl,
—(CH$_2$)$_4$NHC(O)-4-fluorophenyl,
—(CH$_2$)$_4$NHC(O)CH$_2$O-4-fluorophenyl,
4-[—C≡C-(2-pyridyl)benzyl,
4-[—C≡C—CH$_2$—O-phenyl]benzyl,
4-[—C≡C—CH$_2$OCH$_3$]benzyl,
4-[—C≡C-(3-hydroxyphenyl)]benzyl,
4-[—C≡C—CH$_2$—O-4'-(—C(O)OC$_2$H$_5$)phenyl]benzyl,
4-[—C≡C—CH$_2$CH(C(O)OCH$_3$)$_2$]benzyl,
4-[—C≡C—CH$_2$NH-(4,5-dihydro-4-oxo-5-phenyl-oxazol-2-yl),
3-aminobenzyl,
4-[—C≡C—CH$_2$CH(NHC(O)CH$_3$)C(O)OH]-benzyl,
—CH$_2$C(O)NHCH(CH$_3$)φ,
—CH$_2$C(O)NHCH$_2$-(4-dimethylamino)-φ,
—CH$_2$C(O)NHCH$_2$-4-nitrophenyl,
—CH$_2$CH$_2$C(O)N(CH$_3$)CH$_2$-φ,
—CH$_2$CH$_2$C(O)NHCH$_2$CH$_2$-(N-methyl)-2-pyrrolyl,
—CH$_2$CH$_2$C(O)NHCH$_2$CH$_2$CH$_3$,
—CH$_2$CH$_2$C(O)NHCH$_2$CH$_2$-3-indolyl,
—CH$_2$C(O)N(CH$_3$)CH$_2$phenyl,
—CH$_2$C(O)NH(CH$_2$)$_2$-(N-methyl)-2-pyrrolyl,
—CH$_2$C(O)NHCH$_2$CH$_2$CH$_3$,
—CH$_2$C(O)NHCH$_2$CH$_2$-3-indolyl,
—(CH$_2$)$_2$C(O)NHCH(CH$_3$)φ,
—(CH$_2$)$_2$C(O)NHCH$_2$-4-dimethylaminophenyl,
—(CH$_2$)$_2$C(O)NHCH$_2$-4-nitrophenyl,
—CH$_2$C(O)NH-4-[—NHC(O)CH$_3$-phenyl],
—CH$_2$C(O)NH-4-pyridyl,
—CH$_2$C(O)NH-4-[dimethylaminophenyl],
—CH$_2$C(O)NH-3-methoxyphenyl,
—CH$_2$CH$_2$C(O)NH-4-chlorophenyl,
—CH2CH$_2$C(O)NH-2-pyridyl,
—CH$_2$CH$_2$C(O)NH-4-methoxyphenyl,
—CH$_2$CH$_2$C(O)NH-3-pyridyl,
4-[(CH$_3$)$_2$NCH$_2$CH$_2$O—]benzyl,
—(CH$_2$)$_3$NHC(NH)NH—SO$_2$-4-methylphenyl,
4-[(CH$_3$)$_2$NCH$_2$CH$_2$O—]benzyl,
—(CH$_2$)$_4$NHC(O)NHCH$_2$CH$_3$,
—(CH$_2$)$_4$NHC(O)NH-phenyl,
—(CH$_2$)$_4$NHC(O)NH-4-methoxyphenyl,
4-[4'-pyridyl-C(O)NH—]benzyl,
4-[3'-pyridyl-C(O)NH—]benzyl,
4-[—NHC(O)NH-3'-methylphenyl]benzyl,
4-[-NHC(O)CH$_2$NHC(O)NH-3'-methylphenyl]benzyl,
4-[-NHC(O)-(2',3'-dihydroindol-2-yl)]benzyl,
4-[-NHC(O)-(2',3'-dihydro-N-Boc-indol-2-yl)]benzyl,
p-[—OCH$_2$CH$_2$-1'-(4'pyrimidinyl)-piperazinyl]benzyl,
4-[—OCH$_2$CH$_2$-(1'-piperidinyl)benzyl,
4-[—OCH$_2$CH$_2$-(1'-pyrrolidinyl)]benzyl,
4-[—OCH$_2$CH$_2$CH$_2$-(1'-piperidinyl)]benzyl,
—CH$_2$-3-(1,2,4-triazolyl),
4-[—OCH$_2$CH$_2$CH$_2$-4-(3'-chlorophenyl)-piperazin-1-yl—]benzyl,
4-[—OCH$_2$CH$_2$N(φ)CH$_2$CH$_3$]benzyl,
4-[—OCH$_2$-3'-(N-Boc)-piperidinyl]benzyl,
4-[di-n-pentylamino]benzyl,
4-[n-pentylamino]benzyl,
4-[di-iso-propylamino-CH$_2$CH$_2$O—]benzyl,
4-[—OCH$_2$CH$_2$-(N-morpholinyl)]benzyl,
4-[—O-(3'-(N-Boc)-piperidinyl]benzyl,
4-[—OCH$_2$CH(NHBoc)CH$_2$cyclohexyl]benzyl,
p-[OCH$_2$CH$_2$-(N-piperidinyl]benzyl,
4-[—OCH$_2$CH$_2$CH$_2$-(4-m-chlorophenyl)-piperazin-1-yl—]benzyl,
4-[—OCH$_2$CH$_2$-(N-homopiperidinyl)]benzyl,
4-[—NHC(O)-3'-(N-Boc)-piperidinyl]benzyl,
4-[—OCH$_2$CH$_2$N(benzyl)$_2$]benzyl,
—CH$_2$-2-thiazolyl,
3-hydroxybenzyl,
4-[—OCH$_2$CH$_2$CH$_2$N(CH$_3$)$_2$]benzyl,
4-[—NHC(S)NHCH$_2$CH$_2$-(N-morpholino)]benzyl,
4-[—OCH$_2$CH$_2$N(C$_2$H$_5$)$_2$]benzyl,
4-[—OCH$_2$CH$_2$CH$_2$N(C$_2$H$_5$)$_2$]benzyl,
4-[CH$_3$(CH$_2$)$_4$NH—]benzyl,
4-[N-n-butyl,N-n-pentylamino—]benzyl,
4-[—NHC(O)-4'-piperidinyl]benzyl,
4-[—NHC(O)CH(NHBoc)(CH$_2$)$_4$NHCbz]benzyl,
4-[—NHC(O)-(1',2',3',4'-tetrahydro-N-Boc-isoquinolin-1'-yl]benzyl,
p-[—OCH$_2$CH$_2$CH$_2$-1'-(4'-methyl)-piperazinyl]benzyl,
—(CH$_2$)$_4$NH-Boc,
3-[—OCH$_2$CH$_2$CH$_2$N(CH$_3$)$_2$]benzyl,
4-[—OCH$_2$CH$_2$CH$_2$N(CH$_3$)$_2$]benzyl,
3-[—OCH$_2$CH$_2$-(1'-pyrrolidinyl)]benzyl,
4-[—OCH$_2$CH$_2$CH$_2$N(CH$_3$)benzyl]benzyl,
4-[—NHC(S)NHCH$_2$CH$_2$CH$_2$-(N-morpholino)]benzyl,
4-[—OCH$_2$CH$_2$-(N-morpholino)]benzyl, 4-[—NHCH₂-(4'-chlorophenyl)]benzyl,
4-[—NHC(O)NH-(4'-cyanophenyl)]benzyl,
4-[—OCH₂COOH]benzyl,
4-[—OCH₂COO-t-butyl]benzyl,
4-[—NHC(O)-5'-fluoroindol-2-yl]benzyl,
4-[—NHC(S)NH(CH₂)₂-1-piperidinyl]benzyl,
4-[—N(SO₂CH₃)(CH₂)₃-N(CH₃)₂]benzyl,
4-[—NHC(O)CH₂CH(C(O)OCH₂φ)-NHCbz]benzyl,
4-[—NHS(O)₂CF₃]benzyl,
3-[—O—(N-methylpiperidin-4'-yl]benzyl,
4-[—C(=NH)NH₂]benzyl,
4-[—NHSO₂—CH₂Cl]benzyl,
4-[—NHC(O)-(1',2',3',4'-tetrahydroisoquinolin-2'-yl]benzyl,
4-[—NHC(S)NH(CH₂)₃-N-morpholino]benzyl,
4-[—NHC(O)CH(CH₂CH₂CH₂CH₂NH₂)NHBoc]benzyl,
4-[—C(O)NH₂]benzyl,
4-[—NHC(O)NH-3'-methoxyphenyl]benzyl,
4-[—OCH₂CH₂-indol-3'-yl]benzyl,
4-[—OCH₂C(O)NH-benzyl]benzyl,
4-[—OCH₂C(O)O-benzyl]benzyl,
4-[—OCH₂C(O)OH]benzyl,
4-[—OCH₂-2'-(4',5'-dihydro)imidazolyl]benzyl,
—CH₂C(O)NHCH₂-(4-dimethylamino)phenyl,
4-[—NHC(O)-L-2'-pyrrolidinyl-N-SO₂-4'-methylphenyl]benzyl,
4-[—NHC(O)NHCH₂CH₂CH₃]benzyl,
4-[aminobenzyl]benzyl,
4-[—OCH₂CH₂-1-(4-hydroxy-4-(3-methoxypyrrol-2-yl)-piperazinyl]benzyl,
4-[—O—(N-methylpiperidin-4'-yl)]benzyl,
3-methoxybenzyl,
4-[—NHC(O)-piperidin-3'-yl]benzyl,
4-[—NHC(O)-pyridin-2'-yl]benzyl,
4-[—NHCH₂-(4'-chlorophenyl)]benzyl,
4-[—NHC(O)—(N-(4'-CH₃-φ-SO₂)-L-pyrrolidin-2'-yl)]benzyl,
4-[—NHC(O)NHCH₂CH₂-φ]benzyl,
4-[—OCH₂C(O)NH₂]benzyl,
4-[—OCH₂C(O)NH-t-butyl]benzyl,
4-[—OCH₂CH₂-1-(4-hydroxy-4-phenyl)-piperidinyl]benzyl,
4-[—NHSO2—CH=CH₂]benzyl,
4-[—NHSO2—CH₂CH₂Cl]benzyl,
—CH₂C(O)NHCH₂CH₂N(CH₃)₂,
4-[(1'-Cbz-piperidin-4'-yl)C(O)NH—]benzyl,
4-[(1'-Boc-piperidin-4'-yl)C(O)NH—]benzyl,
4-[(2'-bromophenyl)C(O)NH—]benzyl,
4-[—NHC(O)-pyridin-4'-yl]benzyl,
4-[(4'-(CH₃)₂NC(O)O-)phenyl)-C(O)NH—]benzyl,
4-[—NHC(O)-1'-methylpiperidin-4'-yl—]benzyl,
4-(dimethylamino)benzyl,
4-[—NHC(O)-(1'-N-Boc)-piperidin-2'-yl]benzyl,
3-[—NHC(O)-pyridin-4'-yl]benzyl,
4-[(tert-butyl-O(O)CCH₂-O-benzyl)-NH—]benzyl,
[BocNHCH₂C(O)NH—]butyl,
4-benzylbenzyl,
2-hydroxyethyl,
4-[(Et)₂NCH₂CH₂CH₂NHC(S)NH—]benzyl,
4-[(1'-Boc-4'-hydroxypyrrolidin-2'-yl)C(O)NH—]benzyl,
4-[φCH₂CH₂CH₂NHC(S)NH—]benzyl,
4-[(perhydroindolin-2'-yl)C(O)NH—]benzyl,
2-[4-hydroxy-4-(3-methoxythien-2-yl)piperidin-1-yl]ethyl,
4-[1'-Boc-perhydroindolin-2'-yl)-C(O)NH—]benzyl,
4-[N-3-methylbutyl-N-trifluoromethanesulfonyl)amino]benzyl,
4-[N-vinylsulfonyl)amino]benzyl,
4-[2-(2-azabicyclo[3.2.2]octan-2-yl)ethyl-O—]benzyl,
4-[4'-hydroxypyrrolidin-2N-yl)C(O)NH—]benzyl,
4-(φNHC(S)NH)benzyl,
4-(EtNHC(S)NH)benzyl,
4-(φCH₂NHC(S)NH)benzyl,
3-[(1'-Boc-piperidin-2'-yl)C(O)NH—]benzyl,
3-[piperidin-2'-yl-C(O)NH—]benzyl,
4-[(3'-Boc-thiazolidin-4'-yl)C(O)NH—]benzyl,
4-(pyridin-3'-yl-NHC(S)NH)benzyl,
4-(CH₃—NHC(S)NH)benzyl,
4-(H₂NCH₂CH₂CH₂C(O)NH)benzyl,
4-(BocHNCH₂CH₂CH₂C(O)NH)benzyl,
4-(pyridin-4'-yl-CH₂NH)benzyl,
4-[(N,N-di(4-N,N-dimethylamino)benzyl)amino]benzyl,
4-[(1-Cbz-piperidin-4-yl)C(O)NH—]butyl,
4-[φCH₂OCH₂(BocHN)CHC(O)NH]benzyl,
4-[(piperidin-4'-yl)C(O)NH—]benzyl,
4-[(pyrrolidin-2'-yl)C(O)NH—]benzyl,
4-(pyridin-3'-yl-C(O)NH)butyl,
4-(pyridin-4'-yl-C(O)NH)butyl,
4-(pyridin-3'-yl-C(O)NH)benzyl,
4-[CH₃NHCH₂CH₂CH₂C(O)NH—]benzyl,
4-[CH₃N(Boc)CH₂CH₂CH₂C(O)NH—]benzyl,
4-(aminomethyl)benzyl,
4-[φCH₂OCH₂(H₂N)CHC(O)NH]benzyl,
4-[(1',4'-di(Boc)piperazin-2N-yl)-C(O)NH—]benzyl,
4-[(piperazin-2'-yl)-C(O)NH—]benzyl,
4-[(N-toluenesulfonylpyrrolidin-2'-yl)C(O)NH—]butyl,
4-[—NHC(O)-4'-piperidinyl]butyl,
4-[—NHC(O)-1'-N-Boc-piperidin-2'-yl]benzyl,
4-[—NHC(O)-piperidin-2'-yl]benzyl,
4-[(1'-N-Boc-2',3'-dihydroindolin-2'-yl)-C(O)NH]benzyl,
4-(pyridin-3'-yl-CH₂NH)benzyl,
4-[(piperidin-1'-yl)C(O)CH₂—O—]benzyl,
4-[((CH₃)₂CH)₂NC(O)CH₂—O—]benzyl,
4-[HO(O)C(Cbz-NH)CHCH₂CH₂—C(O)NH—]benzyl,
4-[φCH₂O(O)C(Cbz-NH)CHCH₂CH₂—C(O)NH—]benzyl,
4-[—NHC(O)-2'-methoxyphenyl]benzyl,
4-[(pyrazin-2'-yl)C(O)NH—]benzyl,
4-[HO(O)C(NH₂)CHCH₂CH₂—C(O)NH—]benzyl,
4-(2'-formyl-1',2',3',4'-tetrahydroisoquinolin-3'-yl-CH₂NH—)benzyl,
N-Cbz-NHCH₂—,
4-[(4'-methylpiperazin-1'-yl)C(O)O—]benzyl, 4-[CH₃(N-Boc)NCH₂C(O)NH—]benzyl,
4-[-NHC(O)-(1',2',3',4'-tetrahydro-N-Boc-isoquinolin-3'-yl]-benzyl,
4-[CH₃NHCH₂C(O)NH—]benzyl,
(CH₃)₂NC(O)CH₂—,
4-(N-methylacetamido)benzyl,
4-(1',2',3',4'-tetrahydroisoquinolin-3'-yl-CH₂NH—)benzyl,
4-[(CH₃)₂NHCH₂C(O)NH—]benzyl,
(1-toluenesulfonylimidizol-4-yl)methyl,
4-[(1'-Boc-piperidin-4'-yl)C(O)NH—]benzyl,
4-trifluoromethylbenzyl,
4-[(2'-bromophenyl)C(O)NH—]benzyl,
4-[(CH₃)₂NC(O)NH—]benzyl,
4-[CH₃OC(O)NH—]benzyl,
4-[(CH₃)₂NC(O)O—]benzyl,
4-[(CH₃)₂NC(O)N(CH₃)—]benzyl,
4-[CH₃OC(O)N(CH₃)—]benzyl,
4-(N-methyltrifluoroacetamido)benzyl,
4-[(1'-methoxycarbonylpiperidin-4'-yl)C(O)NH—]benzyl,
4-[(4'-phenylpiperidin-4'-yl)C(O)NH—]benzyl,
4-[(4'-phenyl-1'-Boc-piperidin-4'-yl)-C(O)NH—]benzyl,
4-[(piperidin-4'-yl)C(O)O—]benzyl,
4-[(1'-methylpiperidin-4'-yl)-O—]benzyl,
4-[(1'-methylpiperidin-4'-yl)C(O)O—]benzyl,
4-[(4'-methylpiperazin-1'-yl)C(O)NH—]benzyl,
3-[(CH₃)₂NC(O)O—]benzyl,
4-[(4'-phenyl-1'-Boc-piperdin-4'-yl)-C(O)O—]benzyl,
4-(N-toluenesulfonylamino)benzyl,
4-[(CH₃)₃CC(O)NH—]benzyl,
4-[(morpholin-4'-yl)C(O)NH—]benzyl,
4-[(CH₃CH₂)₂NC(O)NH—]benzyl,
4-[—C(O)NH-(4'-piperidinyl)]benzyl,
4-[(2'-trifluoromethylphenyl)C(O)NH—]benzyl,
4-[(2'-methylphenyl)C(O)NH—]benzyl,
4-[(CH₃)₂NS(O)₂O—]benzyl,
4-[(pyrrolidin-2'-yl)C(O)NH—]benzyl,
4-[—NHC(O)-piperidin-1'-yl]benzyl,
4-[(thiomorpholin-4'-yl)C(O)NH—]benzyl,
4-[(thiomorpholin-4'-yl sulfone)-C(O)NH—]benzyl,
4-[(morpholin-4'-yl)C(O)O—]benzyl,
3-nitro-4-(CH₃OC(O)CH₂O—)benzyl,
(2-benzoxazolinon-6-yl)methyl-,
(2H-1,4-benzoxazin-3(4H)-one-7-yl)methyl-,
4-[(CH₃)₂NS(O)₂NH—]benzyl,
4-[(CH₃)₂NS(O)₂N(CH₃)—]benzyl,
4-[(thiomorpholin-4'-yl)C(O)O—]benzyl,
4-[(thiomorpholin-4'-yl sulfone)-C(O)O—]benzyl,
4-[(piperidin-1'-yl)C(O)O—]benzyl,
4-[(pyrrolidin-1'-yl)C(O)O—]benzyl,
4-[(4'-methylpiperazin-1'-yl)C(O)O—]benzyl,
4(2'-methylpyrrolidin-1'-yl)-,
(pyridin-4-yl)methyl-,
4-[(piperazin-4'-yl)-C(O)O—]benzyl,
4-[(1'-Boc-piperazin-4'-yl)-C(O)O—]benzyl,
4-[(4'-acetylpiperazin-1'-yl)C(O)O—]benzyl,
p-[(4'-methanesulfonylpiperazin-1'-yl)-benzyl,
3nitro-4-[(morpholin-4'-yl)-C(O)O—]benzyl,
4-{[(CH₃)₂NC(S)]₂N—}benzyl,
N-Boc-2-aminoethyl-,
4-[(1,1-dioxothiomorpholin-4-yl)-C(O)O—]benzyl,
4-[(CH₃)₂NS(O)₂—]benzyl,
4-(imidazolid-2'-one-1'-yl)benzyl,
4-[(piperidin-1'-yl)C(O)O—]benzyl,
1-N-benzyl-imidazol-4-yl-CH₂—,
3,4-dioxyethylenebenzyl,
3,4-dioxymethylenebenzyl,
4-[—N(SO₂)(CH₃)CH₂CH₂CH₂N(CH₃)₂]benzyl,
4-(3'-formylimidazolid-2'-one-1'-yl)benzyl,
4-[NHC(O)CH(CH₂CH₂CH₂CH₂NH₂)NHBoc]benzyl,
[2'-[4"-hydroxy-4"-(3"'-methoxythien-2"'-yl)piperidin-2"-yl]ethoxy]benzyl, and
p-[(CH₃)₂NCH₂CH₂N(CH₃)C(O)O—]benzyl.

14. The pharmaceutical composition according to claim 1 or 2 wherein —CH₂X is selected from the group consisting of benzyl, 4-aminobenzyl, 4-hydroxy-benzyl, 4-nitrobenzyl, 3-chloro-4-hydroxybenzyl, 4(phenylC(O)—NH—)benzyl, 4-(pyridin-4-ylC(O)NH—)benzyl, 4-[(CH₃)₂NC(O)O—]benzyl, 4-[(1'-Cbz-piperidin-4'-yl)C(O)NH—]benzyl, 4-[(piperidin-4'-yl)C(O)—NH—]benzyl, 4-[—O—(N-methylpiperidin-4'-yl)]benzyl, 4-[(4'-methylpiperazin-1'-yl)C(O)O—]benzyl, 4-[(4'-(pyridin-2-yl)piperazin-1'-yl)C(O)O—]benzyl, 4-[(thiomorpholin-4'-yl)C(O)O—]benzyl, 3-chloro-4-[(CH₃)₂NC(O)O—]benzyl, and 5-(3-N-benzyl)imidazolyl-CH₂—.

15. The pharmaceutical composition according to claim 1 or claim 2 wherein =CHX is CH=- φ.

16. The pharmaceutical composition according to claim 1 or 2 wherein said compound of formula IA, IB, IIA or IIB is selected from the group consisting of:
N-(benzyl)-L-pyroglutamyl-L-phenylalanine;
N-(benzyl)-L-pyroglutamyl-L-4-(phenylcarbonylamino)phenylalanine;
N-(3,4-dichlorobenzyl)-L-pyroglutamyl-L-4-(phenylcarbonyl-amino)phenylalanine;
N-(3-chlorobenzyl)-L-pyroglutamyl-L-4-(phenylcarbonylamino)-phenylalanine;
N-(3-chlorobenzyl)-L-pyroglutamyl-L-4-(phenylcarbonylamino)-phenylalanine methyl ester;
N-(4-chlorobenzyl)-L-pyroglutamyl-L-4-(phenylcarbonylamino)-phenylalanine;
N-(4-chlorobenzyl)-L-pyroglutamyl-L-4-(phenylcarbonylamino)-phenylalanine methyl ester;
N-(4-methylbenzyl)-L-pyroglutamyl-L-4-(phenylcarbonylamino)-phenylalanine;
N-(4-methylbenzyl)-L-pyroglutamyl-L-4-(phenylcarbonylamino)-phenylalanine methyl ester;
N-(4-methoxybenzyl)-L-pyroglutamyl-L-4-(phenylcarbonylamino)-phenylalanine;
N-(4-methoxybenzyl)-L-pyroglutamyl-L-4-(phenylcarbonylamino)-phenylalanine methyl ester;
N-(3-chlorobenzyl)-L-pyroglutamyl-L-(N'-benzyl)histidine;
N-(4-methylbenzyl)-L-pyroglutamyl-L-(N'-benzyl)histidine methyl ester;
N-(4-methylbenzyl)-L-pyroglutamyl-L-(N'-benzyl)histidine;
N-(benzyl)-D-pyroglutamyl-L-phenylalanine;

N-(4-benzyl-3-oxothiomorpholin-5-carbonyl)-L-phenylalanine;

N-(4-benzyl-3-oxothiomorpholin-5-carbonyl)-L-phenylalanine ethyl ester;

N-(4-benzyl—oxomorpholin-5-carbonyl)-L-phenylalanine;

N-(4-benzyl-3-oxothiomorpholin-5-carbonyl)-L-4-nitrophenylalanine methyl ester;

N-(benzyl)-L-pyroglutanamyl-L-4-(pyridin-4-ylcarbonylamino)-phenylalanine methyl ester;

N-(benzyl)-L-pyroglutamyl-L-4-(1'-benzyloxycarbonylpiperidin-4'-ylcarbonyl -amino)phenylalanine methyl ester;

N-(benzyl)-L-pyroglutamyl-L-4-(pyridin-4-ylcarbonylamino)-phenylalanine;

N-(benzyl)-L-pyroglutamyl-L-4-(1'-benzyloxycarbonylpiperidin-4'-ylcarbonyl -amino)phenylalanine;

N-(benzyl)-L-pyroglutamyl-L-tyrosine ethyl ester;

N-(benzyl)-L-pyroglutamyl-L-4-(piperidin-4'-ylcarbonylamino)-phenylalanine;

N-(benzyl)-L-pyroglutamyl-L-4-nitrophenylalanine ethyl ester,

N-(benzyl)-L-pyroglutamyl-L-tyrosine;

N-(benzyl)-L-pyroglutamyl-L-4-(1'-methylpiperidin-4'-yloxy)-phenylalanine ethyl ester, N-(benzyl)-L-pyroglutamyl-L-4-nitrophenylalanine;

N-(benzyl)-L-pyroglutamyl-L-4-[(4'-methylpiperazin-1'-yl)-carbonyloxy]phenyl alanine ethyl ester;

N-(benzyl)-L-pyroglutamyl-L-4-(1'-methylpiperidin-4'-yloxy)phenylalanine,

N-(benzyl)-L-pyroglutamyl-L-4-[(4'-methylpiperazin-1'-yl)carbonyloxy]-phenylalanine;

N-(benzyl)-L-pyroglutamyl-L-4-(N,N-dimethylcarbamyloxy)-phenylalanine ethyl ester;

N-(benzyl)-L-pyroglutamyl-L-4-aminophenylalanine ethyl ester;

N-(benzyl)-L-pyroglutamyl-L-4-(N,N-dimethylcarbamyloxy)-phenylalanine;

N-(benzyl)-L-pyroglutamyl-L-4-(N,N-dimethylcarbamyloxy)-phenylalanine tert-butyl ester;

N-(benzyl)-L-pyroglutamyl-L-4-[(4'-methylpiperazin-1'-yl)carbonyl-oxy]phenyl-alanine tert-butyl ester;

N-(benzyl)-L-pyroglutamyl-L-4-[(thiomorpholin-4'-yl)carbonyloxy]phenylalanine tert-butyl ester;

N-(4-fluorobenzyl)-L-pyroglutamyl-L-4-[(thiomorpholin-4'-yl)carbonyloxy]phenylalanine tert-butyl ester;

N-(benzyl)-L-pyroglutamyl-L-4-(N,N-dimethylcarbamyloxy)-phenylalanine isopropyl exter;

N-(4-fluorobenzyl)-L-pyroglutamyl-L-4-(N,N-dimethylcarbamyloxy)phenylalanine tert-butyl ester;

N-(benzyl)-L-pyroglutamyl-L-3-chloro-4-hydroxyphenylalanine;

N-(4-cyanobenzyl)-L-pyroglutamyl-L-4-(N,N-dimethylcarbamyl-oxy)phenylalanine tert-butyl ester;

N-(benzyl)-L-pyroglutamyl-L-3-chloro-4-(N,N-dimethylcarbamyl-oxy)phenylalanine methyl ester;

N-(4-fluorobenzyl)-L-pyroglutamyl-L-4-[(thiomorpholin-4'-yl)carbonyloxy]phenylalanine;

N-(4-cyanobenzyl)-L-pyroglutamyl-L-4-(N,N-diemthylcarbamyloxy)-phenylalanine;

N-(4-nitrobenzyl)-L-pyroglutamyl-L-4-(N,N-dimethylcarbamyloxy)phenylalanine tert-butyl ester;

N-(benzyl)-L-pyroglutamyl-L-3-chloro-4-(N,N-dimethylcarbamyloxy)phenylalanine

N-(4-fluorobenzyl)-L-pyroglutamyl-L-4-[(4'-(pyridin-2-yl)piperazin-1'-yl)carbonyloxy]phenylalanine;

N-(4-fluorobenzyl)-L-pyroglutamyl-L-4-[(4'-(pyridin-2-yl)piperazin-1'-yl)carbonyloxy]phenylalanine tert-butyl ester;

N-(4-aminobenzyl)-L-pyroglutamyl-L-4-(N,N-dimethylcarbamyloxy)phenylalanine tert-butyl ester;

N-(pyridin-3-ylmethyl)-L-pyroglutamyl-L-tyrosine tert-butyl ester;

N-(pyridin-3-ylmethyl)-L-pyroglutamyl-L-4-(N,N-dimethylcarbamyloxy)phenylalanine;

N-(pyridin-3-ylmethyl)-L-pyroglutamyl-L-4-(N,N-dimethylcarbamyloxy)phenylalanine; tert-butyl ester N-(pyridin-3-ylmethyl)-L-pyroglutamyl-L-4-[(4'-(pyridin-2-yl)piperazin-1'-yl)carbonyloxy]phenylalanine tert-butyl ester;

N-(pyridin-3-ylmethyl)-L-pyroglutamyl-L-4-[(4'-(pyridin-2-yl)piperazin-1'-yl)-carbonyloxy]phenylalanine;

N-(4-benzyl-5-oxo-4-azatricyclo[4.2.1.0(3,7)]nonane-3-carbonyl)-L-tyrosine tert-butyl ester;

N-(4-benzyl-5-oxo-4-azatricyclo[4.2.1.0(3,7)]nonane-3-carbonyl)-L-4-(N,N-dimethylcarbamyloxy)phenylalanine tert-butyl ester;

N-(4-benzyl-5-oxo-4-azatricyclo[4.2.1.0(3,7)]nonane-3-carbonyl)-L-4-(N,N-dimethylcarbamyloxy)phenylalanine;

N-(4-fluorobenzyl)-L-pyroglutamyl-L-4-(N,N-dimethylcarbamyloxy)phenylalanine and pharmaceutically acceptable salts thereof, as well as any of the ester compounds recited above wherein one ester is replaced with another ester selected from the group consisting of methyl ester, ethyl ester, n-propyl ester, isopropyl ester, n-butyl ester, isobutyl ester, sec-butyl ester and tert-butyl ester.

17. A method for treating an inflammatory condition in a mammalian patient which condition is mediated by VLA-4, wherein said inflammatory condition is selected from the group consisting of asthma, rheumatoid arthritis, multiple sclerosis, viral meningitis, encephalitis, nephritis, diabetes, atopic dermatitis and ulcerative colitis and wherein said which method comprises administering to said patient a therapeutically effective amount of a pharmaceutical composition of claim 1 or claim 2.

* * * * *